US011881219B2

(12) United States Patent
Receveur et al.

(10) Patent No.: US 11,881,219 B2
(45) Date of Patent: Jan. 23, 2024

(54) VOICE CONTROL IN A HEALTHCARE FACILITY

(71) Applicant: Hill-Rom Services, Inc., Batesville, IN (US)

(72) Inventors: Timothy J. Receveur, Apex, NC (US); Dan R. Tallent, Hope, IN (US); Richard J. Schuman, Cary, NC (US); Eric D. Agdeppa, Cincinnati, OH (US); John S. Schroder, Apex, NC (US); Catherine Infantolino, Neptune Beach, FL (US); Sinan Batman, Cary, NC (US); Kenzi L. Mudge, Raleigh, NC (US); John V. Harmeyer, Cleves, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 211 days.

(21) Appl. No.: 17/412,788

(22) Filed: Aug. 26, 2021

(65) Prior Publication Data
US 2022/0101847 A1    Mar. 31, 2022

Related U.S. Application Data

(60) Provisional application No. 63/084,124, filed on Sep. 28, 2020.

(51) Int. Cl.
*G10L 15/22*    (2006.01)
*G10L 17/00*    (2013.01)
(Continued)

(52) U.S. Cl.
CPC .............. *G10L 15/22* (2013.01); *G10L 17/22* (2013.01); *G10L 21/0216* (2013.01);
(Continued)

(58) Field of Classification Search
CPC .......... G10L 15/22; G10L 15/26; G10L 17/00
(Continued)

(56) References Cited

U.S. PATENT DOCUMENTS 5,335,313 A    8/1994 Douglas
5,668,928 A    9/1997 Groner
(Continued)

FOREIGN PATENT DOCUMENTS

CN    100563613 C    12/2009
CN    206400521 U     8/2017
(Continued)

OTHER PUBLICATIONS

"Voice-Recognition Based Advance Patient's Room Automation," by Tejaswiny Singh et al.; International Journal of Research in Engineering and Technology; vol. 4, Issue 6; Jun. 2015; pp. 308-310 (3 pages).

(Continued)

*Primary Examiner* — George C Monikang
(74) *Attorney, Agent, or Firm* — Barnes & Thornburg LLP

(57) ABSTRACT

Systems for voice control of medical devices in a healthcare facility are disclosed herein. The systems employ continuous speech processing software, voice recognition software, natural language processing software, and other software to permit voice control of the medical devices. Systems are also provided for distinguishing which medical device from among multiple medical devices in a patient room is the particular medical device to be controlled by voice input from a caregiver or a patient.

26 Claims, 14 Drawing Sheets

(51) Int. Cl.
*G16H 40/67* (2018.01)
*G10L 17/22* (2013.01)
*G10L 21/0216* (2013.01)
*H04R 3/00* (2006.01)
*H04R 5/02* (2006.01)

(52) U.S. Cl.
CPC ............. *G16H 40/67* (2018.01); *H04R 3/005* (2013.01); *H04R 5/02* (2013.01); *G10L 2015/223* (2013.01); *G10L 2021/02166* (2013.01); *H04R 2203/12* (2013.01)

(58) Field of Classification Search
USPC .................................................. 704/231, 246
See application file for complete search history.

(56) References Cited

U.S. PATENT DOCUMENTS

| | | | |
|---|---|---|---|
| 5,781,442 A | 7/1998 | Engleson et al. | |
| 5,838,223 A | 11/1998 | Gallant et al. | |
| 6,216,104 B1 | 4/2001 | Moshfeghi et al. | |
| 6,353,809 B2 | 3/2002 | Takahashi et al. | |
| 6,462,500 B1 | 10/2002 | L'Hegarat et al. | |
| 6,980,485 B2 | 12/2005 | McCaskill | |
| 7,849,400 B2 | 12/2010 | Ritter et al. | |
| 8,244,543 B2 | 8/2012 | Alfred et al. | |
| 8,271,287 B1* | 9/2012 | Kermani | H04N 21/42222 704/275 |
| 8,310,179 B2 | 11/2012 | Clough | |
| 8,620,666 B1 | 12/2013 | Whitmore et al. | |
| 9,070,282 B2 | 6/2015 | Clough | |
| 9,230,421 B2 | 1/2016 | Reeder et al. | |
| 9,236,046 B2 | 1/2016 | Watson et al. | |
| 9,320,662 B2 | 4/2016 | Hayes et al. | |
| 9,569,593 B2 | 2/2017 | Casella dos Santos | |
| 9,830,424 B2 | 11/2017 | Dixon et al. | |
| 9,833,189 B2 | 12/2017 | Triki | |
| 9,870,776 B2 | 1/2018 | Jaiswal et al. | |
| 10,009,676 B2 | 6/2018 | Contolini et al. | |
| 10,052,249 B2 | 8/2018 | Elliott et al. | |
| 10,206,573 B2 | 2/2019 | Jeong et al. | |
| 10,284,695 B1 | 5/2019 | Geji et al. | |
| 10,290,071 B2 | 5/2019 | Heil et al. | |
| 10,347,255 B1 | 7/2019 | Paul et al. | |
| 10,363,183 B2 | 7/2019 | Ribble et al. | |
| 10,417,385 B2 | 9/2019 | Kusens et al. | |
| 10,431,220 B2 | 10/2019 | Emerick et al. | |
| 10,474,808 B2 | 11/2019 | Huster | |
| 10,517,784 B2 | 12/2019 | Zerhusen et al. | |
| 10,535,349 B2 | 1/2020 | Saxena et al. | |
| 10,546,655 B2 | 1/2020 | Owen et al. | |
| 10,561,550 B2 | 2/2020 | Bobey et al. | |
| 10,565,977 B1 | 2/2020 | Miller et al. | |
| 10,566,088 B2 | 2/2020 | McNeely et al. | |
| 10,614,814 B2 | 4/2020 | Dachiraju et al. | |
| 10,632,033 B1 | 4/2020 | Walton et al. | |
| 10,635,057 B2 | 4/2020 | Galvez et al. | |
| 10,650,823 B2 | 5/2020 | Paul et al. | |
| 10,685,664 B1 | 6/2020 | Kristjansson et al. | |
| 10,726,844 B2 | 7/2020 | Lavery et al. | |
| 10,746,840 B1 | 8/2020 | Barton et al. | |
| 10,833,947 B2 | 11/2020 | Helvey et al. | |
| 10,937,543 B1 | 3/2021 | Newton | |
| 11,062,707 B2 | 7/2021 | Judy et al. | |
| 2003/0182117 A1 | 9/2003 | Monchi et al. | |
| 2005/0021369 A1 | 1/2005 | Cohen et al. | |
| 2005/0119914 A1 | 6/2005 | Batch | |
| 2006/0049936 A1 | 3/2006 | Collins, Jr. et al. | |
| 2006/0100864 A1* | 5/2006 | Paillet | G10L 15/22 704/E15.04 |
| 2006/0279427 A1 | 12/2006 | Becker et al. | |
| 2007/0080801 A1 | 4/2007 | Weismiller et al. | |
| 2007/0156456 A1 | 7/2007 | McGillin et al. | |
| 2009/0177477 A1 | 7/2009 | Nenov et al. | |
| 2009/0212956 A1 | 8/2009 | Schuman et al. | |
| 2009/0243833 A1 | 10/2009 | Huang et al. | |
| 2010/0256983 A1 | 10/2010 | Perkins | |
| 2010/0286490 A1 | 11/2010 | Koverzin | |
| 2011/0208541 A1 | 8/2011 | Wilson et al. | |
| 2012/0136667 A1 | 5/2012 | Emerick et al. | |
| 2012/0212582 A1 | 8/2012 | Deutsch | |
| 2013/0103419 A1 | 4/2013 | Beaudry | |
| 2013/0124227 A1 | 5/2013 | Ellis | |
| 2014/0274152 A1 | 9/2014 | Lichti | |
| 2015/0106092 A1 | 4/2015 | Nolte et al. | |
| 2015/0151051 A1 | 6/2015 | Tsoukalis | |
| 2015/0186601 A1 | 7/2015 | Waxman | |
| 2015/0363563 A1 | 12/2015 | Hallwachs | |
| 2016/0180045 A1 | 6/2016 | Syed | |
| 2016/0278652 A1 | 9/2016 | Kaib et al. | |
| 2016/0338891 A1 | 11/2016 | Agdeppa et al. | |
| 2017/0005982 A1 | 1/2017 | Gould et al. | |
| 2017/0221344 A1 | 8/2017 | Cox et al. | |
| 2018/0018434 A1 | 1/2018 | Assan et al. | |
| 2018/0168755 A1 | 6/2018 | Cagle et al. | |
| 2018/0285094 A1 | 10/2018 | Housel et al. | |
| 2019/0108837 A1 | 4/2019 | Christoph et al. | |
| 2019/0116986 A1 | 4/2019 | Werner | |
| 2019/0231079 A1 | 8/2019 | Schulte | |
| 2019/0244707 A1 | 8/2019 | Becker et al. | |
| 2019/0272145 A1 | 9/2019 | Sharma et al. | |
| 2020/0005783 A1 | 1/2020 | Judy et al. | |
| 2020/0051689 A1 | 2/2020 | Hoernig | |
| 2020/0072937 A1 | 3/2020 | Baek et al. | |
| 2020/0075140 A1 | 3/2020 | Embree et al. | |
| 2020/0121186 A1 | 4/2020 | Collins, Jr. et al. | |
| 2020/0145754 A1* | 5/2020 | Christoph | H04R 3/005 |
| 2020/0186378 A1* | 6/2020 | Six | H04L 12/2803 |
| 2020/0227146 A1 | 7/2020 | Tuman, III | |
| 2020/0268579 A1 | 8/2020 | Heimbrock et al. | |
| 2020/0294503 A1 | 9/2020 | Ryu et al. | |
| 2020/0365264 A1 | 11/2020 | Girardeau et al. | |
| 2021/0051223 A1 | 2/2021 | Hatch et al. | |

FOREIGN PATENT DOCUMENTS

| | | |
|---|---|---|
| CN | 108899034 A | 11/2018 |
| CN | 110478160 A | 11/2019 |
| CN | 210467317 U | 5/2020 |
| CN | 210843903 U | 6/2020 |
| CN | 211244336 U | 8/2020 |
| EP | 1217608 B1 | 1/2005 |
| WO | WO2019179888 A1 | 9/2019 |
| WO | WO2020073091 A1 | 4/2020 |

OTHER PUBLICATIONS

"Voice control for hospital patients?" Publication Date: Nov. 2018; © 2020 SmartThings, Inc. (7 pages).

"Hospital rooms to be powered by IBM Watson IoT" by Enaie Azmbuja; © 2020 Electornic Specifier (1 page).

Abstract for "Handsfree Voice Interface for Home Network Service Using a Microphone Array Network" by Shimpei Soda et al.; IEEE; 2012 Third International Conference on Networking and Computing (2 pages).

"Amazon Echo Controlled Hill-Rom Hospital Bed" published by Bob Paradiso (12 pages).

"Design and Development of a Voice Actuated Hospital Bed for Patient Care," by Kajol H et al.; International Journal of Recent technology and Engineering (IJRTE); ISSN:2277-3878, vol. 8 issue 4; Nov. 2019; pp. 1751-1757 (7 pages).

"An Interactive Agent to Support Hospital Bed Allocation Based on Plan Validation" by Débora Cristina Engelmann; PUCRS 2019 (85 pages).

Abstract for "Soundr: Head Position and Orientation Prediction Using a Microphone Array" by Jackie Yang et al.; CHI '20: Proceedings of the 2020 CHI Conference on Human Factoring in Computing Systems; Apr. 2020 (7 pages).

Abstract for "Speech Activity Detection and Face Orientation Estimation Using Multiple Microphone Arrays and Human Position

(56) References Cited

OTHER PUBLICATIONS

Information" by Carolos T. Ishi et al.; 2015 IEEE/RSJ International Conference on Intelligent Robots and Systems (IROS).

* cited by examiner

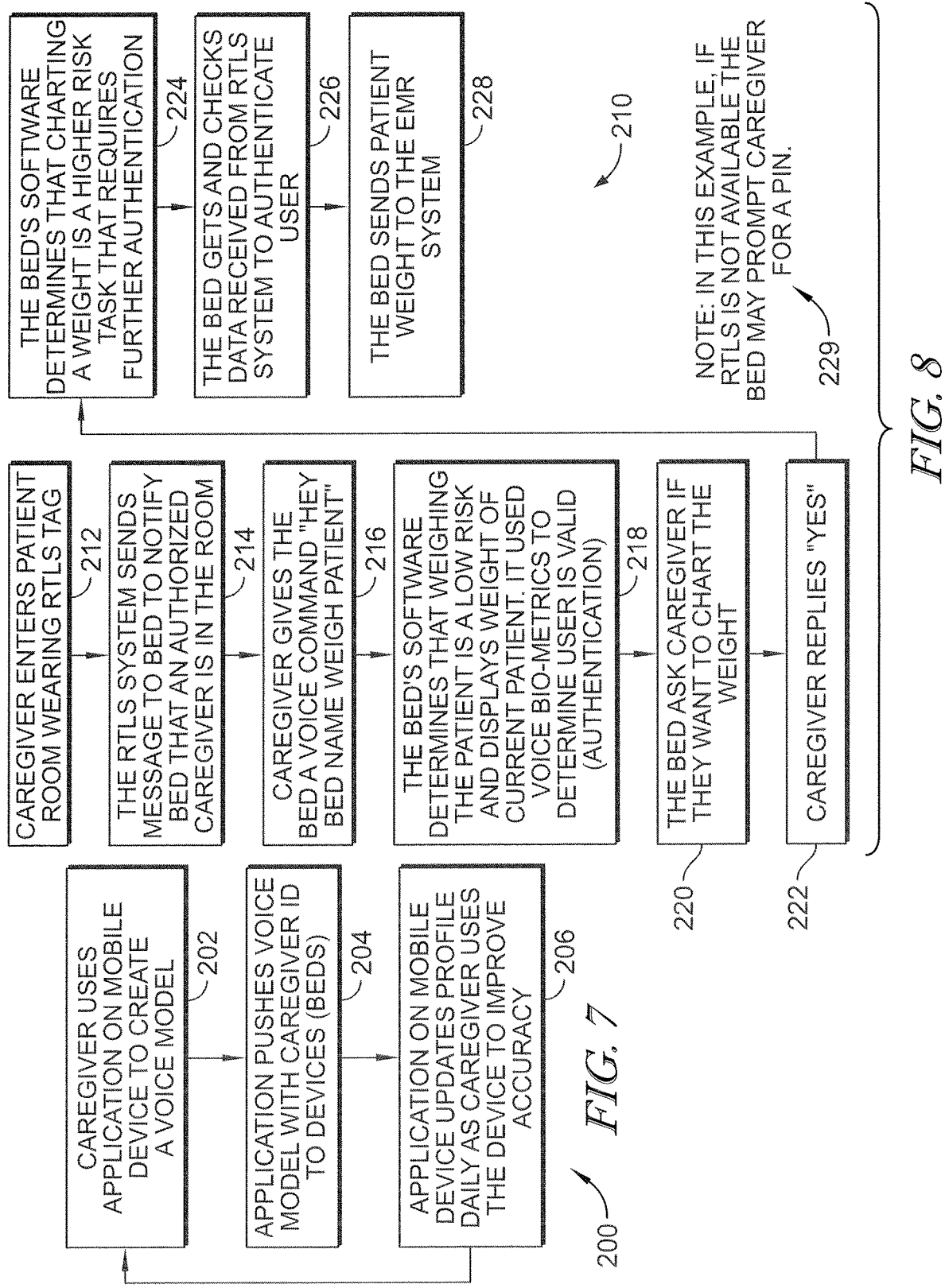

VOICE CONTROL IN A HEALTHCARE FACILITY

The present application claims the benefit, under 35 U.S.C. § 119(e), of U.S. Provisional Patent Application No. 63/084,124, filed Sep. 28, 2020, which is hereby incorporated by reference herein in its entirety.

BACKGROUND

The present disclosure relates to voice control of equipment and particularly, to voice control of equipment in a healthcare facility. More particularly, the present disclosure relates to voice control of medical devices, including patient beds, in a healthcare facility.

In patient rooms of a healthcare facility, several pieces of sophisticated medical devices or equipment are typically present. Such medical devices usually include a patient bed. Other medical devices typically found in a patient room include patient monitors such as vital signs monitors, intravenous (IV) pumps, and therapy devices such as respiratory therapy devices, ventilators, and compression therapy devices to prevent deep vein thrombosis (DVT), just to name a few. Features on the patient beds and other medical devices are sometimes not used properly or not used at all, due to ease of use issues. That is, caregivers sometimes do not know how to properly use the medical equipment because sophisticated graphical screen navigation through a multitude of screen hierarchies may be required to reach the needed operational screens for any particular medical device function. For example, zeroing a patient bed (e.g., setting the tare weight) and weighing patients is sometimes not performed by caregivers in the proper manner. The fact that caregivers may need to operate many different medical devices by interacting with a variety of different user interfaces for the medical devices adds to the problem of improper use.

More recently, voice control of devices, including medical devices, is becoming more prevalent. An increase in computer processing speeds and sophistication in voice processing algorithms allows for devices to more successfully be controlled by voice inputs spoken by users. Voice inputs to control some or all of the functions of medical devices in a healthcare setting provides caregivers with a user interface experience that is more intuitive and natural, thereby enhancing the likelihood that caregivers properly implement medical device functions that previously were implemented incorrectly or not implemented at all. However, there is an ongoing need to implement voice control of medical devices that is safe and intuitive. For example, because there are typically multiple medical devices in any given room, it is desirable that only authorized users (e.g., caregivers and/or patients) are permitted to control the medical devices by voice and it is desirable that only the medical device intended to be controlled by voice is the one that is actually controlled such that other medical devices not intended for voice control are not controlled by a spoken voice command. For example, in semi-private room settings having two patient beds, two IV pumps, two vital signs monitors, and so forth, there is an ongoing need to assure that only the desired piece of medical equipment is the one controlled by each voice command that is spoken. Accordingly, there is an ongoing need for improvement in the area of voice control of medical equipment in a healthcare facility.

SUMMARY

An apparatus, system, or method may comprise one or more of the features recited in the appended claims and/or the following features which, alone or in any combination, may comprise patentable subject matter:

According to a first aspect of the present application, a voice control system for a healthcare facility may be provided. The voice control system may include a patient bed that may have a weigh scale to weigh a patient that may be supported on the patient bed and that may have a display screen to display the patient's weight. The voice control system of the first aspect may further include a voice recorder that may be configured to record digital models of voices of a plurality of caregivers and a server to which the digital models may be transferred for determining voice biometrics of each caregiver of the plurality of caregivers. The patient bed of the first aspect may be configured to receive a voice input from a first caregiver of the plurality of caregivers that may instruct the patient bed to weigh the patient. The patient bed may be configured to communicate with the server to confirm that the caregiver may be authorized to control the patient bed by the voice input based on the voice biometrics. After confirmation that the first caregiver may be authorized to control the patient bed, the patient may be weighed by the weigh scale and the patient's weight may be displayed on the display screen.

In some embodiments of the first aspect, the voice recorder may be included in a computer. Alternatively or additionally, the voice recorder may be included in a mobile phone. Optionally, a caregiver identification (ID) may be transmitted to the server by the voice recorder of the first aspect with the digital model of each caregiver of the plurality of caregivers. If desired, the patient bed may be configured to receive a zero scale voice input from the first caregiver that may instruct the patient bed to zero the weigh scale by measuring a tare weight with the weigh scale when the patient is not in bed. In this regard, the patient bed may be configured to communicate with the server to confirm that the caregiver may be authorized to control the patient bed by the zero scale voice input based on the voice biometrics. After confirmation that the first caregiver is authorized to control the patient bed of the first aspect, the patient bed may zero the weigh scale.

It is contemplated by the present disclosure that the patient bed of the first aspect may be configured to display an accept button on the display screen for selection by the first caregiver to accept the displayed patient weight for storage in one or both of memory of the patient bed and an electronic medical record of the patient. If the displayed weight that has been accepted by the first caregiver is different than a previously accepted patient weight by a threshold amount, the patient bed may display a message on the display screen instructing the first caregiver to check to determine if the weigh scale of the patient bed has been properly zeroed. If no problems are detected by the patient bed of the first aspect, the patient bed may display a message on the display screen that may indicate that the patient weight was successfully stored in one or both of the memory of the patient bed and the electronic medical record of the patient.

In some embodiments, the voice control system of the first aspect further may include a real time locating system (RTLS) that may determine the locations of the plurality of caregivers in the healthcare facility. The server may use information from the RTLS in addition to the voice biometrics to confirm that the first caregiver is authorized to control the patient bed of the first aspect by the voice input. Optionally, the patient bed of the first aspect may be configured to display a personal identification number (PIN) screen on the display screen for the first caregiver to enter a PIN and the server may use the PIN in addition to the voice biometrics to confirm that the first caregiver is authorized to control the patient bed by the voice input. The use of the PIN in addition to the use of the voice biometrics to determine that the first caregiver is authorized may be in addition to, or in lieu of, the use of information from the RTLS. If desired, the patient bed of the first aspect may be configured to display a voice input button on the display screen that is selectable by the first caregiver to enable the patient bed to receive the voice input.

According to a second aspect of the present disclosure, a voice control system for a healthcare facility may include a medical device that may be used in care for a patient and a mobile device that may include a voice recorder that may be configured to record a digital model of a voice of a caregiver. The digital model may be transferred to the medical device from the mobile device. The medical device may be configured to determine voice biometrics of the caregiver based on the digital model. The medical device may be configured to receive a voice input from the caregiver that may instruct the medical device to carry out a function. The medical device may be configured to confirm that the caregiver may be authorized to control the medical device by the voice input based on the voice biometrics. After confirmation that the caregiver may be authorized to control the medical device, the function may be carried out by the medical device.

In some embodiments of the voice control system of the second aspect, a caregiver identification (ID) of the caregiver may be transmitted to the medical device from the mobile device along with the digital model of the voice of the caregiver. If desired, the medical device of the second aspect may be configured to display an accept button on a display screen for selection by the caregiver to accept displayed patient information for storage in one or both of memory of the medical device and an electronic medical record of the patient. If no problems are detected by the medical device, the medical device may display a message on the display screen that may indicate that the patient information was successfully stored in one or both of the memory of the medical device and the electronic medical record of the patient.

It is contemplated by the present disclosure that the voice control system of the second aspect, further may include a real time locating system (RTLS) that may determine the location of the caregiver in the healthcare facility. The medical device may use information from the RTLS in addition to the voice biometrics to confirm that the caregiver may be authorized to control the medical device by the voice input. Alternatively or additionally, the medical device may be configured to display a personal identification number (PIN) screen on a display screen for the caregiver to enter a PIN and the medical device may use the PIN in addition to the voice biometrics to confirm that the first caregiver is authorized to control the medical device by the voice input. The use of the PIN in addition to the use of the voice biometrics to determine that the first caregiver is authorized may be in addition to, or in lieu of, the use of information from the RTLS. Optionally, the medical device may be configured to display a voice input button on a display screen that may be selectable by the caregiver to enable the medical device to receive the voice input.

According to a third aspect of the present disclosure, a voice control system for a healthcare facility may include a patient bed that may have a weigh scale to weigh a patient supported on the patient bed and that may have a display screen to display the patient's weight. A real time locating system (RTLS) may be provided to track locations of a plurality of caregivers in the healthcare facility. The RTLS of the third aspect may be configured to send a message to the patient bed that may notify the patient bed that a first caregiver may have entered into a room in which the patient bed may be situated. The patient bed of the third aspect may be configured to receive a voice input from the first caregiver that may instruct the patient bed to weigh the patient. Furthermore, the patient bed may be configured to confirm that the first caregiver may be authorized to control the patient bed by the voice input based on voice biometrics of the first caregiver stored in memory of the patient bed. After confirmation that the first caregiver may be authorized to control the patient bed, the patient may be weighed by the weigh scale and the patient's weight may be displayed on the display screen.

In some embodiments of the third aspect, the patient bed may be configured to play an audio message that may inquire whether the first caregiver wants to chart the displayed patient weight for storage in an electronic medical record of the patient. In response to the first caregiver responding vocally in the affirmative to the audio message, the patient bed may communicate with the RTLS to re-confirm that the first caregiver may be authorized to chart the patient weight for storage in the electronic medical record of the patient. After the RTLS of the third aspect re-confirms that the first caregiver may be authorized, the patient weight may be transmitted to an EMR system for storage in the electronic medical record of the patient.

Optionally, the patient bed of the third aspect may be configured to display a chart button on the display screen for selection by the first caregiver to chart the displayed patient weight for storage in an electronic medical record of the patient. In response to selection of the chart button by the first caregiver, the patient bed of the third aspect may communicate with the RTLS to re-confirm that the first caregiver may be authorized to chart the patient weight for storage in the electronic medical record of the patient. After the RTLS re-confirms that the first caregiver may be authorized, the patient weight may be transmitted to an EMR system for storage in the electronic medical record of the patient.

The present disclosure contemplates that, in response to the first caregiver responding vocally in the affirmative to the audio message, the patient bed of the third aspect may display a personal identification number (PIN) screen on the display screen for the first caregiver to enter a PIN and the patient bed may use the PIN to re-confirm that the first caregiver may be authorized to chart the patient weight for storage in the electronic medical record of the patient. After the patient bed of the third aspect re-confirms that the first caregiver is authorized based on the PIN, the patient weight may be transmitted to an EMR system for storage in the electronic medical record of the patient.

Alternatively, in response to selection of the chart button by the first caregiver, the patient bed of the third aspect displays a personal identification number (PIN) screen on the display screen for the first caregiver to enter a PIN and the patient bed may use the PIN to re-confirm that the first caregiver may be authorized to chart the patient weight for storage in the electronic medical record of the patient. In such alternative embodiments of the third aspect, after the patient bed re-confirms that the first caregiver may be authorized based on the PIN, the patient weight may be transmitted to an EMR system for storage in the electronic medical record of the patient.

In a variant of the third aspect, a voice control system for a healthcare facility includes a patient bed that may have a weigh scale to weigh a patient that may be supported on the patient bed and that may have a display screen to display the patient's weight. A real time locating system (RTLS) may be provided to track locations of a plurality of caregivers in the healthcare facility. The RTLS may be configured to send a message to the patient bed that may notify the patient bed that a first caregiver may have entered into a room in which the patient bed may be situated. The patient bed may be configured to receive a voice input from the first caregiver that may instruct the patient bed to weigh the patient. The patient bed may be configured to confirm that the first caregiver may be authorized to control the patient bed. After confirmation that the first caregiver may be authorized to control the patient bed, the patient may be weighed by the weigh scale.

In some embodiments of the variant of the third aspect, the patient bed may be configured to confirm that the first caregiver may be authorized to the control the patient bed by the voice input based on voice bio-metrics of the first caregiver that may be stored in memory of the patient bed. Optionally, the patient bed of the variant of the third aspect may be configured to display the patient's weight on the display screen after the patient is weighed.

According to a fourth aspect of the present disclosure, a patient bed may include a frame that may be configured to support a patient and circuitry that may be carried by the frame and that may include a processor, memory, a speaker, a microphone, and a transmitter. The memory of the fourth aspect may store software that may be configured to receive voice inputs via the microphone and output voice messages via the speaker. In response to receiving a first voice input that may include a fall prevention check statement from a caregiver that may be detected by the microphone of the fourth aspect, the processor and software may cooperate to determine whether the patient bed may be properly configured according to a fall prevention protocol. If the patient bed of the fourth aspect is not properly configured according to the fall prevention protocol, the circuitry may be configured to prompt the caregiver to rectify one or more patient bed settings so as to be configured according to the fall prevention protocol. If the patient bed of the fourth aspect is properly configured according to the fall prevention protocol, the circuitry may be configured to play a confirmation message via the speaker to confirm to the caregiver that the patient bed may be properly configured according to the fall prevention protocol. After the confirmation message is played, the circuitry may be configured to convey a charting query to the caregiver regarding whether fall prevention protocol compliance information should be charted to the patient's electronic medical record. In response to receiving an affirmative input from the caregiver in response to the charting query of the fourth aspect, the circuitry may transmit via the transmitter the fall prevention protocol compliance information for storage in the patient's electronic medical record.

In some embodiments of the fourth aspect, the circuitry may be configured to prompt the caregiver to rectify the one or more patient bed settings by playing an audio message via the speaker of the circuitry with information regarding the patient bed settings that need to be rectified. Alternatively or additionally, the circuitry of the fourth aspect may further include a display screen and the circuitry may prompt the caregiver to rectify the one or more patient bed settings by displaying a visual message on the display screen with information regarding the patient bed settings that need to be rectified. For example, the visual message may include textual information or pictorial information.

The present disclosure contemplates that the patient bed of the fourth aspect further may include a plurality of siderails that may be coupled to the frame and each siderail may be movable between a raised position blocking patient egress from the frame and a lowered position unblocking patient egress from the frame. The patient bed of the fourth aspect may include a plurality of casters that may be coupled to the frame and a bed exit system that may be carried by the frame and that may be coupled to the circuitry. The frame of the fourth aspect may include a base frame and an upper frame supported above the base frame by a lift system. In such embodiments, in order for the bed of the fourth aspect to be properly configured according to the fall prevention protocol, two or more siderails of the frame may be required to be in the respective raised positions, at least one caster of the plurality of casters may be required to be braked, the bed exit system may be required to be armed so as to monitor for a bed exit condition of the patient, and the upper frame may be required to be in a low position relative to the base frame.

If desired, the circuitry of the fourth aspect may be configured to convey the charting message to the caregiver by playing an audio charting message via the speaker of the circuitry inquiring whether the caregiver wishes to chart the fall prevention compliance information to the patient's electronic medical record. In such scenarios, the affirmative input from the caregiver may be a spoken statement that is detected by the microphone. Alternatively or additionally, the circuitry of the fourth aspect further may include a display screen and the circuitry may be configured to convey the charting query to the caregiver by displaying the charting query on the display screen. In such scenarios, the affirmative input from the caregiver may be a selection of a button that may be displayed on the display screen.

In some embodiments of the patient bed of the fourth aspect, after the confirmation message is played and before the charting query is made, the circuitry may be configured to convey a nurse call pendant availability query to the caregiver inquiring whether a nurse call pendant is within reach of the patient. For example, the circuitry may be configured to convey the nurse call pendant availability query to the caregiver by playing an audio availability message via the speaker of the circuitry. Alternatively or additionally, the circuitry of the fourth aspect may further have a display screen and the circuitry may be configured to convey the nurse call pendant availability query to the caregiver by displaying the nurse call pendant availability query on the display screen.

Optionally, if the caregiver answers the nurse call pendant availability query negatively, the circuitry may be configured to prompt the caregiver to move the nurse call pendant to be within reach of the patient and to confirm that the nurse call pendant has been moved to be within reach of the patient. For example, the circuitry of the fourth aspect may be configured to prompt the caregiver to move the nurse call pendant to be within reach of the patient by playing an audio message via the speaker of the circuitry. Alternatively or additionally, the circuitry of the fourth aspect further may include a display screen and the circuitry may be configured to prompt the caregiver to move the nurse call pendant to be within reach of the patient by displaying a visual message on the display screen.

The present disclosure further contemplates that the circuitry of the fourth aspect may be configured to confirm that the nurse call pendant has been moved to be within reach of the patient in response to receipt of a spoken confirmation message from the caregiver that may be detected by the microphone. Alternatively or additionally, the circuitry of the fourth aspect further may include a display screen and the circuitry may be configured to confirm that the nurse call pendant has been moved to be within reach of the patient in response to a confirmation button displayed on the display screen being selected by the caregiver.

In some embodiments of the patient bed of the fourth aspect, after the confirmation message is played and before the charting query is made, the circuitry may be configured to convey a clear pathways query to the caregiver inquiring whether pathways around the patient bed are unobstructed. For example, the circuitry of the fourth aspect may be configured to convey the clear pathways query to the caregiver by playing an audio clear pathways message via the speaker of the circuitry. Alternatively or additionally, the circuitry of the fourth aspect further may include a display screen and the circuitry may be configured to convey the clear pathways query to the caregiver by displaying the clear pathways query on the display screen.

Optionally, if the caregiver answers the clear pathways query negatively, the circuitry may be configured to prompt the caregiver to clear the pathways around the patient bed and to confirm that the pathways around the patient bed have been cleared. For example, the circuitry of the fourth aspect may be configured to prompt the caregiver to clear the pathways around the patient bed by playing an audio message via the speaker of the circuitry. Alternatively or additionally, the circuitry of the fourth aspect further may include a display screen and the circuitry may be configured to prompt the caregiver to clear the pathways around the patient bed by displaying a visual message on the display screen.

The present disclosure further contemplates that the circuitry of the fourth aspect may be configured to confirm that the pathways around the patient bed are clear in response to receipt of a spoken confirmation message from the caregiver that may be detected by the microphone. Alternatively or additionally, the circuitry of the fourth aspect further may include a display screen and the circuitry may be configured to confirm that the pathways around the patient bed are clear in response to a confirmation button displayed on the display screen being selected by the caregiver.

In a variant of the fourth aspect, a patient bed may include a frame that may be configured to support a patient and circuitry that may be carried by the frame and that may include a processor, memory, a speaker, a microphone, and a transmitter. The memory may store software that may be configured to receive voice inputs via the microphone and output voice messages via the speaker. In response to receiving a first voice input that may include a fall prevention check statement from a caregiver that may be detected by the microphone, the processor and software may cooperate to determine whether the patient bed may be properly configured according to a fall prevention protocol. If the patient bed is not properly configured according to the fall prevention protocol, the circuitry may be configured permit one or more patient bed settings to be rectified so as to be configured according to the fall prevention protocol. If the patient bed is properly configured according to the fall prevention protocol, the circuitry may be configured to play a confirmation message via the speaker to confirm to the caregiver that the patient bed may be properly configured according to the fall prevention protocol.

In some embodiments of the variant of the fourth aspect, the circuitry may be configured to prompt the caregiver to rectify the one or more patient bed settings so as to be configured according to the fall prevention protocol. After the confirmation message is played, the circuitry of the variant of the fourth aspect may be configured to convey a charting query to the caregiver regarding whether fall prevention protocol compliance information should be charted to the patient's electronic medical record. In response to receiving an affirmative input from the caregiver in response to the charting query, the circuitry may transmit via the transmitter the fall prevention protocol compliance information for storage in the patient's electronic medical record.

According to a fifth aspect of the present disclosure, a system to mitigate risk to a patient in a healthcare setting may be provided. The system of the fifth aspect may include a medical product that may have at least one function that, when operated, may have a possibility of causing harm to the patient. Circuitry may be carried by the medical product and may include a processor and memory storing software. The system of fifth aspect also may have an array of microphones that may be configured to receive voice inputs from a person that may be in the vicinity of the medial product. The array of microphones may be in communication with the circuitry and the software may be configured to cooperate with the array of microphones to use beamforming techniques to infer a direction that the person's eyes are pointed based on the voice inputs. The circuitry may be configured to stop the at least one function that may have the possibility of causing harm to the patient in response to a vocal stop command being spoken by the person while the person's eyes may be inferred to be pointed toward the medical product.

In some embodiments, the medical product of the fifth aspect may include a patient bed and the array of microphones may be mounted to the patient bed. Optionally, the patient bed may include at least one siderail that may be moveable between a raised position blocking the patient from egressing from the patient bed and a lowered position unblocking the patient from egressing from the patient bed. At least one microphone of the array of microphones may be mounted to the at least one siderail.

If desired, the medical product optionally may include a patient bed and the array of microphones may be mounted to either or both of a room wall or a ceiling of a patient room in which the patient bed is situated. For example, the array of microphones may include a first microphone mounted to the medical product and a second microphone mounted to either a room wall or a ceiling of a patient room in which the medical product is situated. Further optionally, the medical product of the fifth aspect may include a patient lift and the array of microphones may be mounted to either or both of a room wall and a ceiling of a patient room in which the patient lift is situated. If desired, the patient lift may comprise a mobile patient lift or a ceiling-mounted patient lift.

Optionally, the medical product of the fifth aspect may comprise a patient bed that may support a mattress and the at least one function may include one or more of the following: movement of a mattress support section of a mattress-support deck of the patient bed, movement of an upper frame of the patient bed relative to a base frame of the patient bed, operation of a percussion and vibration (P&V) therapy function of the mattress of the patient bed, operation of a turn assist function of the mattress of the patient bed, or operation of a continuous lateral rotation therapy (CLRT) function of the mattress of the patient bed. Further optionally, the medical product of the fifth aspect may comprise a surgical table and the at least one function may include movement of a first surgical table portion relative to a second surgical table portion.

In some embodiments, the array of microphones of the fifth aspect may be in wireless communication with the circuitry of the medical product. Alternatively or additionally, the array of microphones may be in wired communication with the circuitry of the medical product. Is desired, the system of the fifth aspect further may include a mobile phone that may be carried by the person. The mobile phone may be configured to receive voice commands from the person and transmit command messages corresponding to the voice commands to the medical product to commence operation of the at least one function. Alternatively or additionally, the system of the fifth aspect further may include at least one computer that may be remote from the medical product. The at least one computer may have clinical voice recognition software. The array of microphones may communicate voice commands received from the person to the at least one computer. The at least one computer may be configured to transmit command messages corresponding to the voice commands to the medical product to commence operation of the at least one function.

It is contemplated by the present disclosure that the circuitry of the fifth aspect may be configured not to stop the at least one function that may have the possibility of causing harm to the patient in response to a vocal stop command being spoken by the person while the person's eyes may not be inferred to be pointed toward the medical product. If desired, the circuitry of the fifth aspect may be configured to be trained to recognize the patient's voice and the circuitry may be configured to stop the at least one function that may have the possibility of causing harm to the patient in response to a patient-originated vocal stop command being spoken by the patient without regard to directionality of the patient's eyes. In such embodiments, the medical product of the fifth aspect may comprise a patient bed on which the patient is supported.

According to a sixth aspect of the present disclosure, a system for associating a medical device to a location in a healthcare facility may be provided. The system of the sixth aspect may include a medical device that may have circuitry that may include a processor, memory, and a transmitter. The system of the sixth aspect may also have at least one microphone that may be communicatively coupled to the circuitry. The memory may store software that is configured to receive voice inputs via the at least one microphone. The system of the sixth aspect also may have a locating system that may include at least one locating computer that may be configured to store device-to-room associations. The circuitry of the medical device may be configured to receive a voice input from a person via the at least one microphone indicating a location identification (ID) at which the medical device may be located. The circuitry may be configured to store the location ID in the memory of the medical device and to transmit the location ID to the at least one locating computer along with a medical device ID. The at least one locating computer may be configured to establish a first device-to-room association based on the medical device ID and the location ID that may be transmitted from the medical device.

In some embodiments, the at least one microphone of the sixth aspect may be carried by the medical device. Optionally, the at least one microphone of the sixth aspect may include an array of microphones that may be carried by the medical device. Further optionally, the at least one microphone of the sixth aspect may be spaced apart from the medical device and may be mounted at the location. For example, the at least one microphone of the sixth aspect may include an array of microphones that may be spaced apart from the medical device and that may be mounted at the location. If desired, the at least one microphone of the sixth aspect may be configured to communicate wirelessly with the circuitry of the medical device.

The present disclosure contemplates that the at least one microphone of the sixth aspect may include a first microphone that may be carried by the medical device and a second microphone that may be spaced apart from the medical device. In such embodiments of the sixth aspect, the second microphone may be configured to communicate wirelessly with the circuitry of the medical device.

In some embodiments, the circuitry of the medical device of the sixth aspect may further include a display screen that may display the location ID after the circuitry receives the location ID via the at least one microphone. Optionally, the circuitry of the medical device of the sixth aspect may be configured to wirelessly transmit the location ID and the bed ID for receipt by the at least one locating computer. Further optionally, the at least one locating computer may store a patient-to-location association and, after receipt of the medical device ID and location ID, may establish a device-to-patient association. In such embodiments, the at least one locating computer may be configured to transmit to the medical device a patient ID corresponding to a patient to which the device-to-patient association pertains. If desired, the circuitry of the medical device of the sixth aspect may include a display screen and the circuitry may be configured to display the patient ID on the display screen.

The present disclosure further contemplates that the circuitry of the medical device of the sixth aspect may be configured to generate a query to the person for additional information if the voice input does not include a valid location ID. For example, the circuitry of the medical device of the sixth aspect further may include at least one speaker and the query may include an audible message played through the at least one speaker. Alternatively or additionally, the circuitry of the medical device of the sixth aspect further may include a display screen and the query may include a text message that may be displayed on the display screen.

In some embodiments of the sixth aspect, the circuitry of the medical device further may include a display screen and the circuitry may be configured to display a location menu of valid location ID's for the healthcare facility in response to a vocal request by the person. In this regard, the circuitry of the medical device may be configured to display a menu hierarchy relating to location options and the circuitry may be configured to permit the person to navigate vocally through the menu hierarchy to reach the location menu.

Optionally, the circuitry of the medical device of the sixth aspect further may include at least one speaker and the circuitry may be configured to play an audible confirmation message through the at least one speaker in response to the location ID included in the voice input being a valid location ID. Further optionally, the circuitry of the medical device of the sixth aspect may be configured to receive a disassociate input from the person via the at least one microphone indicating that the first device-to-room association should be canceled. The circuitry may be configured to transmit the disassociate input to the at least one locating computer along with the medical device ID. The at least one locating computer may be configured to cancel the first device-to-room association based on the medical device ID and the disassociate input transmitted from the medical device.

According to a seventh aspect of the present disclosure, a system for voice control of medical devices in a room may include a first medical device that may have first circuitry that may include a first processor, first memory, and a first microphone, and a second medical device that may have second circuitry that may include a second processor, second memory, and a second microphone. The first and second medical devices of the seventh aspect may be in sufficiently close proximity to each other that a voice input spoken by a person may be received by both of the first and second microphones. The first circuitry of the first medical device may be configured to become enabled for voice control in response to the voice input including a first code phrase and the second circuitry of the second medical device may be configured to become enabled for voice control in response to the voice input including a second code phrase.

In some embodiments of the seventh aspect, the first code phrase and the second code phrase each may begin with a common code word. For example, the common code word may comprise the word "hey." Optionally, the first code phrase may include a first unique name that may correspond to the first medical device and that may be spoken immediately after the common code word and the second code phrase may include a second unique name that may correspond to the second medical device and that may be spoken immediately after the common code word. In situations in which the first and second medical devices may be of the same model name, the first unique name may be of the format "model name A" and the second unique name may be of the format "model name B." Alternatively or additionally, in situations in which the first and second medical devices may be of the same model name, the first unique name may be of the format "model name 1" and the second unique name may be of the format "model name 2."

If desired, after each of the first and second medical devices of the seventh aspect becomes enabled for voice control, the respective first and second circuitry may be enabled for receiving voice commands to control functions of the respective first and second medical device for a threshold period of time. After the threshold period of time elapses without the respective first and second medical device receiving at least one voice command, the respective first and second medical device may be become disabled from voice control. It is contemplated by the present disclosure that, in response to receiving a valid voice command during the threshold period of time, the threshold period of time may reset.

According to an eighth aspect of the present disclosure, a system for enabling voice control of a medical device may include an identifier article that may be carried by a caregiver and that may be configured to transmit a wireless identification (ID) signal. The system of the eighth aspect also may include a medical device that may have circuitry that may include a processor, memory, a microphone, a transmitter, and a proximity detector that may be configured to receive the wireless ID signal from the identifier article when the identifier article may be within three feet or less of the medical device. The system of the eighth aspect further may include at least one voice control authorization (VCA) computer that may be remote from the medical device and that may be communicatively coupled to the medical device. In response to receipt of the wireless ID signal by the proximity detector, the circuitry may transmit via the transmitter ID data that may be contained in the wireless ID signal to the VCA computer. The VCA computer may be configured to verify that the ID data may correspond to a caregiver who may be authorized to control the medical device via voice inputs. If caregiver authorization is verified by the VCA computer, the VCA computer may be configured to transmit an authorization message to the medical device. In response to receipt of the authorization message by the circuitry of the medical device, voice control of the medical device may be enabled.

In some embodiments of the eighth aspect, the identifier article may include a mobile phone. Alternatively or additionally, the identifier article of the eighth aspect may include a radio frequency identification (RFID) badge. Further alternatively or additionally, the identifier article of the eighth aspect may include a near field communication (NFC) transponder that may emit the wireless ID signal in response to receipt of electromagnetic energy that may be emitted by the circuitry of the medical device.

If desired, after voice control of the medical device is enabled, voice inputs received by the microphone of the circuitry may be transmitted by the transmitter of the circuitry to the VCA computer. In this regard, the VCA computer may be configured to determine that the voice input may correspond to at least one valid control command for the medical device from among a plurality of valid control commands. If the voice input corresponds to a valid control command of the plurality of valid control commands, the VCA computer may be configured to transmit a device control message to the medical device. In response to receipt of the device control message by the circuitry of the medical device, the medical device may carry out a function corresponding to the device control message.

Optionally, after voice control of the medical device of the eighth aspect becomes enabled, the circuitry may be enabled for receiving voice commands to control functions of the medical device for a threshold period of time. After the threshold period of time elapses without the medical device of the eighth aspect receiving at least one voice command, the medical device may become disabled from voice control. It is contemplated by the present disclosure that, in response to receiving a valid voice command during the threshold period of time, the threshold period of time may reset.

According to a ninth aspect of the present disclosure, a system for voice control of medical devices in a room may include a first medical device that may have first circuitry that may include a first processor, first memory, and a first microphone, and a second medical device that may have second circuitry that may include a second processor, second memory, and a second microphone. The first and second medical devices of the ninth aspect may be in sufficiently close proximity to each other that a voice input spoken by a person may be received by both of the first and second microphones. The first circuitry of the first medical device may be configured to become enabled for voice control in response to the voice input received by the first microphone being louder than the voice input received by the second microphone. The second circuitry of the second medical device may be configured to become enabled for voice control in response to the voice input received by the second microphone being louder than the voice input received by the first microphone.

In some embodiments of the ninth aspect, the first circuitry may be configured to transmit a first loudness value for receipt by the second circuitry and the second circuitry may be configured to transmit a second loudness value for receipt by the first circuitry. The first medical device of the ninth aspect may be configured to become enabled for voice control in response to the first circuitry determining that the first loudness value is greater than the second loudness value. The second medical device of the ninth aspect may be configured to become enabled for voice control in response to the second circuitry determining that the second loudness value is greater than the first loudness value.

If desired, the system of the ninth aspect further may include at least one voice control authorization (VCA) computer that may be remote from the first and second medical devices and that may be communicatively coupled to the first and second medical devices. The first circuitry may be configured to transmit a first loudness value for receipt by the at least one VCA computer and the second circuitry may be configured to transmit a second loudness value for receipt by the at least one VCA computer. The VCA computer may be configured to transmit a first message to the first medical device which enables the first medical device for voice control in response to the VCA computer determining that the first loudness value is greater than the second loudness value. The VCA computer may be configured to transmit a second message to the second medical device which enables the second medical device for voice control in response to the VCA computer determining that the second loudness value is greater than the first loudness value.

Optionally, after each of the first and second medical devices of the ninth aspect becomes enabled for voice control, the respective first and second circuitry may be enabled for receiving voice commands to control functions of the respective first and second medical device for a threshold period of time. After the threshold period of time elapses without the respective first and second medical device of the ninth aspect receiving at least one voice command, the respective first and second medical device may become disabled from voice control. It is contemplated by the present disclosure that, in response to receiving a valid voice command during the threshold period of time, the threshold period of time may reset.

According to a tenth aspect of the present disclosure, a system for voice control of medical devices in a room includes a first medical device that may have first circuitry that may include a first processor and first memory, and a second medical device that may have second circuitry that may include a second processor and second memory. The system of the tenth aspect may also have an array of microphones that may be located in the room and that may be spaced apart from the first and second medical devices. The array of microphones may include a first microphone that may be closer to the first medical device than to the second medical device and a second microphone that may be closer to the second medical device than to the first medical device. The first and second medical devices of the tenth aspect may be in sufficiently close proximity to each other that a voice input spoken by a person may be received by both of the first and second microphones. The first circuitry of the first medical device of the tenth aspect may be configured to become enabled for voice control in response to the voice input received by the first microphone being louder than the voice input received by the second microphone. The second circuitry of the second medical device of the tenth aspect may be configured to become enabled for voice control in response to the voice input received by the second microphone being louder than the voice input received by the first microphone.

In some embodiments, the first microphone of the tenth aspect may be include in first microphone circuitry that may be configured to transmit a first loudness value for receipt by the first circuitry of the first medical device and by the second circuitry of the second medical device. The second microphone of the tenth aspect may be included in second microphone circuitry that may be configured to transmit a second loudness value for receipt by the first circuitry of the first medical device and by the second circuitry of the second medical device. The first medical device of the tenth aspect may be configured to become enabled for voice control in response to the first circuitry determining that the first loudness value is greater than the second loudness value. The second medical device of the tenth aspect may be configured to become enabled for voice control in response to the second circuitry determining that the second loudness value is greater than the first loudness value.

If desired, the array of microphones of the tenth aspect may include communication circuitry that may be coupled to the first and second microphones. The communication circuitry may be configured to determine a first loudness value based on a first loudness of the voice input received by the first microphone and a second loudness value based on a second loudness of the voice input received by the second microphone. The communication circuitry may be configured to transmit the first and second loudness values for receipt by the first circuitry of the first medical device and by the second circuitry of the second medical device. The first medical device of the tenth aspect may be configured to become enabled for voice control in response to the first circuitry determining that the first loudness value is greater than the second loudness value. The second medical device of the tenth aspect may be configured to become enabled for voice control in response to the second circuitry determining that the second loudness value is greater than the first loudness value.

Optionally, the system of the tenth aspect further may include at least one voice control authorization (VCA) computer that may be remote from the first and second medical devices and that may be communicatively coupled to the first and second microphones of the array of microphones. The VCA computer may receive a first loudness value that may be based on a first loudness of the voice input received by the first microphone and a second loudness value that may be based on a second loudness of the voice input received by the second microphone. The VCA computer may be configured to transmit a first message to the first medical device which enables the first medical device for voice control in response to the VCA computer determining that the first loudness value is greater than the second loudness value. The VCA computer may be configured to transmit a second message to the second medical device which enables the second medical device for voice control in response to the VCA computer determining that the second loudness value is greater than the first loudness value.

Further optionally, after each of the first and second medical devices of the tenth aspect becomes enabled for voice control, the respective first and second circuitry may be enabled for receiving voice commands to control functions of the respective first and second medical device for a threshold period of time. After the threshold period of time elapses without the respective first and second medical device receiving at least one voice command, the respective first and second medical device of the tenth aspect becomes disabled from voice control. It is contemplated by the present disclosure that, in response to receiving a valid voice command during the threshold period of time, the threshold period of time may reset.

According to an eleventh aspect of the present disclosure, a system for voice control of medical devices in a room may include a first medical device that may have first circuitry that may include a first processor, first memory, a first microphone, and a first camera, and a second medical device that may have second circuitry that may include a second processor, second memory, a second microphone, and a second camera. The first circuitry of the first medical device of the eleventh aspect may be configured to become enabled for voice control in response to the first processor recognizing a first image of a face of a person as captured by the first camera. The second circuitry of the second medical device of the eleventh aspect may be configured to become enabled for voice control in response to the second processor recognizing a second image of the face of the person as captured by the second camera.

In some embodiments of the eleventh aspect, the first camera may capture the first image of the person for processing by the processor in response to the first microphone receiving a voice command from the person and the second camera may capture the second image of the person for processing by the processor in response to the second microphone receiving the voice command from the person. The voice command may include any valid device control command from among a plurality of valid device control commands, for example.

Optionally with regard to the eleventh aspect, the first circuitry of the may include a first display screen and the second circuitry may include a second display screen. If the first and second cameras both capture the respective first and second images of the face of the person in response to the voice commands, the first and second medical devices both may remain disabled from voice control and the first and second display screens each may display a notification message advising the person to face only the first or second camera of the respective first or second medical device that the person wishes to control by voice.

In some embodiments of the eleventh aspect, the first medical device may comprise a first patient bed that may have a first patient egress barrier to which the first camera may be coupled and the second medical device may comprise a second patient bed that may have a second patient egress barrier to which the second camera is coupled. For example, the first and second patient egress barriers each may include a respective first and second headboard or a respective first and second footboard. Thus, the first and second patient egress barriers each may comprise a respective first and second siderail. In such embodiments, the first circuitry further may include a first display screen coupled to the first siderail, the second circuitry further may include a second display screen coupled to the second siderail, the first camera may be situated adjacent the first display screen, and the second camera may be situated adjacent the second display screen.

If desired, the system of the eleventh aspect further may include at least one voice control authorization (VCA) computer that may be remote from the first and second medical devices and that may be communicatively coupled to the first and second medical devices. The first circuitry may be configured to transmit the first image for receipt by the at least one VCA computer and the second circuitry may be configured to transmit the second image for receipt by the at least one VCA computer. The VCA computer of the eleventh aspect may be configured to transmit a first message to the first medical device which enables the first medical device for voice control in response to the VCA computer determining that the person may be authorized to operate the first medical device by voice control based on analyzing the first image. The VCA computer may be configured to transmit a second message to the second medical device which enables the second medical device for voice control in response to the VCA computer determining that the person may be authorized to operate the second medical device by voice control based on analyzing the second image.

Optionally, after each of the first and second medical devices becomes enabled for voice control, the respective first and second circuitry may be enabled for receiving voice commands to control functions of the respective first and second medical device for a threshold period of time. After the threshold period of time elapses without the respective first and second medical device of the eleventh aspect receiving at least one voice command, the respective first and second medical device may become disabled from voice control. It is contemplated by the present disclosure that, in response to receiving a valid voice command during the threshold period of time, the threshold period of time may reset.

According to a twelfth aspect of the present disclosure, a system for voice control may include a medical device that may have first circuitry that may include a processor, memory, a button, and a microphone. The circuitry of the medical device of the twelfth aspect may be configured to become enabled for voice control in response to the button being selected by a person and then, thereafter, receiving a valid voice input via the microphone within a threshold period of time.

In some embodiments of the twelfth aspect, the valid voice input may include a code word. For example, the code word may include a first unique name that may correspond to the medical device and that may be received by the microphone within the threshold period of time. Optionally, the unique name may comprise a model name of the medical device.

If desired, after the medical device of the twelfth aspect becomes enabled for voice control, the respective circuitry may be enabled for receiving voice commands to control functions of the medical device for a second threshold period of time. After the second threshold period of time elapses without the medical device receiving at least one voice command, the medical device may be become disabled from voice control. It is contemplated by the present disclosure that, in response to receiving a valid voice command during the second threshold period of time, the threshold period of time may reset.

In some embodiments of the twelfth aspect, the valid voice input may include any device control command from among a plurality of device control commands. The present disclosure contemplates that the medical device may remain disabled from being voice controlled if the valid voice input is not received within the threshold period of time.

According to a thirteenth aspect of the present disclosure, a system for voice control of medical devices in a room may include a first medical device that may have first circuitry that may include a first processor, first memory, a first microphone, and a first infrared (IR) receiver, and a second medical device that may have second circuitry that may include a second processor, second memory, a second microphone, and a second IR receiver. The system of the thirteenth aspect may further include an IR pointer that may have an IR transmitter. The first circuitry of the first medical device may be configured to become enabled for voice control in response to the first IR receiver receiving an IR signal from the IR transmitter of the IR pointer. The second circuitry of the second medical device may be configured to become enabled for voice control in response to the second IR receiver receiving the IR signal from the IR transmitter of the IR pointer.

In some embodiments of the thirteenth aspect, the IR pointer may be configured to be worn on a finger of a person. Alternatively or additionally, the IR pointer may be mountable to a mobile phone. Further alternatively or additionally, the IR pointer may have a shape of a handwriting pen. Still further alternatively or additionally, the IR pointer may have a shape of a key fob.

It is contemplated by the present disclosure that the first medical device of the thirteenth aspect may comprise a first patient bed that may have a first patient egress barrier to which the first IR receiver may be coupled and the second medical device of the thirteenth aspect may comprise a second patient bed that may have a second patient egress barrier to which the second IR receiver may be coupled. For example, the first and second patient egress barriers each may comprise a respective first and second headboard or a respective first and second footboard. Alternatively or additionally, the first and second patient egress barriers each may comprise a respective first and second siderail. In such embodiments, the first circuitry further may include a first display screen coupled to the first siderail, the second circuitry further may include a second display screen coupled to the second siderail, the first IR receiver may be situated adjacent the first display screen, and the second IR receiver may be situated adjacent the second display screen.

If desired, after each of the first and second medical devices of the thirteenth aspect becomes enabled for voice control, the respective first and second circuitry may be enabled for receiving voice commands to control functions of the respective first and second medical device for a threshold period of time, and after the threshold period of time elapses without the respective first and second medical device receiving at least one voice command, the respective first and second medical device may become disabled from voice control. It is contemplated by the present disclosure that, in response to receiving a valid voice command during the threshold period of time, the threshold period of time may reset.

According to a fourteenth aspect of the present disclosure, a system for voice control of medical devices in a room may include a plurality of medical devices that may be in the room, an array of far-field microphones that may be dispersed throughout the room, and at least one computer that may be communicatively coupled to the plurality of medical devices and to the array of far-field microphones. The at least one computer may be configured to (i) combine voice inputs that may be received from a person by the array of far-field microphones, (ii) amplify and discern the voice inputs using beam-forming software, (iii) filter out ambient noise using barge-in software, (iv) execute speech recognition software to determine which medical device of the plurality of medical devices may be a designated medical device to be controlled by the voice inputs, and (v) transmit a control message to the designated medical device to control a first function of the designated medical device based on the voice inputs.

In some embodiments of the fourteenth aspect, each medical device of the plurality of medical devices may carry at least one far-field microphone of the array of far-field microphones. Optionally, the plurality of medical devices may include two or more of the following: a vital signs monitor, a patient bed, a headwall interface, a caregiver badge, a locating tag, a patient identification (ID) bracelet, a patient gown, an audio station of a nurse call system, a patient lift, and a chair. The speech recognition software of the fourteenth aspect may include one or more of the following: speech-to-text conversion software, code word recognition software, wake word recognition software, and natural language processing (NLP) software.

Optionally, the at least one computer of the fourteenth aspect further may be configured with distance processing software that may be executed to determine which far-field microphone of the array of far-field microphones may be a closest far-field microphone to the person and to determine which medical device of the plurality of medical devices may be nearest to the closest far-field microphone. Further optionally, the barge-in software may determine the ambient noise to filter out based on a signature or frequency of noise that may persist for a threshold period of time (e.g., longer than an amount of time that it takes to speak voice inputs).

If desired, the at least one computer of the fourteenth aspect further may be configured with speaker recognition software to determine an identification (ID) of the person that may be providing the voice inputs. In this regard, the speaker recognition software may include one or more of the following: Markov models software, pattern recognition software, voice biometrics software, neural network software, natural language processing (NLP) software, natural language understanding software, and Anaphora resolution software.

In some embodiments of the fourteenth aspect, the at least one computer further may be configured to determine that the voice inputs may include a compound voice command that may pertain to the designated medical device and to a second designated medical device. In such instances, the at least one computer further may be configured to transmit a second control message to the second designated medical device to control a second function of the second designated medical device based on a portion of the voice inputs pertaining to the second medical device. The at least one computer of the fourteenth aspect further may be configured to determine that the voice inputs may include a compound voice command that may pertain to the first function and to a second function of the designated medical device. In such instances, the control message transmitted by the at least one computer to the designated medical device may include a first portion to control the first function of the designated medical device and a second portion to control the second function of the designated medical device.

According to a fifteenth aspect of the present disclosure, a patient bed may include a frame that may be configured to support a patient, an array of far-field microphones that may be carried by the frame, and circuitry that may be carried by the frame and that may be coupled to the array of far-field microphones. The circuitry of the fifteenth aspect may include a processor and memory. Furthermore, the circuitry of the fifteenth aspect may be configured to (i) combine voice inputs that may be received from a person by the array of far-field microphones, (ii) amplify and discern the voice inputs using beam-forming software, (iii) filter out ambient noise using barge-in software, (iv) execute speech recognition software to determine a first function of the patient bed that may be to be carried out based on the voice inputs, and (v) control the patient bed to carry out the first function.

In some embodiments of the fifteenth aspect, the patient bed may include a plurality of barriers that may be coupled to the frame and each barrier of the plurality of barriers may carry at least one far-field microphone of the array of far-field microphones. Optionally, the speech recognition software of the fifteenth aspect may include one or more of the following: speech-to-text conversion software, code word recognition software, wake word recognition software, and natural language processing (NLP) software. Further optionally, the barge-in software of the fifteenth aspect may determine the ambient noise to filter out based on a signature or frequency of noise that may persist for a threshold period of time (e.g., longer than an amount of time that it takes to speak voice inputs).

If desired, the circuitry of the fifteenth aspect further may be configured with speaker recognition software to determine an identification (ID) of the person that may be providing the voice inputs. In this regard, the speaker recognition software of the fifteenth aspect may include one or more of the following: Markov models software, pattern recognition software, voice biometrics software, neural network software, natural language processing (NLP) software, natural language understanding software, and Anaphora resolution software. In some embodiments of the fifteenth aspect, the circuitry further may be configured to determine that the voice inputs may include a compound voice command that may pertain to the first function and to a second function of the patient bed. In such instances, the circuitry of the fifteenth aspect may be configured to control the second function of the patient bed concurrently with controlling the first function. Optionally, the circuitry of the fifteenth aspect may be configured to control functions of the patient bed in accordance with one or more rows (excluding the header row) provided in Table 1 which is set forth below in the present application. The patient beds of any of the first through fourteenth aspects may also be controlled with voice inputs in accordance with one or more rows (excluding the header row) provided in Table 1, if desired.

According to a sixteenth aspect of the present disclosure, a system for voice control of a patient room environment may be provided. The system of the sixteenth aspect may include an environment device that may be operable to control the patient room environment, an entertainment device that may be operable to provide entertainment to a patient in the patient room, and a microphone that may be situated in the patient room and that may be configured to receive voice control commands from the patient for controlling the environment device and the entertainment device. The system of the sixteenth aspect may also include a remote computer that may be communicatively coupled to the microphone and that may have voice recognition software. The remote computer of the sixteenth aspect may be configured to process the voice control commands and to send control messages to control the operation of the environment device and the entertainment device.

In some embodiments of the sixteenth aspect, the environment device may include one or more of the following: a motorized window blind, a motorized curtain, a room light, a reading light, or a thermostat. The entertainment device of the sixteenth aspect may include a television. Alternatively or additionally, the entertainment device of the sixteenth aspect may include a speaker unit that may be configured to play audio of recorded books, voice-based games, and trivia. Optionally, the microphone of the sixteenth aspect may be included in the speaker unit. Further optionally, the system of the sixteenth aspect further may include a patient bed that may be configured to support the patient and the speaker unit may be included in the patient bed.

If desired, the entertainment device of the sixteenth aspect may include a second entertainment device that may be spaced from the speaker unit and the control messages to control the operation of the environment device and the second entertainment device may be routed to the environment device and the second entertainment device through the speaker unit. It is contemplated by the present disclosure that the control messages of the sixteenth aspect may be received by the speaker unit as wireless control messages. Alternatively or additionally, the control messages sent to the environment device and the second entertainment device from the speaker unit may be transmitted wirelessly.

According to a seventeenth aspect of the present disclosure, a system for voice control of a patient room environment may be provided. The system of the seventeenth aspect may include an environment device that may be operable to control the patient room environment, an entertainment device that may be operable to provide entertainment to a patient in the patient room, and a microphone that may be situated in the patient room and that may be configured to receive voice control commands from the patient for controlling the environment device and the entertainment device. The system of the seventeenth aspect may also include an Internet of Things (IoT) hub that may be communicatively coupled to the microphone. The microphone of the seventeenth aspect may be configured to transmit the voice control commands to the IoT hub and the IoT hub may be configured to transmit control messages to control operation of the environment device and the entertainment device.

In some embodiments of the seventeenth aspect, the environment device may include one or more of the following: a motorized window blind, a motorized curtain, a room light, a reading light, or a thermostat. The entertainment device of the seventeenth aspect may include a television. Alternatively or additionally, the entertainment device of the seventeenth aspect may include a speaker unit that may be configured to play audio of recorded books, voice-based games, and trivia. Optionally, the microphone of the seventeenth aspect may be included in the speaker unit. Further optionally, the system of the seventeenth aspect further may include a patient bed that may be configured to support the patient and the speaker unit may be included in the patient bed.

If desired, the entertainment device of the seventeenth aspect may include a second entertainment device that may be spaced from the speaker unit and the control messages from the IoT hub to control the operation of the environment device and the second entertainment device may be routed to the environment device and the second entertainment device via the speaker unit. It is contemplated by the present disclosure that at least some of the control messages of the seventeenth aspect may be received by the speaker unit from the IoT hub as wireless control messages. Alternatively or additionally, the control messages of the seventeenth aspect sent to the environment device and the second entertainment device from the speaker unit may be transmitted wirelessly.

In some embodiments, the system of the seventeenth aspect further may include a second environment device, a second entertainment device, and a remote computer that may be communicatively coupled to the microphone and having voice recognition software. The remote computer may be configured to process the voice control commands and to send second control messages to control the operation of the second environment device and the second entertainment device. Optionally, the second control messages may be transmitted to the second environment device and the second entertainment device without involving the IoT hub. Further optionally, the system of the seventeenth aspect further may include a speaker unit, the microphone may be included in the speaker unit, and the second control messages may be transmitted to the second environment device and the second entertainment device though the speaker unit.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIG. 7 is a flow chart of a voice model algorithm showing that a caregiver uses an application on a mobile device to create a voice model which is pushed to a device such as the patient bed and the application on the mobile phone updates the voice model to improve accuracy;

FIG. 8 is a flow chart of a caregiver authorization algorithm that is used to confirm that a caregiver providing voice inputs to the patient is authorized to do so;

DETAILED DESCRIPTION

Figure 1:
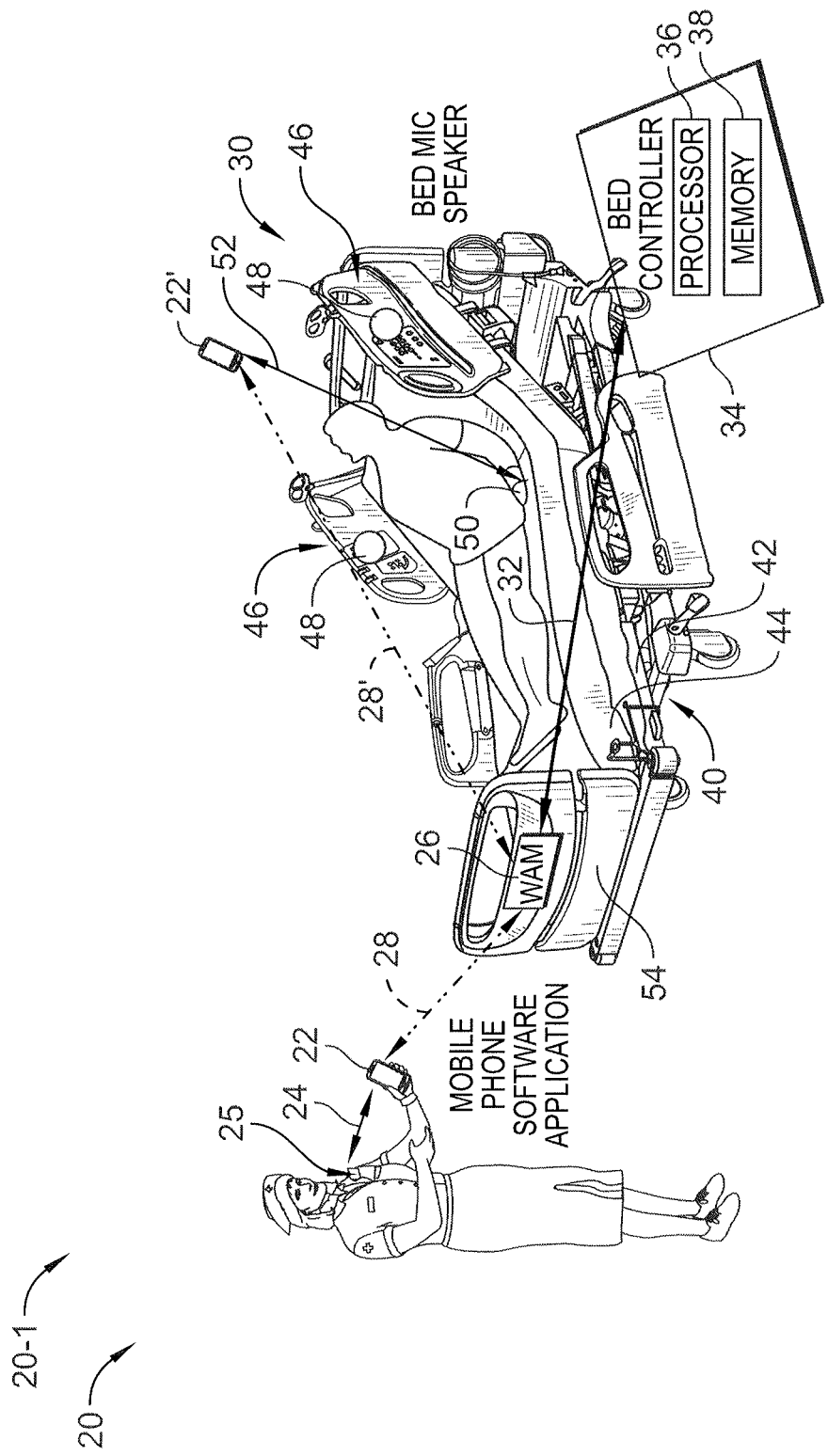
FIG. 1 is a diagrammatic view of a first voice control system showing a caregiver entering voice inputs on a mobile phone for control of a patient bed supporting a patient, the mobile phone communicating wirelessly with a wireless access module (WAM) of the patient bed, the WAM communicating bed messages corresponding to the voice inputs via a wired connection to a bed controller of the patient bed, the patient bed having a microphone and speaker on each of a pair of siderails as indicated diagrammatically by circles on the siderails, and a patient mobile phone shown above the patient's head for use by the patient to enter voice inputs to the WAM of the patient bed.
Figure 2:
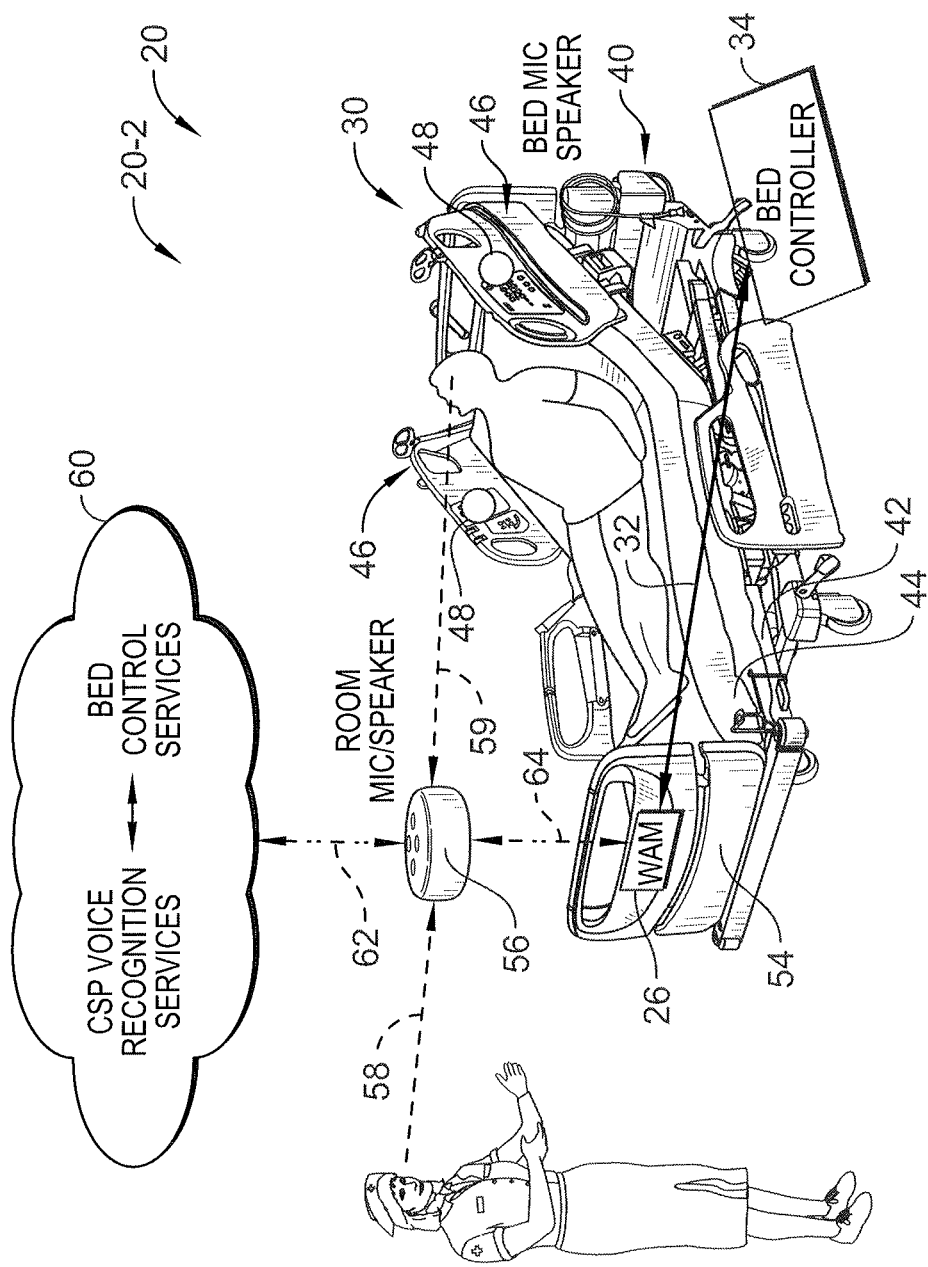
FIG. 2 is a diagrammatic view of a second voice control system, similar to FIG. 1, showing a room microphone and speaker unit above a footboard of the patient bed, the room microphone and speaker unit being in wireless communication with the WAM of the patient bed, the room microphone and speaker unit being configured to receive voice inputs from the caregiver and the patient, and the room microphone and speaker unit being in communication with a network having Continuous Speech Processing (CSP) voice recognition services and bed control services provided by software of one or more servers of the network so that the one more severs are able to process the voice inputs and provide command messages to the WAM of the patient bed via the room microphone and speaker unit to control functions of the patient bed.

A system 20 for voice control of equipment in a healthcare facility is shown in each of FIGS. 1-6 and 9-14 of the present disclosure. Flow charts pertaining to algorithms for voice control of the equipment of system 20, as contemplated herein, are shown in FIGS. 7, 8 and 15. With regard to system 20, various embodiments are disclosed, and so hyphenated suffixes are added to reference number 20 for each of the systems 20 of FIGS. 1-6 and 9-14. The hyphenated suffixes correspond to the FIG. number of the particular system 20 embodiment. For example, system 20 of FIG. 1 is designed with reference number 20-1, the system 20 of FIG. 2 is designated with reference number 20-2, and so forth. It should be appreciated that the systems 20 of FIGS. 1-6 and 9-14 are not mutually exclusive such that a system having combinations of any two or more of systems 20-1, 20-2, 20-3, 20-4, 20-5, 20-6, 20-9, 20-10, 20-11, 20-12, 20-13, 20-14 are within the scope of the present disclosure. Furthermore, the algorithms corresponding to the flow charts of FIGS. 7, 8 and 15 may be implemented in any one or more of systems 20-1, 20-2, 20-3, 20-4, 20-5, 20-6, 20-9, 20-10, 20-11, 20-12, 20-13, 20-14 as well as combinations thereof.

Referring now FIG. 1, first voice control system 20-1 is configured to permit a caregiver to enter voice inputs on a caregiver mobile phone 22 for control of a patient bed 30 supporting a patient. The caregiver wears or otherwise carries a caregiver identification (ID) badge or tag 25 which provides a wireless signal, indicated diagrammatically in FIG. 1 by a double headed arrow 24, to mobile phone 22. The wireless signal 24 from caregiver badge 25 includes a caregiver ID (e.g., caregiver's employee number, a randomly assigned number, the caregiver's name, or the like). The mobile phone 22 transmits a query message to the caregiver badge 25 and the badge 25 responds to the query message by transmitting the caregiver ID to the mobile phone 22. In some embodiments, the query message from phone 22 is initiated in response to the caregiver providing a voice input to the mobile phone 22 pertaining to control of bed 20. Thus, the wireless link 24 between mobile phone 22 and badge 25 is bidirectional in the illustrative embodiment.

The mobile phone 22 communicates wirelessly with a wireless access module (WAM) 26 of patient bed 30 as indicated diagrammatically in FIG. 1 by dashed double-headed arrow 28. In some embodiments, the voice inputs from the caregiver are converted by mobile phone 22 into wireless bed command messages 28 that are transmitted wirelessly to WAM 26 along with the caregiver ID. Wireless messages 28, such as acknowledgement messages, alert messages, and the like are also communicated as appropriate from WAM 26 to mobile phone 22. Thus, the wireless link 28 between mobile phone 22 and WAM 26 is bidirectional. In other embodiments, a voice recording is made by phone 22 and converted to a digital sound file (e.g., .wav file) that is transmitted wirelessly to WAM 26 via wireless link 28. The caregiver ID is also transmitted to WAM 26 wirelessly along with the digital sound file. In some such embodiments, WAM 26 converts the digital sound file into one or more bed command messages.

After receiving the bed command message(s), or digital sound file(s), via wireless link 28 along with the caregiver ID from mobile phone 22, WAM 26 communicates the bed command messages corresponding to the voice inputs from the caregiver along with the caregiver ID via a wired link or connection indicated diagrammatically in FIG. 1 by doubled headed arrow 32 to a bed controller 34. Controller 34 then determines if the caregiver ID matches an ID stored in memory of the controller 34. If the ID's match, then the controller 34 concludes that the caregiver is authorized to operate bed 30 by voice and carries out the bed function to which the bed command message pertains. In other embodiments, bed controller 34 is configured to determine caregiver authorization for voice control by other methodologies as will be described below in further detail.

Bed controller 34 is represented diagrammatically as a single block in FIG. 1, but bed controller 34 in some embodiments, comprises various circuit boards, electronics modules, and the like that are electrically and communicatively interconnected. Thus, bed controller includes a processor 36, such as one or more microprocessors or microcontrollers that execute software to perform the various control functions and algorithms described herein. Thus, bed controller 34 also includes memory 38 for storing software, variables, calculated values, and the like as is well known in the art. The bed controller 34 may, therefore, include or be embodied as any device or circuitry (e.g., a processor, a microcontroller, a field programmable gate array (FPGA), an application specific integrated circuit (ASIC), reconfigurable circuitry, System on Chip (SoC), Programmable System on Chip (PSoC), Computer on Module (CoM), and System on Module (SoM), etc.) and/or software configured to operate the bed 30 as described herein. In some embodiments, bed controller 34 includes a model no. VAR-SOM-MX6 System on Module (SoM) available from Variscite Ltd. of Lod, Israel that serves as or is provided on a Master Control Board (MCB) of bed 20.

In the illustrative examples of FIGS. 1-6 and 9-14, each bed 30 is depicted as a CENTRELLA® Smart+bed available from Hill-Rom Company, Inc. Additional details of the CENTRELLA® Smart+bed 30, and variants thereof, can be found in U.S. Pat. No. 10,517,784 which is hereby incorporated by reference herein to the extent not inconsistent with the present disclosure which shall control as to any inconsistencies. Although the present disclosure is focused, in large part, on voice control of illustrative bed 30, it should be appreciated that the present disclosure is applicable to voice control of all types of medical equipment or devices, including other models of patient beds (e.g., the PROGRESSA® bed, VERSACARE® Med Surg bed, ENVELLA® air fluidized therapy bed, COMPELLA® bariatric bed, ADVANTA™ 2 Med Surg bed, EXCEL CARE ES® bariatric bed, AFFINITY® 4 birthing bed, and TOTALCARE® bed available from Hill-Rom Company, Inc., just to name a few, and beds of other manufacturers); patient monitors (e.g., heart rate monitors, respiration rate monitors, electrocardiographs (EKG's), electroencephalographs (EEG's), pulse oximeters, blood pressure monitors, and thermometers); drug delivery devices such as drug infusion pumps; intravenous (IV) devices; ventilators; respiratory therapy devices such as devices for oscillatory lung expansion (OLE), insufflation/exsufflation, continuous positive expiratory pressure (CPEP), continuous high frequency oscillation (CHFO), continuous positive airway pressure (CPAP), Bi-PAP, and the like; compression therapy devices for treating deep vein thrombosis (DVT) including sequential compression devices (SCD's); and the like.

Referring once again to FIG. 1, patient bed 30 has a frame 40 including an articulated patient support deck 42 supporting a mattress 44. A head end siderail 46 is coupled to each side of a head section of deck 42 such that bed 30 has two head end siderails 46. A microphone (mic) and speaker are carried by each of siderails 46 as indicated diagrammatically by circles 48 on the siderails 46. The speaker and mic 48 on each siderail 46 may be included in a single unit which is referred to herein sometimes as a "speaker unit" even though a mic is also included in the unit. Alternatively, the microphone and speaker of each siderail 46 are separate components included in the circuitry of the respective siderail 46 in some embodiments. Further alternatively, in some embodiments, the speaker itself also serves as a mic that is capable of receiving voice inputs. The mics 48 of bed 30 are each capable of receiving voice inputs from either the caregiver or the patient supported on bed 30.

In FIG. 1, a patient mobile phone 22' is shown diagrammatically above the patient's head. The patient mobile phone 22' may be used by the patient in addition to, or in lieu of, mics 48 to enter voice inputs to the WAM 26 of the patient bed as indicated diagrammatically by dashed double headed arrow 28'. Acknowledgement messages, alert messages, and the like are provided to mobile phone 22' via wireless link 28' under appropriate circumstances. In the illustrative example of FIG. 1, a patient identification (ID) wrist band 50 is worn by the patient and provides a wireless signal 52, indicated diagrammatically in FIG. 1 by a double headed arrow, to mobile phone 22'. The wireless signal 52 from wrist band 50 includes a patient ID (e.g., patient's medical record number (MRN), a randomly assigned number, the patient's name, or the like). Mobile phone 22' includes the patient ID in the wireless transmission 28' to WAM 26 of bed 30 and the WAM 26 transmits the patient ID to bed controller 34 along with the bed command message. Controller 34 then determines if the patient ID matches an ID stored in memory 36. If the ID's match, then the controller 34 concludes that the patient is authorized to operate bed 30 by voice and carries out the bed function to which the bed command message pertains.

In FIG. 1, WAM 26 is shown diagrammatically as being coupled to a footboard 54 of bed 30 and bed controller 34 is shown in a block adjacent to bed 30. While it is possible for WAM 26 to be carried by or otherwise included in footboard 54 of bed 30, in typical embodiments of bed 30 contemplated herein, WAM 26 and bed controller 34 are carried by frame 40 of bed 30. In fact, WAM 26 and bed controller 34 may be included on the same printed circuit board if desired. Furthermore, WAM 26 may be implemented as part of the processor 36 and memory 38 (e.g., microcontroller, SoM, SoC, PSoC, FPGA, or ASIC) of bed controller 34 in some embodiments.

Based on the foregoing, it should be appreciated that, in the embodiment of FIG. 1, the controller 34 of bed 30 determines that the caregiver or the patient is authorized to control functions of bed 30 by voice based on an on-bed analysis of the caregiver ID from badge 25 or the patient ID from wrist band 50, respectively. Thus, the ID's of one or more caregivers and/or one or more patients who are authorized to control bed 30 by voice are stored in memory 38 of bed 30 prior to receipt of voice inputs from the caregiver or patient via mobile phones 22, 22' and/or mics 48 of bed 20. Such ID's are uploaded to memory 38 of bed controller 34 from a remote computer such as an electronic medical record (EMR) computer, an admission-discharge-transfer (ADT) computer, a nurse call computer, a workflow computer, or the like that is communicatively coupled to bed controller 34 via a network of the healthcare facility.

After the patient is discharged from the healthcare facility or re-assigned to a different bed, the remote computer transmits a clear signal to bed controller 34 which results in the bed controller 34 clearing the patient ID from memory 38 or otherwise designating the patient ID as no longer corresponding to a patient who is authorized to control bed 30 by voice. Similar clear messages are sent to bed controller in connection with caregivers who are no longer authorized to control bed 30 by voice for whatever reason, such as the caregiver being re-assigned to a different ward of the healthcare facility, the caregiver no longer being employed by the healthcare facility, the caregiver's shift ending, or the like.

In the illustrative FIG. 1 embodiment of system 20-1, phones 22, 22' are each equipped with transceivers for communication with tags 25 and wristbands 50. In such embodiments, bed 30 does not need to be equipped with any sort of reader or transceiver for communicating with tags 24 and wristbands 50 since this functionality is provided by mobile phones 22, 22'. In other embodiments, bed 30 includes a transceiver or reader for communication with tags 25 and wristbands 50 in addition to, or in lieu of, the tag/band communication functionality of mobile phones 22, 22'.

In some embodiments of system 20-1, either or both of mobile phones 22, 22' are equipped with a bed control software application that presents bed control inputs on the touchscreen displays of the respective mobile phones 22, 22'. In such embodiments, the caregiver or patient, as the case may be, selects the buttons or other user inputs presented on the display screen of the respective mobile phone 22, 22' to control the corresponding bed function. In response to selection of the bed control input on phone 22, 22', bed command messages are transmitted from the phone 22, 22' to WAM 26 via the respective wireless link 28, 28' and are processed by WAM 26 and bed controller 34 to control the bed functions corresponding to the bed command messages. In some embodiments in which manual inputs are provided to bed 30 via phones 22, 22', no caregiver or patient authorization algorithm is implemented by bed 30. That is, any bed control messages received at WAM 26 in such embodiments are assumed to be originating from phones 22, 22' of users who are authorized to control functions of bed 30. Optionally, the bed control application on phones 22, 22' may require entry of a personal identification number (PIN) on the respective phone 22, 22' before launching the bed control application for use by the respective caregiver or patient. Requiring entry of a PIN on phones 22, 22' provides some level of assurance that the respective caregiver or patient is authorized to control bed 22 with the respective phone 22, 22'.

Referring now to FIG. 2, a second voice control system 20-2, similar to system 20-1 of FIG. 1, is provided. System 20-2 includes bed 30 having WAM 26, bed controller 34, and mics and speakers 48 coupled to siderails 46 and so the descriptions above of these components and other portions of bed 30 are equally applicable to system 20-2 and are not repeated. However, in lieu of mobile phones 22, 22' of system 20-1, system 20-2 has a room microphone (mic) and speaker unit 56 that receives voice inputs 58 from the caregiver and voice inputs 59 from the patient as shown diagrammatically in FIG. 2. Mic and speaker unit 56 is sometimes referred to herein as just "speaker unit 56." Speaker unit 56 is shown diagrammatically above footboard 54 of patient bed 30 in FIG. 2 but it should be appreciated that speaker unit 56 may be situated at any suitable location within the patient room. For example, speaker unit 56 may be placed on a nightstand adjacent to bed 30, mounted to a room wall or a ceiling of the room in which bed 30 is located, or even mounted to bed 30 itself. When speaker unit 56 or any other component is described herein as being mounted, fixed, or attached to a room wall, it is intended to mean that the component is mounted directly to the wall in the room, mounted to a headwall unit that is attached to a room wall adjacent a head end of bed 30, or mounted to some other architectural structure in the room such as a service chase, bed locator unit, or column that is attached to, or otherwise fixed in place relative to the wall of the room.

In some embodiments, speaker unit 56 and speaker units 48 cooperate to provide system 20-2 with an array of mics that receive voice inputs 56, 58 from the caregiver and patient, respectively. Speaker unit 56 is communicatively coupled to a network 60 of the healthcare facility via a bidirectional wireless link 62 as shown diagrammatically in FIG. 2. Speaker unit 56 is also in wireless communication with WAM 26 of patient bed 30 via a bidirectional wireless link 64. Network 60 is depicted diagrammatically as a cloud in FIG. 2. However, the diagrammatic cloud is intended to represent all components typically found in a network of a healthcare facility, for example, and so is intended to represent the infrastructure (e.g., wireless access points, Ethernet jacks such as RJ-45 connectors, wires, routers, gateways, etc.) provided in network 60 of the healthcare facility and the various computer devices (e.g., personal computers, servers, laptop computers, patient care equipment, etc.) that are coupled to the infrastructure.

As shown diagrammatically in FIG. 2, network 60 of system 20-2 provides Continuous Speech Processing (CSP) voice recognition services and bed control services to bed 30. In particular, the CSP voice recognition services and the bed control services are provided by software of one or more servers of network 60. Thus, voice inputs 58, 59 received by speaker unit 62 are transmitted via wireless link 62 to the one or more servers having the CSP voice recognition services and bed control services so that the one more severs are able to process the voice inputs and provide bed command messages to the WAM 26 of patient bed 30 via the room microphone and speaker unit 26 to control functions of patient bed 30.

In some instances of system 20-2, voice inputs from the caregiver or patient that are received by one or both of mics 48 of bed 30 are communicated to WAM 26, either directly via a wired connection, or through bed controller 34 and wired connection 32, and then are transmitted to speaker unit 56 via wireless link 64. Speaker unit 64, in turn, communicates messages corresponding to the voice inputs received initially at mics 48 to network 60 via wireless link 62 for processing by the server or servers having the CSP voice recognition services and bed control services. The server having the software that provides the CSP voice recognition services is sometimes referred to herein as a "voice control authorization (VCA) computer."

The voice inputs communicated over wireless links 62, 64 are digitized sound files such as .wav files. In other embodiments, other types of audio file formats may also be used in system 20 in addition to or in lieu of the .wav file format, including audio formats having the following file designator types: 0.3gp, .aa, .aac, .aax, .act, .aiff, .alac, .amr, .ape, .au, .awb, .dct, .dss, .dvf, .flac, .gsm, .iklax, .ivs, .m4a, .m4b, .m4p, .mmf, .mp3, .mpc, .msv, .nmf, .ogg, .oga, .mogg, .opus, .ra, .rm, .raw, .rf64, .sln, .tta, .voc, .vox, .wma, .wv, .webm, 0.8svx, and .cda. Thus, WAM 26 and/or speaker unit 56 may employ various audio file compression techniques in connection with the digitized sound files that are transmitted to network 60 via either or both of wireless links 62, 64. In some embodiments, speaker unit 56 is an AMAZON® ECHO® unit or an AMAZON® ALEXA® unit.

In some embodiments, the VCA computer of network 60 stores a digital model of the voices of each of the caregivers and patients who are authorized to control the various medical devices, such as patient bed 30, that are located in the various patient rooms of the healthcare facility. After the voice input from the caregiver or patient attempting to control bed 30 is received at the VCA computer as a digital audio file, the digital audio file is compared by the VCA computer to the digital model of the voices of authorized users stored in memory of the VCA computer. If the digital audio file of the voice input matches one of the digital models of authorized users, then the VCA computer sends a bed control message to the server having the software that provides the bed control services (sometimes referred to herein as the "bed control computer"). The present disclosure contemplates that voice biometrics are used by the VCA computer in connection with comparing the audio files of voice inputs to the stored digital models.

The voice biometrics used by the VCA computer may involve, for example, feature extraction (e.g., determining tones, pitches, and/or frequencies of a person's voice); creation of voiceprints (e.g., spectrograms); use of any one or more of: frequency estimation, hidden Markov models, Gaussian mixture models, pattern matching methodologies, neural networks, matrix representation and decision trees; determining speech signal feature vectors such as by segmenting the speech signal into glottal pulses, computing a glottal pulse feature vector for each glottal pulse, and computing the speech signal feature vector as a function of the glottal pulse feature vectors; and other methodologies such as determining linear prediction coefficients from the speech signal, forming an inverse filter from the extracted linear prediction coefficients, filtering the speech signal using the inverse filter to obtain in inverse filtered signal, and segmenting the inverse filtered signal into glottal pulses. For additional details regarding voice biometrics, see U.S. Pat. Nos. 10,614,814; 9,870,776; and 8,620,666 which are each incorporated herein by reference in their entirety to the extent not inconsistent with the present disclosure which shall control as to any inconsistencies.

In some embodiments of system 20, the bed control message sent by the VCA computer to the bed control computer comprises one or more packets of data that encode text corresponding to the spoken voice input. The packets sent from the VCA computer to the bed control computer may include text in the .html format or .xml format, for example. The bed control computer then converts the text from the one or more packets of data into a digitized bed control message that is transmitted to bed 30 over network 60 resulting in the corresponding bed function being activated on bed 30. The bed control message may be sent from the bed control computer to bed 30 via wireless links 62, 64 and speaker unit 56 in some embodiments. In other embodiments, the bed control message from the bed control computer is routed to bed 30 by other infrastructure of network 60 such as one or more wireless access points or even via a nurse call system of network 60 that communicates with bed 30 via a wired connection (e.g., a 37-pin nurse call cable between bed 30 and a nurse call system interface unit, such as a network interface unit (NIU), audio station bed connector (ASBC), and the like that is mounted to a room wall) or via a wireless connection (e.g., a Bluetooth connection between bed 30 and a universal collector or other unit mounted to the room wall and having Bluetooth wireless communication capability).

In order for the VCA computer to know which bed 30 the voice input corresponding to the digital audio file is intended to control, a bed ID corresponding to the particular bed 30 and/or a location ID corresponding to the room in which bed 30 is located, is included with the digital audio file. The location ID may correspond to, or be associated with, a speaker unit ID of speaker unit 56. The speaker unit ID may be an assigned unique ID or may correspond to a media control access (MAC) address of the speaker unit 56, for example. Bed-to-room associations are stored in a database of network 60 such that each bed ID of beds 30 is associated with a particular room of the healthcare facility. The bed-to-room association database may be included in the VCA computer, the bed control computer, or some other computer such a locating server of a real time location system (RTLS) of the healthcare facility. A patient ID is also associated with the bed 30 and/or room in which bed 30 is located in some embodiments. Thus, the association database stores patient-to-bed and/or patient-to-room and/or patient-to-bed-to-room associations in some embodiments. In any event, when the bed control computer sends the bed command message, bed ID and/or speaker unit ID is included with the bed command message so that network 60 is able to route the bed command message to the appropriate bed 30 to be controlled.

Figure 3:
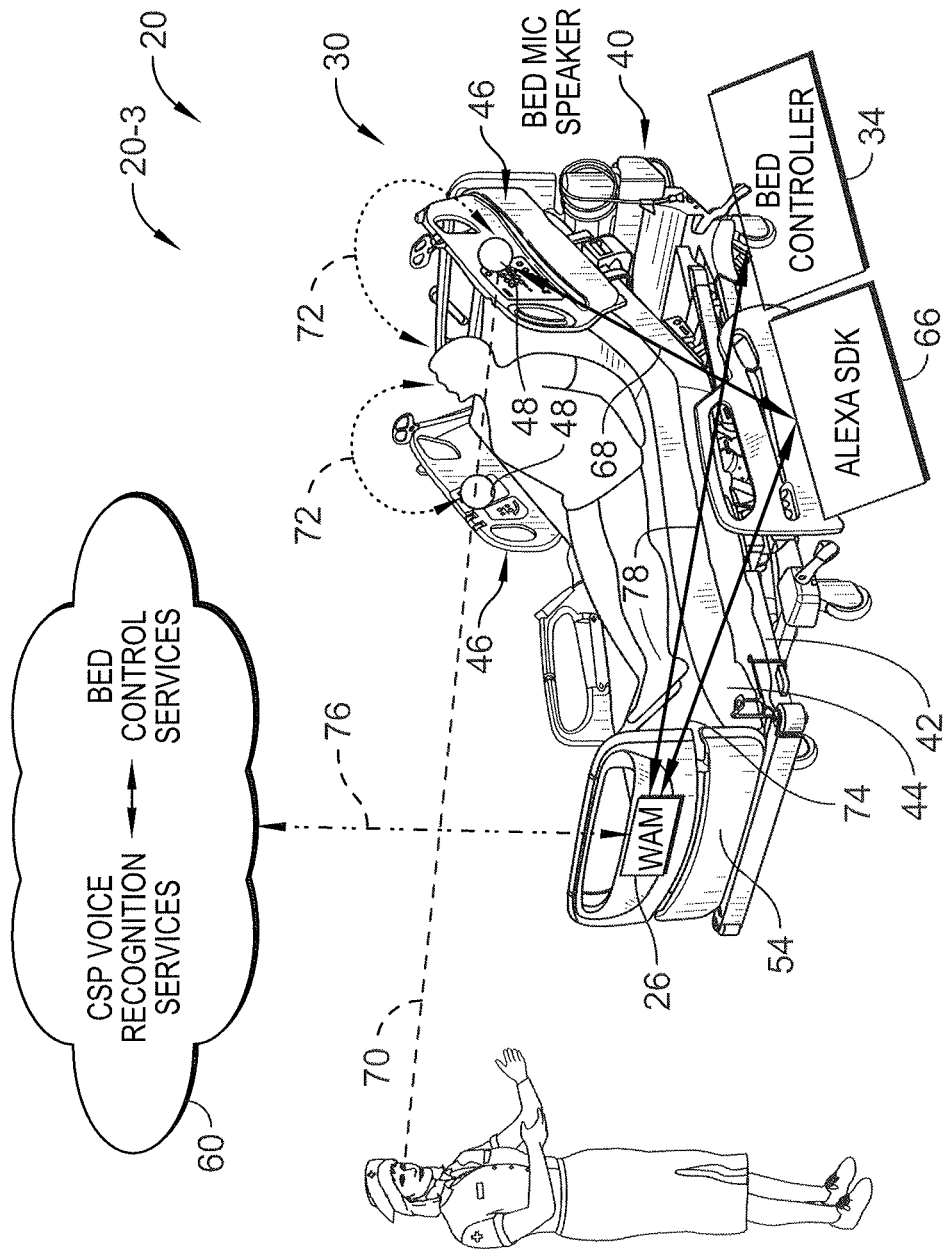
FIG. 3 is a diagrammatic view of a third voice control system, similar to FIGS. 1 and 2, showing the caregiver providing voice inputs to the microphone on one of the siderails of the patient bed, the patient bed having an ALEXA® software development kit (SDK) that interfaces with the WAM of the patient bed, and the WAM being in communication with a network having the CSP voice recognition services and bed control services provided by the software of one or more servers of the network so that the one more severs are able to process the voice inputs and provide command messages to the patient bed via the WAM to control functions of the patient bed.

Referring now to FIG. 3, a third voice control system 20-3, similar to systems 20-1, 20-2 of FIGS. 1 and 2, is provided. System 20-3 includes bed 30 and network 60 with the VCA computer having software implementing CSP voice recognition services and the bed control computer having software implementing bed control services. Thus, the descriptions above of bed 30 and network 60 in connection with systems 20-1, 20-2 is equally applicable to system 20-3 and so the descriptions are not repeated. In some embodiments of system 20, the VCA computer and the bed control computer are the same computer. That is, the CSP voice recognition services and the bed control services are provided by the same computer, such as the same server.

The main difference between system 20-3 and system 20-2 is that the voice processing functionality of speaker unit 56 of system 20-2 is included in bed 30 of system 20-3. In this regard and in connection with the illustrative FIG. 3 example, bed 30 has an ALEXA® software development kit (SDK) 66 that interfaces with WAM 26 of patient bed 30. The SDK, or more accurately stated, the circuitry of bed 30 implementing the SDK, is coupled to the mic and speaker units 48 on siderails 46 via wired connections 68 as shown diagrammatically in FIG. 3. Voice inputs 70 from the caregiver and voice inputs 72 from the patient are detected by one or both of microphones 48 and are provided to SDK 66 via wired link 68. In some embodiments, the microphones of speaker units 48 cooperate to provide system 20-3 with an array of mics that receive voice inputs 70, 72 from the caregiver and patient, respectively.

SDK 66 processes the voice inputs 70, 72 received from the microphone(s) 48 and provides voice messages (e.g., digital audio files) to WAM via wired communication link which, in turn, communicates the voice messages received from SDK 66 to the VCA computer of network 60 via a wireless communication link 76 as indicated diagrammatically in FIG. 3. The VCA computer of network 60 processes the digital audio files corresponding to the voice inputs 70, 72 by comparing them to digital models of voices of authorized users as described above. If the voice input(s) 70, 72 originated from an authorized user, the VCA computer coordinates with the bed control computer resulting in the bed control computer transmitting one or more bed command messages to patient bed 30 via wireless link 76 and WAM 26 to control functions of the patient bed. In this regard, the bed command messages are routed on bed 30 from the WAM 26 to bed controller 34 via a wired communication link or connector 78 as shown diagrammatically in FIG. 3.

Figure 4:
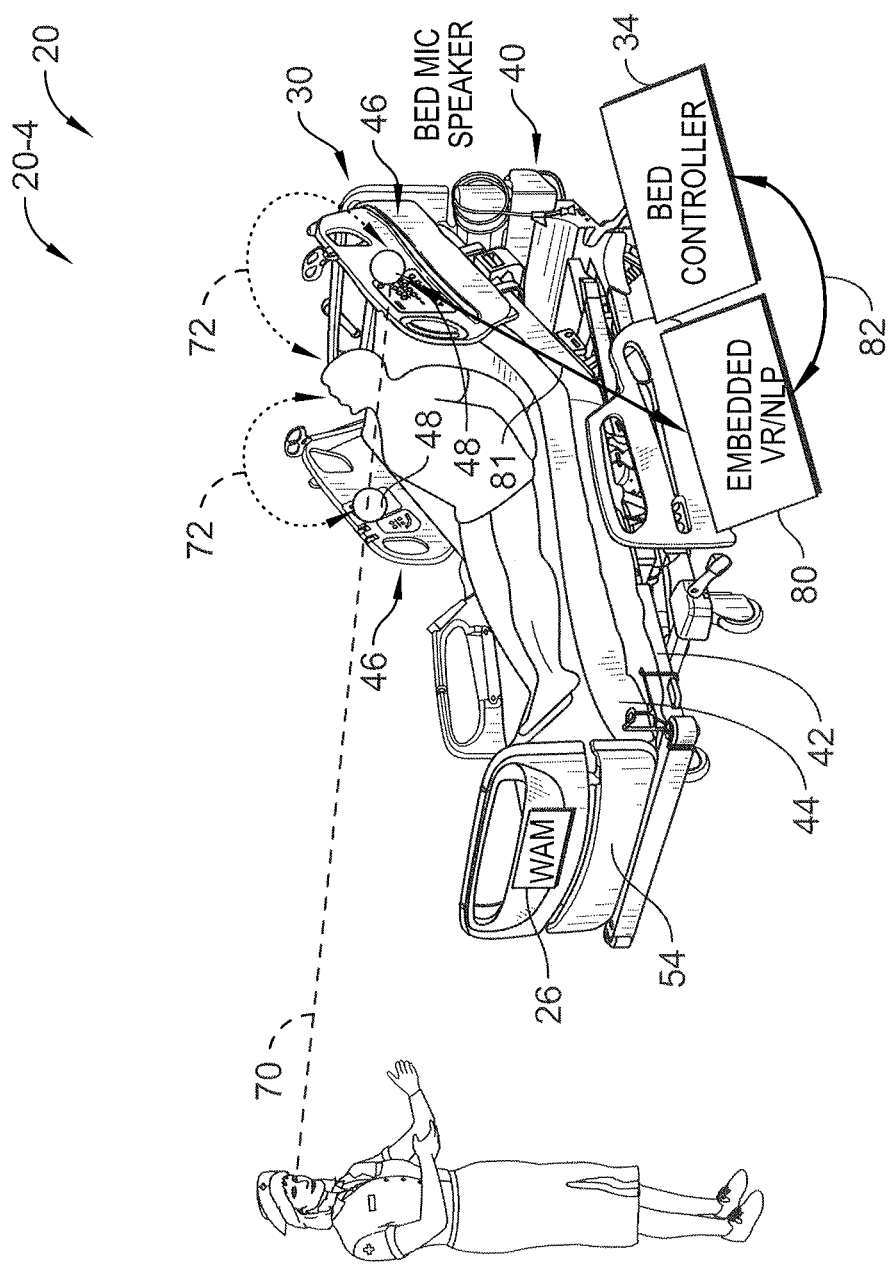
FIG. 4 is diagrammatic view of a fourth voice control system, similar to FIGS. 1-3, showing the caregiver providing voice inputs to the microphone on one of the siderails of the patient bed, the patient bed having circuitry with embedded voice recognition (VR) and natural language processing (NLP) software to convert the voice inputs into command messages that are communicated to the bed controller to control functions of the patient bed.

Referring now to FIG. 4, a fourth voice control system 20-4, similar to systems 20-1, 20-2, 20-3 of FIGS. 1-3, is provided. Therefore, portions of system 20-4 that are substantially the same as those of systems 20-1, 20-2, 20-3 are indicated with like reference numbers and the descriptions are not repeated. Thus, the descriptions above of portions of system 20-1, 20-2, 20-3 with like reference numbers are equally applicable to system 20-4 except as otherwise noted.

In system 20-4, WAM 26 is not in communication with network 60 such that the VCA computer and the bed command computer of network 60 are not used to determine whether the caregiver or patient are authorized to control bed 30 by voice. Instead, bed 30 of system 20-4 includes circuitry with embedded voice recognition (VR) and/or natural language processing (NLP) software as indicated diagrammatically at block 80. The circuitry 80 having the embedded VR/NLP software communicates bidirectionally with bed controller 34 over a wired link or connector 82 as shown diagrammatically in FIG. 4. Circuitry 80 includes its own processor and memory in some embodiments. See the descriptions of processor 36 and memory 38 above which are equally applicable to the processor and memory of circuitry 80 in such embodiments. In other embodiments, circuitry 80 is included as part of bed controller 34. Thus, memory 38 stores the VR/NLP software for execution by processor 36 of controller 34 in some embodiments.

In system 20-4, the functionality of the VCA computer and bed command computer of network 60 of system 20-3, are provided on bed 30. In this regard, circuitry 80 and controller 34 collectively or individually operate as an on-bed computer for processing of the voice inputs 70, 72 received by microphones 48 of bed 30 from the caregiver or patient. Bed 30 includes wired links 81 between microphone and speaker units 48 and circuitry 80 as shown diagrammatically in FIG. 4. Circuitry 80 of bed 30 stores the digital models of voices of caregivers and patients who are authorized to control bed 30 by voice. Thus, the digital models are stored in memory of circuitry 80, or memory 38 of bed controller 34, prior to receipt of voice inputs 70, 72 from the patient and caregiver. Controller 34 and/or circuitry 80 of bed 30 receive the digital models of voices from a remote computer in some embodiments. In other embodiments, authorized caregivers and patients record voice samples using microphone 48 of bed 30 to create the digital models. Thus, a training routine may be implemented by the VR/NLP software to create the needed digital models of authorized voices.

Based on the foregoing, it should be appreciated that the present disclosure contemplates that an application that runs on a computer (e.g., the VCA computer of network 60 or an on-bed computer 54, 80 of bed 30) or one a mobile device (e.g., mobile phones 22, 22') and records a digital model of each caregiver's voice and, in some embodiments, the voices of one or more patients. The voice models are transferred to the medical devices, such as bed 30, or to a server (e.g., VCA computer) to be used for voice biometrics. In some embodiments, the application runs on the mobile device 22, 22' and updates the voice profile/digital model each day to improve accuracy of the digital model. In this regard, reference is made to FIG. 7 in which a flow chart of an algorithm 200 is shown. Algorithm 200 begins at block 202 where a caregiver uses the application on mobile phone 22 to create a voice model. Thereafter, the application pushes the voice model with a caregiver ID to one or more medical devices (e.g., one or more of beds 30) as indicated at block 204. Thereafter, the application on mobile device 22 updates the voice profile daily as a caregiver uses the mobile device 22, thereby to improve the accuracy of the voice model, as indicated at block 206.

The present disclosure further contemplates that the caregiver may use a combination of voice inputs and touch screen inputs to operate the various features of bed 30, thereby making bed features easier to use while maintaining safe operation. That is, even though a caregiver is authorized to provide voice inputs for control of bed 30, the caregiver is still able to use the manual inputs, including touchscreen display inputs, of bed 30 to control the various bed functions.

To give one example of caregiver voice control of bed 30 contemplated herein, a caregiver may say, "hey Centrella, weigh patient." Centrella is the model name of the bed in this example, but other bed names or medical device names are used as appropriate. In response to the stated voice input, the Centrella bed 30 displays the current patient weight and asks the caregiver to accept the weight to be stored in memory 38 of the bed 30 and, in some embodiments, sent to the patient's electronic medical record which is stored in a database of an EMR computer. If bed 30 detects a problem, for example the patient weight is significantly different, it gives the caregiver audible feedback—"patient weight is more than x pounds different than the last stored weight. Please check for items added to the bed and make sure the bed has been properly zeroed". If no problems are detected, the bed plays an audio message through speaker units 48 stating, "weight successfully stored" or some similar such confirmation message.

While the above description contemplates that voice recognition (e.g., using voice biometrics) is used to determine whether caregivers and/or patients are authorized for voice control of medical devices, the present disclosure contemplates other ways to determine voice control authorization in addition to, or in lieu of, the use of voice recognition. Thus, the present disclosure contemplates the following options, alone or in any combination, to determine authorization of users to control medical devices by voice: (i) an RTLS associates the caregiver with the bed and enables use of voice commands; (ii) PIN entry on a screen (e.g., touchscreen of mobile phone 22, 22' or touchscreen of bed 30); and (iii) voice biometrics. With regard to using a combination of these voice, RTLS, PIN authorization methodologies, the authorization or access options may vary and be automatically applied based on a risk profile or risk level of the operation. That is, more risky operations may require two or three of the authorization methodologies to be met prior to use, whereas less risky operations may require only one of the authorization methodologies to be met prior to use.

Referring now to FIG. 8, a method 210 is shown in which different levels of authorization are required depending upon what medical device function is to be implemented. Method 210 begins in response to a caregiver wearing an RTLS tag 25 entering a patient room as indicated at block 212. At block 214 the RTLS sends a message to bed 30 to notify the bed 30 that an authorized caregiver is in the room. The caregiver then gives a voice command to bed 30 stating, in the illustrative example, "hey bed name weigh patient" as indicated at block 216. Of course, "bed name" in this example is replaced by an actual model name of a bed in practice. The software of bed 30 then determines that weighing the patient is a low risk function and displays the weight of the current patient after determining that the user entering the voice command is a valid (e.g., authorized) user by using voice biometrics and after weighing the patient, as indicated at block 218.

After the patient is weighed and the weight displayed at block 218, the method 210 proceeds to block 220 where the bed 30 asks (e.g., plays an audio message through speaker units 48) if the caregiver wants to chart the patient weight. If the caregiver responds "yes" as indicated at block 222, the software of bed 20 determines that charting weight is a higher risk task that requires further authentication of the caregiver as indicated at block 224. Thereafter, bed 30 gets and checks data received from the RTLS system to authenticate the caregiver or user as indicated at block 226. After the caregiver is authenticated at block 226, bed 30 sends the patient weight to the EMR system for charting. As indicated by a note 229 at the bottom of FIG. 8, if the RTLS is not available (e.g., is omitted from the respective system 20 or is present but offline for whatever reason), then bed 30 prompts the caregiver or user to enter a PIN.

With the foregoing in mind, a voice control system 20 for a healthcare facility includes a patient bed 30 that has a weigh scale to weigh a patient supported on the patient bed and that has a display screen to display the patient's weight. The voice control system 20 further includes a voice recorder configured to record digital models of voices of a plurality of caregivers and a server to which the digital models are transferred for determining voice biometrics of each caregiver. The patient bed 30 is configured to receive a voice input from a first caregiver of the plurality of caregivers that instructs the patient bed 30 to weigh the patient. The patient bed is configured to communicate with the server to confirm that the caregiver is authorized to control the patient bed 30 by the voice input based on the voice biometrics. After confirmation that the first caregiver is authorized to control the patient bed 30, the patient is weighed by the weigh scale and the patient's weight is displayed on the display screen.

In some embodiments, the voice recorder is included in a computer. Alternatively or additionally, the voice recorder is included in a mobile phone 22. Optionally, a caregiver identification (ID) is transmitted to the server by the voice recorder with the digital model of each caregiver of the plurality of caregivers. In some embodiments, the patient bed 30 is configured to receive a zero scale voice input from the first caregiver that instructs the patient bed 30 to zero the weigh scale by measuring a tare weight with the weigh scale when the patient is not in bed 30. In this regard, the patient bed 30 is configured to communicate with the server to confirm that the caregiver is authorized to control the patient bed 30 by the zero scale voice input based on the voice biometrics. After confirmation that the first caregiver is authorized to control the patient bed 30, the patient bed 30 zeroes the weigh scale.

In some embodiments, the patient bed 30 is configured to display an accept button on the display screen for selection by the first caregiver to accept the displayed patient weight for storage in one or both of memory 38 of the patient bed 30 and an electronic medical record of the patient. If the displayed weight that has been accepted by the first caregiver is different than a previously accepted patient weight by a threshold amount, the patient bed 30 may display a message on the display screen instructing the first caregiver to check to determine if the weigh scale of the patient bed 30 has been properly zeroed. If no problems are detected by the patient bed 30, the patient bed displays a message on the display screen that indicates that the patient weight was successfully stored in one or both of the memory of the patient bed and the electronic medical record of the patient.

In some embodiments, the voice control system 20 further includes a real time locating system (RTLS) that determines the locations of the plurality of caregivers in the healthcare facility. The server uses information from the RTLS in addition to the voice biometrics to confirm that the first caregiver is authorized to control the patient bed 30 by the voice input. Optionally, the patient bed 30 is configured to display a personal identification number (PIN) screen on the display screen for the first caregiver to enter a PIN and the server uses the PIN in addition to the voice biometrics to confirm that the first caregiver is authorized to control the patient bed 30 by the voice input. The use of the PIN in addition to the use of the voice biometrics to determine that the first caregiver is authorized may be in addition to, or in lieu of, the use of information from the RTLS. In some embodiments, the patient bed 30 is configured to display a voice input button on the display screen that is selectable by the first caregiver to enable the patient bed 30 to receive the voice input.

As also contemplated herein, a voice control system 20 for a healthcare facility includes a medical device that is used in care for a patient and a mobile device 22 that includes a voice recorder configured to record a digital model of a voice of a caregiver. The digital model is transferred to the medical device from the mobile device 22. The medical device is configured to determine voice biometrics of the caregiver based on the digital model. The medical device is also configured to receive a voice input from the caregiver that instructs the medical device to carry out a function. The medical device is configured to confirm that the caregiver is authorized to control the medical device by the voice input based on the voice biometrics. After confirmation that the caregiver is authorized to control the medical device, the function is carried out by the medical device.

In some embodiments, a caregiver identification (ID) of the caregiver is transmitted to the medical device from the mobile device 22 along with the digital model of the voice of the caregiver. In some embodiments, the medical device is configured to display an accept button on a display screen for selection by the caregiver to accept displayed patient information for storage in one or both of memory of the medical device and an electronic medical record of the patient. If no problems are detected by the medical device, the medical device displays a message on the display screen that indicates that the patient information was successfully stored in one or both of the memory of the medical device and the electronic medical record of the patient.

It is contemplated by the present disclosure that, in some embodiments, the voice control system 20 further includes a real time locating system (RTLS) that determines the location of the caregiver in the healthcare facility. The medical device uses information from the RTLS in addition to the voice biometrics to confirm that the caregiver is authorized to control the medical device by the voice input.

Alternatively or additionally, the medical device is configured to display a personal identification number (PIN) screen on a display screen for the caregiver to enter a PIN and the medical device uses the PIN in addition to the voice biometrics to confirm that the first caregiver is authorized to control the medical device by the voice input. The use of the PIN in addition to the use of the voice biometrics to determine that the first caregiver is authorized may be in addition to, or in lieu of, the use of information from the RTLS. In some embodiments, the medical device is configured to display a voice input button on a display screen that is selectable by the caregiver to enable the medical device to receive the voice input.

According the present disclosure, a voice control system 20 for a healthcare facility includes a patient bed 30 that has a weigh scale to weigh a patient supported on the patient bed and that has a display screen to display the patient's weight. A real time locating system (RTLS) is provided to track locations of a plurality of caregivers in the healthcare facility. The RTLS is configured to send a message to the patient bed 30 that notifies the patient bed 30 that a first caregiver has entered into a room in which the patient bed 30 is situated. The patient bed 30 is configured to receive a voice input from the first caregiver that instructs the patient bed 30 to weigh the patient. Furthermore, the patient bed 30 is configured to confirm that the first caregiver is authorized to control the patient bed 30 by the voice input based on voice biometrics of the first caregiver stored in memory 38 of the patient bed 30. After confirmation that the first caregiver is authorized to control the patient bed, the patient is weighed by the weigh scale and the patient's weight is displayed on the display screen.

In some embodiments, the patient bed 30 is configured to play an audio message that inquires whether the first caregiver wants to chart the displayed patient weight for storage in an electronic medical record of the patient. In response to the first caregiver responding vocally in the affirmative to the audio message, the patient bed 30 communicates with the RTLS to re-confirm that the first caregiver is authorized to chart the patient weight for storage in the electronic medical record of the patient. After the RTLS of the third aspect re-confirms that the first caregiver is authorized, the patient weight is transmitted to an EMR system for storage in the electronic medical record of the patient.

Optionally, the patient bed 30 is configured to display a chart button on the display screen for selection by the first caregiver to chart the displayed patient weight for storage in an electronic medical record of the patient. In response to selection of the chart button by the first caregiver, the patient bed 30 communicates with the RTLS to re-confirm that the first caregiver is authorized to chart the patient weight for storage in the electronic medical record of the patient. After the RTLS re-confirms that the first caregiver is authorized, the patient weight is transmitted to an EMR system for storage in the electronic medical record of the patient.

In some embodiments, in response to the first caregiver responding vocally in the affirmative to the audio message, the patient bed 30 displays a personal identification number (PIN) screen on the display screen for the first caregiver to enter a PIN and the patient bed 30 uses the PIN to re-confirm that the first caregiver is authorized to chart the patient weight for storage in the electronic medical record of the patient. After the patient bed of the third aspect re-confirms that the first caregiver is authorized based on the PIN, the patient weight is transmitted to an EMR system for storage in the electronic medical record of the patient.

Alternatively, in response to selection of the chart button by the first caregiver, the patient bed 30 displays a personal identification number (PIN) screen on the display screen for the first caregiver to enter a PIN and the patient bed 30 uses the PIN to re-confirm that the first caregiver is authorized to chart the patient weight for storage in the electronic medical record of the patient. In such alternative embodiments, after the patient bed 30 re-confirms that the first caregiver is authorized based on the PIN, the patient weight is transmitted to an EMR system for storage in the electronic medical record of the patient.

Figure 5:
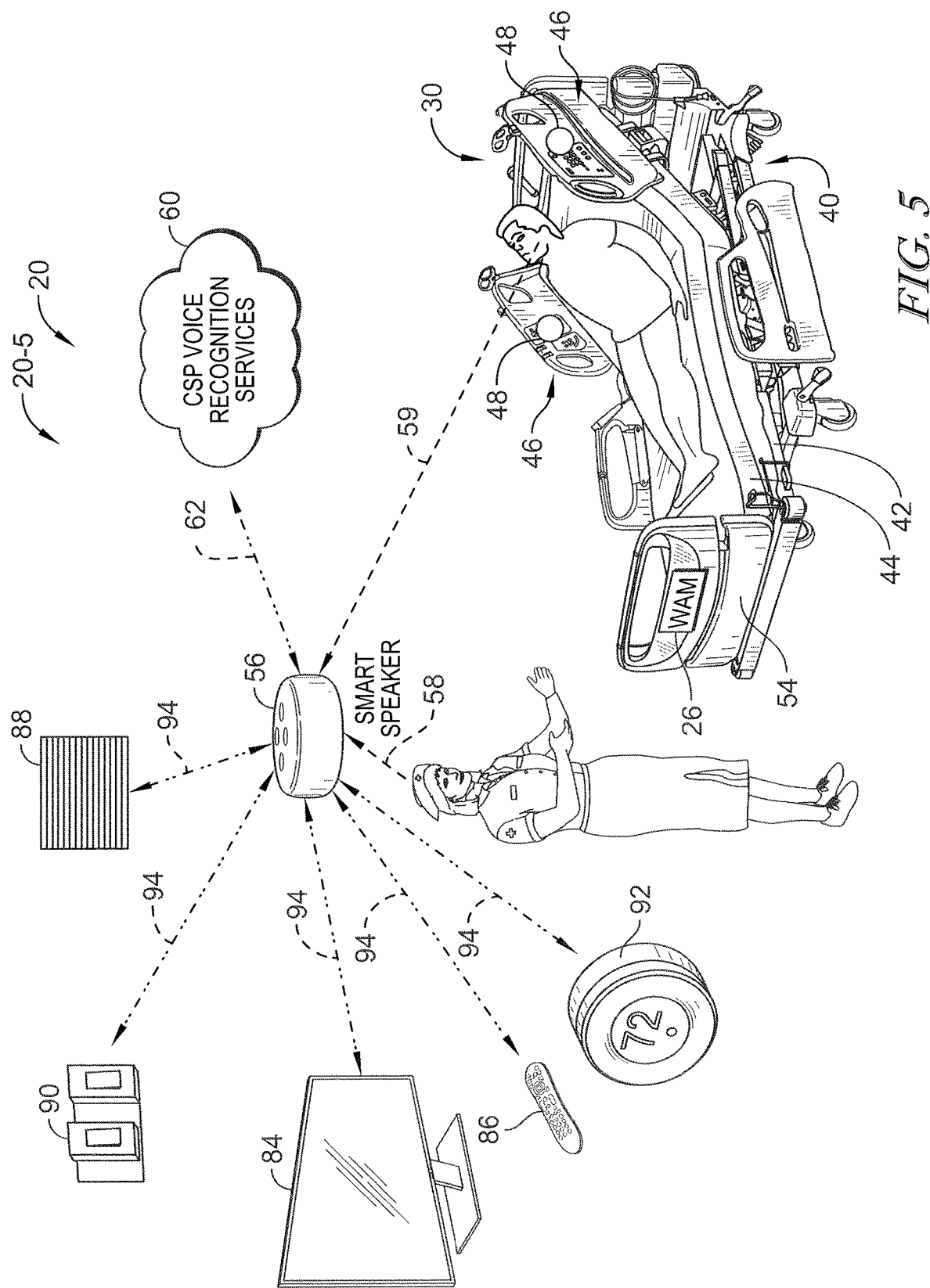
FIG. 5 is a diagrammatic view of a fifth voice control system, similar to FIG. 2, showing a smart speaker unit above the caregiver, the smart speaker unit configured to receive voice inputs from the caregiver and the patient, the speaker unit being in wireless communication with room environment and entertainment devices, and the smart speaker unit being in communication with a network having CSP voice recognition services provided by software of one or more servers of the network so that the one more severs are able to process the voice inputs and provide command messages to the smart speaker unit to control functions of the environment and entertainment devices.

Referring now to FIG. 5, a diagrammatic view of a fifth voice control system 20-5, similar to system 20-2 of FIG. 2, is provided. Reference numbers for aspects to system 20-5 that are common to aspects of systems 20-1, 20-2, 20-3, 20-4 of FIGS. 1-4 are used in FIG. 5 and the descriptions are not repeated but are equally applicable. In system 20-5, speaker unit 56 receives voice inputs 58, 59 from the caregiver and patient, respectively, to control environment devices and entertainment devices in the patient room. In the illustrative example of system 20-5, the entertainment devices include the speaker unit 56 itself and a television (TV) 84 along with a TV remote control 86 having a microphone for receipt of voice inputs in some embodiments. The environment devices of system 20-5 depicted in FIG. 5 include a motorized window blind 88, a room light 90, and thermostat 92 for control of the room temperature. In some embodiments, a motorized curtain is used in lieu of motorized window blind 88 to block light from entering the associated window of the patient room. Thus, reference number 88 is intended to represent either or both of a motorized window blind and motorized curtain. The term "motorized" with regard to blinds and/or curtains 88 means that one or more motors are provided to open and close the blinds or curtain(s) as the case may be, and to angle the louvres or slats of the window blinds 88.

The voice inputs 58, 59 from the caregiver and patient to control one or more of devices 84, 86, 88, 90, 92, and/or similar such devices, are converted by speaker unit 56 into voice control messages, such as audio files, and are transmitted from speaker unit 56 to network 60 via the wireless communication link 62. The VCA computer of network 60 operates the CSP voice recognition software to confirm that the caregiver and/or patient are authorized to control the respective device(s) 84, 86, 88, 90, 92, or similar such devices, by voice control. If voice control authorization is confirmed, the VCA computer, either alone or in cooperation with another computer, transmits command messages back to the speaker unit 56 over the wireless communication link 62. The speaker unit 56, in turn, distributes the command message wirelessly to the particular device(s) 84, 86, 88, 90, 92, or similar such device to be controlled, via a respective wireless link 94. In some embodiments, feedback regarding the status of the device(s) 84, 86, 88, 90, 92 being controlled is communicated to speaker unit 56 over the respective wireless link 94 for forwarding to one or more computers of network 60.

The speaker unit 56 also is contemplated by this disclosure as serving as one of the entertainment devices in the patient room. For example, speaker unit 56 is configured to play audio of recorded books, voice-based games, and trivia, typically in response to voice inputs 59 from the patient, but this is not to rule out the possibility that such entertainment functions may be initiated by a caregiver in some instances. Thus, speaker unit 56 serves the dual function of being a gateway for voice commands 58, 59 to network 60 and for command messages from network 60 to devices 84, 86, 88, 90, 92, as well as for feedback messages from devices 84, 86, 88, 90, 92 and being an entertainment device itself. Furthermore, it should be appreciated that the use of speaker unit 56 for control of entertainment and environment devices 84, 86, 88, 90, 92 as described in connection with system 20-5 may be implemented in addition to the control of medical devices, including patient bed 30, described above in connection with any of systems 20-1, 20-2, 20-3, 20-4 of FIGS. 1-4, respectively.

Based on the foregoing, the present disclosure contemplates a system 20-5 for voice control of a patient room environment. The system 20-5 includes an environment device 88, 90, 92 operable to control the patient room environment, an entertainment device 56, 84, 86 operable to provide entertainment to a patient in the patient room, and a microphone (e.g., the microphone of speaker unit 56) that is situated in the patient room and that is configured to receive voice control commands from the patient for controlling the environment device 88, 90, 92 and the entertainment device 56, 84, 86. The system 20-5 also includes a remote computer (e.g., VCA computer of network 60) that is communicatively coupled to the microphone and that has voice recognition software. The remote computer is configured to process the voice control commands and to send control messages to control the operation of the environment device 88, 90, 92 and the entertainment device 56, 84, 86.

In some embodiments, the environment device includes one or more of the following: a motorized window blind 88, a motorized curtain (also represented diagrammatically by reference number 88), a room light 90, a reading light (also represented diagrammatically by reference number 90), or a thermostat 92. The entertainment device include a television 84. Alternatively or additionally, the entertainment device include speaker unit 56 that is configured to play audio of recorded books, voice-based games, and trivia. Optionally, the microphone of system 20-5 is included in the speaker unit 56. Further optionally, the system 20-5 further includes a patient bed 30 configured to support the patient and the speaker unit 56 is included in the patient bed 30.

If desired, the entertainment device of the system 20-5 includes a second entertainment device (e.g., remote control 86) spaced from the speaker unit 56 and the control messages to control the operation of the environment device (e.g., TV 84) and the second entertainment device (e.g., remote control 86) are routed to the environment device 84 and the second entertainment device 86 through the speaker unit 56. It is contemplated by the present disclosure that the control messages are received by the speaker unit 56 as wireless control messages. Alternatively or additionally, the control messages sent to the environment device 84 and the second entertainment device 86 from the speaker unit 56 are transmitted wirelessly.

Figure 6:
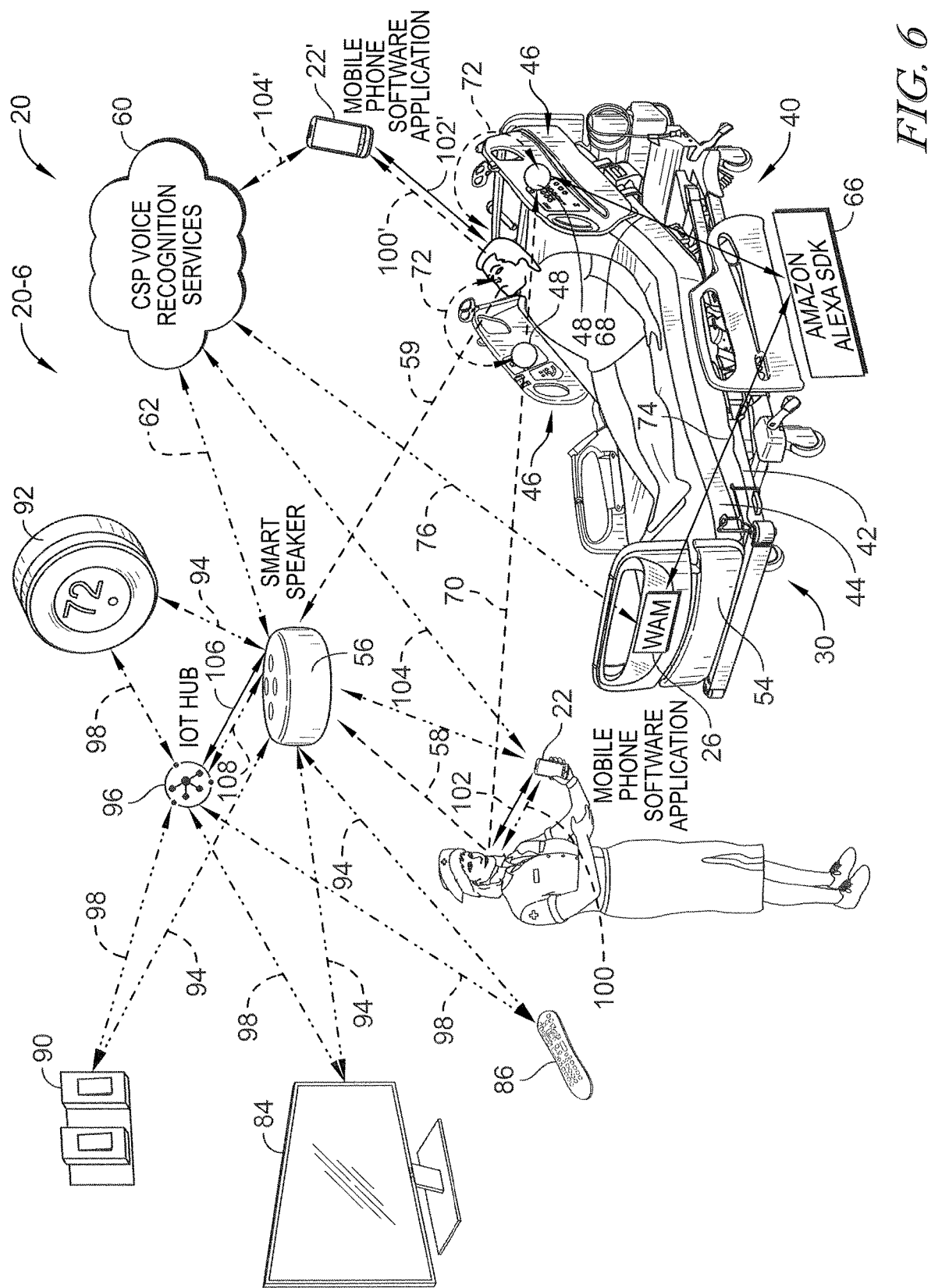
FIG. 6 is a diagrammatic view of a sixth voice control system, similar to FIGS. 1-5, showing the smart speaker unit being configured to receive voice inputs from the caregiver and the patient, the smart speaker cooperating with an Internet of Things (IoT) hub and the network having CSP voice recognition services provided by software of one or more servers of the network so that the smart speaker, the network, and/or the IoT hub provides command messages based on the voice inputs to control functions of the patient bed, the environment devices, and the entertainment devices.

Referring now to FIG. 6, a diagrammatic view of a sixth voice control system 20-6, similar to systems 20-1, 20-2, 20-3, 20-4, 20-5 of FIGS. 1-5, respectively, is provided. Reference numbers for aspects to system 20-6 that are common to aspects of systems 20-1, 20-2, 20-3, 20-4, 20-5 of FIGS. 1-5 are used in FIG. 6 and the descriptions are not repeated but are equally applicable. The main difference between system 20-5 of FIG. 5 and system 20-6 of FIG. 6 is that an Internet of Things (IoT) hub 96 is provided. The IoT hub 96 is a standalone hub that is spaced from the medical devices, such bed 30, in some embodiments. In other embodiments, the IoT hub 96 is included in the medical device, such as bed 30. In some embodiments, IoT hub 96 is an Insteon hub available from SmartLabs, Inc. of Irvine, California. In FIG. 6, the motorized window blind or curtain 88 of FIG. 5 is not shown, but is among the environment devices of system 20-6 in some embodiments.

The IoT hub 96 allows for system 20-6 to be provided with an agnostic mic array in the patient room by use of microphones in various different devices (e.g., bed 30, speaker unit 56 such as the AMAZON® ECHO device or a GOOGLE® HOME device, etc.). The IoT hub 96 also allows system 20-6 to be agnostic as which voice recognition (VR) and/or natural language processing (NLP) services are to be used and to be agnostic as to which TV brand is controlled by voice. In one example of system 20-6, a voice based nurse call system is provided by an AMAZON® ECHO device 56 and an AWS Cloud Stack to VR and machine learning (ML). Thus, the present disclosure contemplates that the IoT hub 96 in the bed 30 or in the patient room provides for channeling the processing of voice inputs to a local network 60 (e.g., local edge computing) or to an external network (e.g., an external mesh network) as needed, depending upon the type of device to be controlled. In FIG. 6, the external network with which IoT hub 96 communicates is not shown.

If voice control inputs 70, 72 are not able to be handled locally by network 60, then IoT hub 96 is used to communicate with the external network to obtain the needed command messages for control of the devices 56, 84, 86, 88, 90, 92 in the room. Thus, the IoT hub 96 communicates wireless command messages 98 to devices 56, 84, 86, 88, 90, 92, as needed, after the external network responds with the command message that is needed for control of the particular device 56, 84, 86, 88, 90, 92 based on the voice input 70, 72. The architecture of system 20-6 allows provided flexibility for the system designer to decide where (i.e., internally with network 60 or externally via IoT hub 96) the voice input processing is to be done for the various medical devices, entertainment devices, and environment devices that are found in the various patient rooms.

As also shown in FIG. 6, the caregiver is able to provide voice inputs 100 and touch inputs 102 to mobile phone 22 for control of medical devices such as bed 30 and the other devices 56, 84, 86, 88, 90, 92 in the patient room. Similarly, the patient is able to provide voice inputs 100' and touch inputs 102' to mobile phone 22' for control of medical devices, such as bed 30, and the other devices 56, 84, 86, 88, 90, 92 in the patient room. In the illustrative example of system 20-6 in FIG. 6, mobile phones 22, 22' communicate with network 60 without involving WAM 26 of bed 30. For example, mobile phones 22, 22' communication with wireless access points (WAP's) of network 60 in some embodiments. The WAP's then forward the voice inputs 100, 100' to the VCA computer and forward the touch inputs 102, 102' to other computers depending upon the device to be controlled by the touch inputs.

If the IoT hub 96 is required for processing any of the inputs 100, 100', 102, 102', then signals corresponding to the inputs 100, 100', 102, 102' are provided by the network 60 to speaker unit 56 via wireless communication link 62 and then speaker unit 56, in turn, communicates the inputs 100, 100', 102, 102' via an embedded link 106 or a wireless link 108 to IoT hub 96. Command messages to control the medical device, such as bed 30, are either sent from network 60 to the medical device via wireless communication link 76 or are routed back through network 60 from IoT hub 96 (e.g., via one of links 106, 108 to speaker unit 56 and then via wireless communication link 62 between speaker unit 56 and network 60) for delivery to the medical device via wireless communication link 76.

In embodiments in which IoT hub 96 is included in a medical device, such as patient bed 30, each of such medical devices having an IoT hub 96 acts as a communication and computation node in the network 60 of the healthcare facility. Thus, the computation needed for processing voice inputs, as well as video inputs, sensor inputs, and/or text inputs for that matter, can be localized to the patient room or distributed among other network nodes (either internal or external or both). If the computation is localized to the patient room, then edge network and cloud based computational infrastructure is avoided.

Based on the foregoing, the present disclosure contemplates a system 20-6 for voice control of a patient room environment. The system 20-6 includes an environment device 88, 90, 92 operable to control the patient room environment, an entertainment device 56, 84, 86 operable to provide entertainment to a patient in the patient room, and a microphone (e.g., microphone of speaker unit 56, microphones 48 of bed 30, and a microphone of mobile phone 22') situated in the patient room and configured to receive voice control commands from the patient for controlling the environment device 88, 90, 92 and the entertainment device 56, 84, 86. The system 20-6 also includes an Internet of Things (IoT) hub 96 communicatively coupled to the microphone. The microphone of system 20-6 is configured to transmit the voice control commands to the IoT hub 96 (e.g., via other components and equipment of system 20-6) and the IoT hub 96 is configured to transmit control messages 98 to control operation of the environment device 88, 90, 92 and the entertainment device 56, 84, 86.

In some embodiments of system 20-6, the environment device includes one or more of the following: a motorized window blind 88, a motorized curtain (also represented by reference number 88), a room light 90, a reading light (also represented by reference number 90), or a thermostat 92. The entertainment device of system 20-6 includes a television 84. Alternatively or additionally, the entertainment device of system 20-6 includes speaker unit 56 that is configured to play audio of recorded books, voice-based games, and trivia. Optionally, the microphone of system 20-6 is included in the speaker unit 56. Further optionally, the system 20-6 further includes patient bed 30 that is configured to support the patient and the speaker unit 56 is included in the patient bed 30.

If desired, the entertainment device of system 20-6 includes a second entertainment device (e.g., remote control 86) spaced from the speaker unit 56 and the control messages 98 from the IoT hub 96 to control the operation of the environment device 88, 90, 92 and the second entertainment device 86 is routed to the environment device 88, 90, 92 and the second entertainment device 86 via the speaker unit 56. It is contemplated by the present disclosure that at least some of the control messages of system 20-6 may be received by the speaker unit 56 from the IoT hub 96 as wireless control messages 108. Alternatively or additionally, the control messages 94 of system 20-6 sent to the environment device 88, 90, 92 and the second entertainment device 86 from the speaker unit 56 are transmitted wirelessly.

In some embodiments, system 20-6 further includes a second environment device 88, 90, 92, a second entertainment device 56, 84, 86, and a remote computer (e.g., VCA computer of network 60 or computer of external network coupled to IoT hub 96) that is communicatively coupled to the microphone and that has voice recognition software. The remote computer is configured to process the voice control commands and to send second control messages to control the operation of the second environment device 88, 90, 92 and the second entertainment device 56, 84, 86. Optionally, the second control messages are transmitted to the second environment device 88, 90, 92 and the second entertainment device 56, 84, 86 without involving the IoT hub 96. Further optionally, system 20-6 includes speaker unit 56, the microphone is included in the speaker unit 56, and the second control messages are transmitted to the second environment device 88, 90, 92 and the second entertainment device 56, 84, 86 though the speaker unit 56.

As shown in FIGS. 1-6, systems 20-1, 20-2, 20-3, 20-4, 20-5, 20-6 include various wireless communication links 24, 28, 28', 52, 62, 64, 76, 94, 98, 104, 104' 106, 108 between components of the respective systems 20-1, 20-2, 20-3, 20-4, 20-5, 20-6. The wireless communication technologies used for wireless communication links 24, 28, 28', 52, 62, 64, 76, 94, 98, 104, 104' 106, 108 is at the discretion of the system designer. However, examples of wireless communication technologies that may be employed in systems 20-1, 20-2, 20-3, 20-4, 20-5, 20-6 include Bluetooth (BT), such as Bluetooth Low Energy (BLE); WiFi (e.g., according to any of the IEEE 802.11x protocols); ultra wideband (UWB); Zigbee; Z-wave; 6LoWPAN; Thread; WiFi-ah (HaLow); 2G (GSM); 3G; 4G; 5G; LTE Cat 0, 1 & 3; LTE-M1; NB-IoT; RFID; SigFox; LoRaWAN; Ingenu; Weightless-N; Weightless-P; Weightless-W; ANT & ANT+; DigiMesh; MiWi; EnOcean; Dash7; and WirelessHART; just to name a few.

With regard to some functions of medical devices of systems 20-1, 20-2, 20-3, 20-4, 20-5, 20-6, it is desirable that information regarding adherence to care protocols (e.g., a Fall Prevention protocol, a Safe Skin protocol, a Sepsis care protocol, a Clear Lungs protocol, etc.) is documented in the EMR system for the respective patients to which the care protocols pertain to track and document compliance. Care protocol documentation is just another task that adds time to caregiver workload not directly related to patient care. In many Med-Surg units of healthcare facilities, the caregivers may be required to document that they have followed falls prevention protocols every two hours, for example. Caregivers may be required to document some things that are directly related to the bed 30 and some things that are not. For example, caregivers may be required to document the following: two, three, or four siderails up (e.g., siderails in the raised position), bed low (e.g., a lift of bed 30 supports an upper frame of the bed 30 in a lowered position relative to a base frame of the bed 30), brake set (e.g., one or more casters of the bed being braked), bed exit armed (e.g., a bed exit system of the patient bed 30 being turned on so as to monitor a position of the patient relative to the bed and to alarm if the patient moves into a position indicative of bed exit or moves toward exiting the bed 30 by a threshold amount), patient can reach a nurse call pendent (aka a "pillow speaker"), and a pathway from bed 30 to a bathroom of the patient room is not obstructed.

Because the present disclosure contemplates that bed 30 is equipped with speaker and microphone unit 48 and because systems 20-1, 20-2, 20-3, 20-4, 20-5, 20-6 include SCP software, VR software, and the like for processing voice inputs either on bed 30 or on one or more remote computers of network 60, charting protocol compliance to the EMR system is possible. In some embodiments of system 20, voice inputs for EMR charting may also be accomplished via voice inputs to caregiver mobile phone 22 or speaker unit 56 in addition to, or in lieu of, voice inputs to mic and speaker units 48 of beds.

In accordance with one workflow example for charting protocol compliance to an EMR system in which bed 30 is the CENTRELLA® bed available from Hill-Rom Company, Inc., a caregiver enters the patient room having bed 30 and says the following voice input "Centrella, perform fall prevention check." In response to the voice input, the bed 30 check to determine and confirm that the bed is in the safe state for a fall risk patient—side rails up, bed low, brake set and bed exit alarm armed. If the bed 30 is not in the safe state, the bed prompts the caregiver to change bed settings or position as needed. The prompt is a text message on graphical user interface (GUI) of bed 30, a text message that appears on mobile phone 22 of the caregiver (e.g., in a pop-up window on the display screen of phone 22), and/or an audible message played through speaker unit 48 of bed 30, for example. If the bed 30 is in safe state, the bed plays an audible message to tell the caregiver, for example, —"bed is in safe state for falls risk patient." Alternatively or additionally, a similar text message is displayed on the GUI of bed 30 and/or on the caregiver's mobile phone 22. Further alternatively or additionally, the audible message is played through the speaker of the caregiver's mobile phone 22.

After the bed 30 has been confirmed to be in the safe state by bed controller 34, the bed 30 plays an audible message through speaker unit 48 of bed 30 to ask the caregiver or the patient if the nurse call pendant is available (in reach) to the patient. Alternatively or additionally, a text message inquiring whether the nurse call pendant is within reach of the patient is displayed on the GUI of bed 30 and/or on the caregiver's mobile phone 22 or even the patient's mobile phone 22' in some embodiments. If the answer to the query regarding nurse call pendant accessibility to the patient is "no," the bed 30 prompts the caregiver to correct the situation (e.g., move the nurse call pendant so as to be accessible to the patient) and confirm. The pendant accessibility prompt can be audible via speaker unit 48 of bed 30 or the caregiver's mobile phone 22, or can be textual such as being displayed on the GUI of bed 30 or on the caregiver's mobile phone 22.

After the caregiver confirms to the bed 30 that the nurse call pendant is accessible to the patient, by an affirmative voice input to microphone 48 of bed 30 or mobile phone 22 which is transmitted to WAM 26 of bed 30, or by an affirmative manual input to the GUI of bed 30 or to the display screen of the mobile phone 22 which is transmitted to WAM 26 of bed 30, the bed 30 plays an audible message through speaker unit 48 of bed 30 to ask the caregiver to confirm that pathways around the bed 30 are not obstructed. Alternatively or additionally, a text message inquiring whether the pathways around the bed are clear is displayed on the GUI of bed 30 and/or on the caregiver's mobile phone 22. If the answer to the query regarding the pathways around the bed 30 being clear to the patient is "no," the bed 30 prompts the caregiver to correct the situation (e.g., clear the pathways around the bed 30, and particularly the pathway from the bed 30 to the bathroom, for the patient) and confirm. The clear pathways prompt can be audible via speaker unit 48 of bed 30 or the caregiver's mobile phone 22, or can be textual such as being displayed on the GUI of bed 30 or on the caregiver's mobile phone 22.

After the caregiver confirms to the bed 30 that the pathways around the bed 30 are clear, by an affirmative voice input to microphone 48 of bed 30 or mobile phone 22 which is transmitted to WAM 26 of bed 30, or by an affirmative manual input to the GUI of bed 30 or to the display screen of the mobile phone 22 which is transmitted to WAM 26 of bed 30, the bed 30 informs the caregiver, either audibly and/or textually via the GUI of bed 30, the speaker unit 48 on bed 30, the speaker of phone 22, and/or the display screen of mobile phone 22, that the fall prevention check is complete and complies with fall prevention protocol and also asks the caregiver if he/she is ready to chart the compliance check to the EMR system (e.g., for storage in a database of an EMR computer). In response to the caregiver replying "yes" to the charting query, either vocally or via manual input on the GUI of bed 30 or the touchscreen of mobile phone 22, information regarding the falls prevention check is charted to the EMR system from the bed 30. Thus, the present disclosure contemplates that bed 30 has voice capabilities and can interact with the caregiver and the patient to ensure that care protocols are followed and to chart information regarding successful care protocol checks automatically to the EMR system of the healthcare facility in response to caregiver affirmation that the respective care protocols have been followed.

Some operations on medical devices inherently may cause hazards to patients. For example, articulating any of the deck sections of deck 42 of the bed 30 while the patient is in traction can potentially cause harm to the patient. For beds requiring manual inputs such as button presses to articulate a deck section, at any point during the movement of the deck section, a user can release the articulation button to stop the movement and potentially prevent harm to the patient. Similar hazards inherent to beds 30 relate to operating the lift of bed 30 to lower the upper frame of the bed 30 relative to the base frame.

In embodiments of system 20 in which bed 30 or other medical devices having inherent hazards are operated by voice, it is desirable to include a voice safety feature for such medical products in system 20. In particular, it is desirable that a voice input can be spoken to stop some action of the bed 30 or other medical device before any injury to the patient occurs. However, other functions of the bed 30 and medical devices that are not intended to be stopped should continue to function as normal. One way that the present disclosure contemplates to achieve this is to assume that when a caregiver issues a stop command, the caregiver is watching the potentially harmful action and the caregiver is properly aware of the potential harm that might occur if the function is continued. In this regard, embodiments of system 20 optionally are configured with software that is able to infer where the caregiver's eyes are looking by determining which way the caregiver's face, and thus the caregiver's eyes, are pointed when the caregiver is speaking via microphone beam-forming.

An array of microphones that are deployed in the product (e.g., microphones 48 on bed 30) and/or around the room (e.g., microphones of speaker units 56 or microphones in audio stations of a nurse call system (see FIG. 11)) have outputs that permit a beam-forming location device (e.g., the VCA computer of system 60) to translate and process the incoming voice information from the microphones and share with the device, such as bed 30, information as to whether the caregiver has been inferred to be looking at the device, including whether the caregiver is looking at the relevant portion of the device that is being operated with the potential to cause injury to the patient.

It should be noted that the more the caregiver speaks, the more accurately the beam-forming location device is able to tell the direction at with the caregiver's face, and presumably, the caregiver's eyes, are pointed. Accordingly, this safety feature of system 20 is best used in situations in which frequent caregiver-to-device communication occurs, so that the caregiver's eye directionality is updated on an ongoing basis and the risk to the patient can be mitigated during this period. Thus, the present disclosure contemplates that system 20 is configured with at least one computer that is operable to infer eye location because of directionality of the caregiver's voice. This information is used by system 20 in response to a spoken stop command to mitigate any hazard that might occur as a result of the operation of the medical product being viewed by the caregiver. In some embodiments, if the patient issues a vocal stop command and the VCA computer or bed controller 34 recognizes that the voice input is from the patient, movements of any medical devices in the room being used with that patient are stopped without regard to the directionality of the patient's face/eyes.

In embodiments of system 20 in which patient bed 30 is the medical device to which a spoken stop command pertains, the bed functions to be stopped may include, for example, bed articulation (e.g., movement of sections of deck 42 of frame 40 of bed 30), bed-based therapies or mattress movements, oftentimes performed by control of mattress bladder inflation and deflation, such as percussion and vibration (P&V) therapy, continuous lateral rotation (CLRT) therapy, and a turn assist function, and movement of an upper frame of the bed, such as by raising, lowering, or tilting, the upper frame, relative to a base frame. Movements of patient lifts, such as overhead patient lifts, ceiling-mounted patient lifts, patient lifts integrated into the patient bed 30, and so forth that are used to translate or transfer a patient to or from patient bed 30, and movements of surgical table sections may be stopped in a similar manner by using an array of microphones to determine face/eye directionality in connection with a spoken stop command by a caregiver.

Based on the foregoing, therefore, the present disclosure contemplates a system 20 to mitigate risk to a patient in a healthcare setting. The system 20 includes a medical product (e.g. patient 30) that has at least one function that, when operated, may have a possibility of causing ham' to the patient. Circuitry (e.g., bed controller 34) is carried by the medical product and include a processor 36 and memory 38 storing software. The system 20 also has an array of microphones (e.g., microphones 48, microphones of speaker units 56, microphones in audio stations of a nurse call system, microphones of other medical devices, and/or standalone microphones in the patient room) that are configured to receive voice inputs from a person in the vicinity of the medial product. The array of microphones are in communication with the circuitry and the software is configured to cooperate with the array of microphones to use beam-forming techniques to infer a direction that the person's eyes are pointed based on the voice inputs. The circuitry is configured to stop the at least one function that may have the possibility of causing harm to the patient in response to a vocal stop command being spoken by the person while the person's eyes are inferred to be pointed toward the medical product.

In some embodiments, the medical product includes patient bed 30 and the array of microphones 48 is mounted to the patient bed 30. Optionally, the patient bed 30 include at least one siderail 46 that is moveable between a raised position blocking the patient from egressing from the patient bed 30 and a lowered position unblocking the patient from egressing from the patient bed 30. At least one microphone 48 of the array of microphones is mounted to the at least one siderail.

If the medical product includes patient bed 30, some microphones of the array of microphones may be mounted to either or both of a room wall or a ceiling of the patient room in which the patient bed 30 is situated. For example, the array of microphones may include a first microphone mounted to the medical product and a second microphone mounted to either a room wall or a ceiling of a patient room in which the medical product is situated. Further optionally, the medical product may include a patient lift and the array of microphones may be mounted to either or both of a room wall and a ceiling of a patient room in which the patient lift is situated. If desired, the patient lift may comprise a mobile patient lift or a ceiling-mounted patient lift.

Further, if the medical product includes patient bed 30, the at least one function may include one or more of the following: movement of a mattress support section of a mattress-support deck 42 of the patient bed 30, movement of an upper frame of the patient bed relative to a base frame of the patient bed 30, operation of a percussion and vibration (P&V) therapy function of the mattress 44 of the patient bed 30, operation of a turn assist function of the mattress 44 of the patient bed 30, or operation of a continuous lateral rotation therapy (CLRT) function of the mattress 44 of the patient bed 30. Further optionally, the medical product may include a surgical table and the at least one function may include movement of a first surgical table portion relative to a second surgical table portion.

In some embodiments, the array of microphones of the system 20 is in wireless communication with the circuitry 34 of the medical product. Alternatively or additionally, the array of microphones may be in wired communication with the circuitry 34 of the medical product. Is desired, system 20 further may include a mobile phone 22, 22' that may be carried by the person. The mobile phone 22, 22' may be configured to receive voice commands from the person and transmit command messages corresponding to the voice commands to the medical product to commence operation of the at least one function. Alternatively or additionally, system 20 further may include at least one computer (e.g., VCA computer of network 60) that may be remote from the medical product. The at least one computer may have clinical voice recognition software. The array of microphones may communicate voice commands received from the person to the at least one computer. The at least one computer may be configured to transmit command messages corresponding to the voice commands to the medical product to commence operation of the at least one function.

It is contemplated by the present disclosure that the circuitry 34 is configured not to stop the at least one function that may have the possibility of causing harm to the patient in response to a vocal stop command being spoken by the person while the person's eyes are not inferred to be pointed toward the medical product. If desired, the circuitry 34 is configured to be trained to recognize the patient's voice and the circuitry is configured to stop the at least one function that may have the possibility of causing harm to the patient in response to a patient-originated vocal stop command being spoken by the patient without regard to directionality of the patient's eyes. In such embodiments, the medical product may include a patient bed 30 on which the patient is supported.

According to the present disclosure, system 20 is configured to permit a voice input to a medical device, such as bed 30, to be used for associating the medical device to a location in the healthcare facility. In such a device-to-room association system 20, the medical device has circuitry (e.g., controller 34) that include a processor 36, memory 38, and a transmitter (e.g., one of the electrical components of controller 34 and/or WAM 26). The device-to-room association system 20 also has at least one microphone (e.g., microphone 48, microphone of speaker unit 56, or some other microphone like those disclosed herein) that is communicatively coupled to the circuitry 34. The memory 38 stores software that is configured to receive voice inputs via the at least one microphone. The device-to-room association system 20 also includes a locating system that includes at least one locating computer (e.g., a computer of network 60) configured to store device-to-room associations. The circuitry 34 of the medical device is configured to receive a voice input from a person via the at least one microphone indicating a location identification (ID) at which the medical device is located. The circuitry 34 is configured to store the location ID in the memory 38 of the medical device and to transmit the location ID to the at least one locating computer along with a medical device ID. The at least one locating computer is configured to establish a first device-to-room association based on the medical device ID and the location ID transmitted from the medical device.

In some embodiments, the at least one microphone 48 of the device-to-room association system 20 is carried by the medical device. Optionally, the at least one microphone of the device-to-room association system 20 includes an array of microphones that are carried by the medical device. Further optionally, the at least one microphone of the device-to-room association system 20 is spaced apart from the medical device and is mounted at the location. For example, the at least one microphone of the device-to-room association system 20 may include an array of microphones that are spaced apart from the medical device and that are mounted at the location. If desired, the at least one microphone of the device-to-room association system 20 is configured to communicate wirelessly with the circuitry of the medical device.

The present disclosure contemplates that the at least one microphone of the device-to-room association system 20 includes a first microphone that is carried by the medical device and a second microphone that is spaced apart from the medical device. In some such embodiments of the device-to-room association system 20, the second microphone is configured to communicate wirelessly with the circuitry of the medical device.

In some embodiments, the circuitry 34 of the medical device of the device-to-room association system 20 further includes a display screen that displays the location ID after the circuitry 34 receives the location ID via the at least one microphone. Optionally, the circuitry 34 of the medical device of the device-to-room association system 20 is configured to wirelessly transmit the location ID and the bed ID for receipt by the at least one locating computer. Further optionally, the at least one locating computer stores a patient-to-location association and, after receipt of the medical device ID and location ID, may establish a device-to-patient association. In such embodiments, the at least one locating computer is configured to transmit to the medical device a patient ID corresponding to a patient to which the device-to-patient association pertains. If desired, the circuitry 34 of the medical device of the device-to-room association system 20 includes a display screen and the circuitry 34 is configured to display the patient ID on the display screen.

The present disclosure further contemplates that the circuitry 34 of the medical device of the device-to-room association system 20 is configured to generate a query to the person for additional information if the voice input does not include a valid location ID. For example, the circuitry 34 of the medical device of the device-to-room association system 20 further includes at least one speaker and the query includes an audible message played through the at least one speaker. Alternatively or additionally, the circuitry 34 of the medical device of the device-to-room association system 20 includes a display screen and the query includes a text message displayed on the display screen.

In some embodiments of the device-to-room association system 20, the circuitry of the medical device further includes a display screen and the circuitry 34 is configured to display a location menu of valid location ID's for the healthcare facility in response to a vocal request by the person. In this regard, the circuitry 34 of the medical device is configured to display a menu hierarchy relating to location options and the circuitry is configured to permit the person to navigate vocally through the menu hierarchy to reach the location menu.

Optionally, the circuitry 34 of the medical device of the device-to-room association system 20 includes at least one speaker and the circuitry 34 is configured to play an audible confirmation message through the at least one speaker in response to the location ID included in the voice input being a valid location ID. Further optionally, the circuitry 34 of the medical device of the device-to-room association system 20 is configured to receive a disassociate input from the person via the at least one microphone indicating that the first device-to-room association should be canceled. The circuitry 34 is configured to transmit the disassociate input to the at least one locating computer along with the medical device ID. The at least one locating computer is configured to cancel the first device-to-room association based on the medical device ID and the disassociate input transmitted from the medical device.

Figure 9:
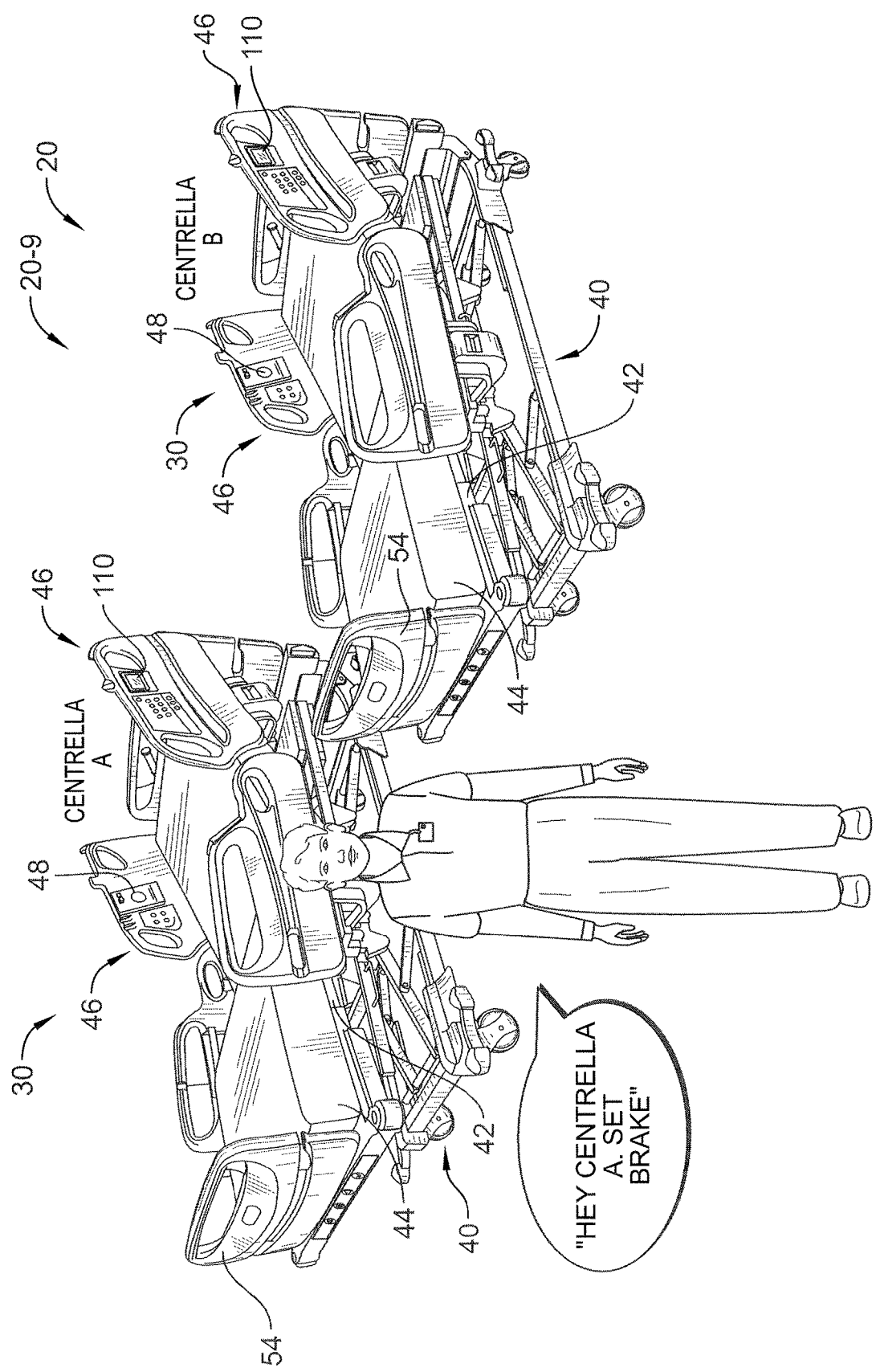
FIG. 9 is a diagrammatic view of a first way to determine which medical device from among multiple medical devices in a room is to be controlled by voice, showing a caregiver using a key phrase including a key word (e.g., "hey") followed by unique name (e.g., "bed name A") to indicate that bed A is to be controlled by the caregiver's voice and not bed B.

Referring now to FIG. 9, a system 20-9 has two patient beds 30 in a patient room. Thus, when a caregiver or patient attempts to vocally control one of the beds 30 in the room, it is desirable for system 20-9 to know which of the beds 30 is to be controlled based on the voice input. One of beds 30 is labeled diagrammatically as CENTRELLA A in the illustrative example and the other of beds 30 is labeled diagrammatically as CENTRELLA B. In system 20-9 of FIG. 9, a first way is shown for determining which medical device (e.g., patient bed 30 in the illustrative example) from among multiple medical devices in a room is to be controlled by voice. In particular, a caregiver uses a key phrase including a key word (e.g., "hey") followed by a unique name (e.g., "bed name A") to indicate that bed A is to be controlled by the caregiver's voice and not bed B. Thus, in the illustrative example, the caregiver's speech bubble indicates that the caregiver has spoken the voice input, "HEY CENTRELLA A. SET BRAKE." System 20-9 responds by setting the brake of the patient bed 30 labeled CENTRELLA A and does not set the brake of the patient bed 30 labeled CENTRELLA B. In FIG. 9, a graphical user interface (GUI) 110 is shown on one of the siderails 46 of each bed 30.

Based on the foregoing, therefore, the present disclosure contemplates that system 20-9 for voice control of medical devices in the room includes a first medical device having first circuitry 34 that includes a first processor 36, first memory 38, and a first microphone 48, and a second medical device having second circuitry 34 that includes a second processor 34, second memory 36, and a second microphone 48. The first and second medical devices of system 20-9 are in sufficiently close proximity to each other that a voice input spoken by a person is received by both of the first and second microphones 48. The first circuitry 34 of the first medical device is configured to become enabled for voice control in response to the voice input including a first code phrase and the second circuitry 34 of the second medical device is configured to become enabled for voice control in response to the voice input including a second code phrase.

In some embodiments of the system 20-9, the first code phrase and the second code phrase each may begin with a common code word. For example, the common code word may comprise the word "hey." Optionally, the first code phrase may include a first unique name that corresponds to the first medical device and that is spoken immediately after the common code word. Similarly, the second code phrase may include a second unique name that corresponds to the second medical device and that is spoken immediately after the common code word. In situations in which the first and second medical devices are of the same model name, the first unique name may be of the format "model name A" and the second unique name may be of the format "model name B." Alternatively or additionally, in situations in which the first and second medical devices are of the same model name, the first unique name may be of the format "model name 1" and the second unique name may be of the format "model name 2." The particular unique names for the first and second medical devices are stored in memory 38 of the respective medical devices in some embodiments of system 20-9 and/or are stored in a remote computer, such as the VCA computer of network 60.

After each of the first and second medical devices of system 20-9 becomes enabled for voice control, the respective first and second circuitry 34 is enabled for receiving voice commands to control functions of the respective first and second medical device for a threshold period of time, such as five seconds to one minute just to give a range of arbitrary threshold periods of time. After the threshold period of time elapses without the respective first and second medical device receiving at least one voice command, the respective first and second medical device becomes disabled from voice control, such as until another code phrase designating the particular medical voice control is received by a microphone of system 20-9. It is contemplated by the present disclosure that, in response to receiving a valid voice command during the threshold period of time, the threshold period of time is reset so that additional voice commands can be provided to the respective medical device if desired.

Figure 10:
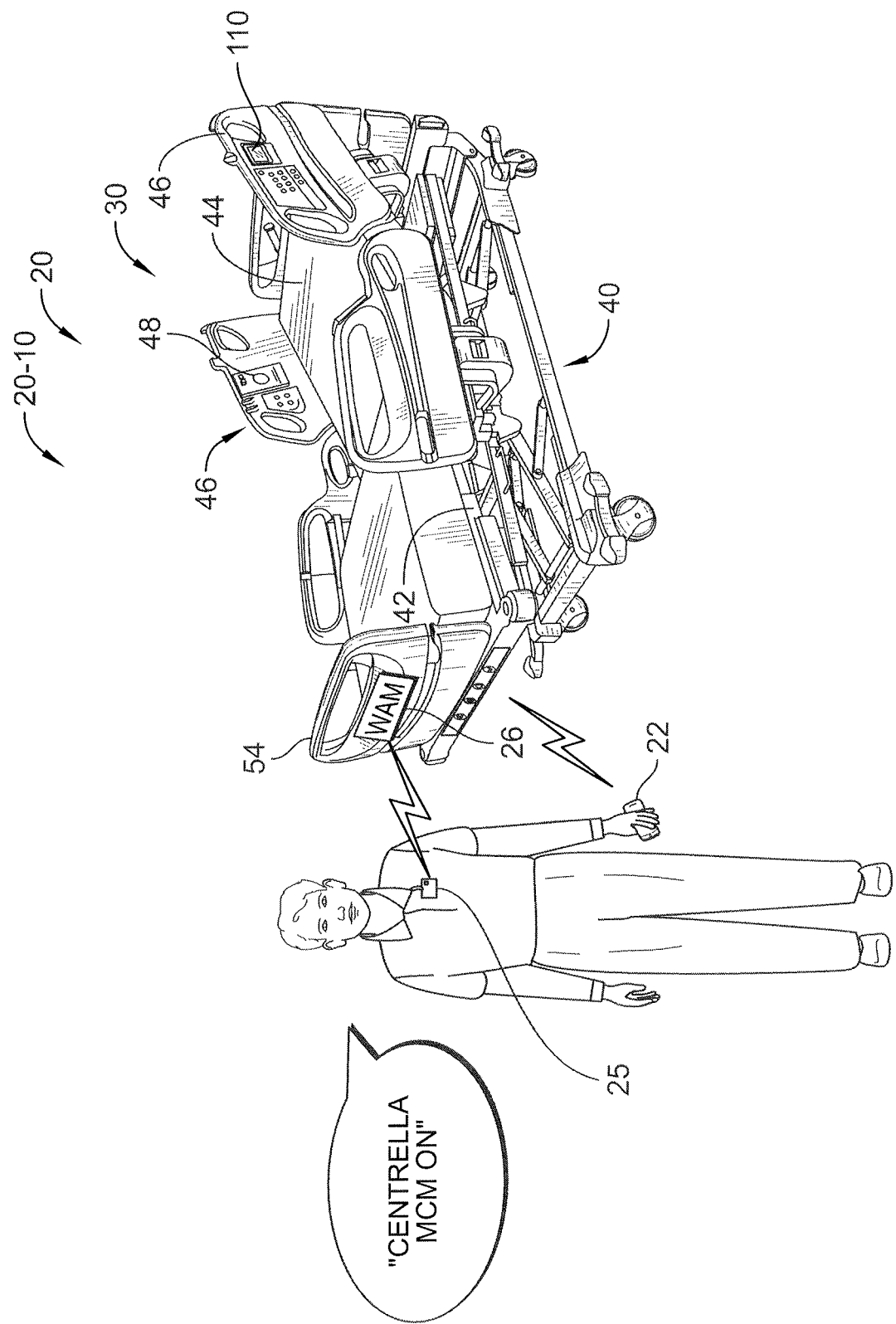
FIG. 10 is a diagrammatic view of a second way to determine which medical device from among multiple medical devices in a room is to be controlled by voice, showing a caregiver having a caregiver badge that emits a near field communication (NFC) signal that is detected by the medical device (e.g., the patient bed) when the caregiver is in close proximity to the medical device, the medical device being enabled for voice control in response to detection of the NFC signal.

Referring now to FIG. 10, a system 20-10 is shown in which caregiver badge 25 proximity to the medical device to be controlled by voice (e.g., patient bed 30 in the illustrative example) is used to determine which medical device from among multiple medical devices in the patient room is the one to be controlled. Thus, FIG. 10 is a diagrammatic view of a second way to determine which medical device from among multiple medical devices in a room is to be controlled by voice. In system 20-10 the caregiver badge 25 worn by the caregiver emits a near field communication (NFC) signal that is detected by the WAM 26 of the medical device (e.g., patient bed 30 in the illustrative example) when the caregiver is in close proximity to the medical device (e.g., on the order of three feet (1 meter) or less). The medical device becomes enabled by controller 34 for voice control in response to detection of the NFC signal from badge 25 by WAM 26 of the medical device. In the illustrative example, the caregiver's speech bubble indicates that the caregiver has spoken the voice input, "CENTRELLA MCM ON" while caregiver badge 35 is within close proximity of WAM 26. MCM is an acronym for a microclimate management feature of mattress 44 of bed 30.

Based on the foregoing, system 20-10 for enabling voice control of a medical device (e.g., patient bed 30) includes an identifier article (e.g., caregiver badge 25) carried by the caregiver and configured to transmit a wireless identification (ID) signal. System 20-10 also includes the medical device having circuitry 34 that includes a processor 36, memory 38, a microphone 48, a transmitter (e.g., included in WAM 26), and a proximity detector (e.g., also included in WAM 26) that is configured to receive the wireless ID signal from the identifier article 25 when the identifier article 25 is within three feet (1 m) or less of the medical device. System 20-10 further includes at least one voice control authorization (VCA) computer (e.g., VCA computer of network 60) that is remote from the medical device and that is communicatively coupled to the medical device. In response to receipt of the wireless ID signal by the proximity detector of the WAM 26, the circuitry 34 transmits via the transmitter of WAM 26 the ID data contained in the wireless ID signal for receipt by the VCA computer. The VCA computer is configured to verify that the ID data corresponds to a caregiver who is authorized to control the medical device via voice inputs. If caregiver authorization is verified by the VCA computer, the VCA computer is configured to transmit an authorization message to the medical device. In response to receipt of the authorization message by the circuitry 34 of the medical device via WAM 26, voice control of the medical device is enabled.

In some embodiments of system 20-10, the identifier article includes a mobile phone 22 in addition to or in lieu of the caregiver badge 25. In some embodiments of system 20-10 in which the identifier article is a caregiver badge 25, the identifier article is a radio frequency identification (RFID) badge. Further alternatively or additionally, the identifier article of system 20-10 may include a near field communication (NFC) transponder that emits the wireless ID signal in response to receipt of electromagnetic energy emitted by WAM 26 of the circuitry 34 of the medical device.

If desired, after voice control of the medical device is enabled, voice inputs received by the microphone 48 of the circuitry is transmitted by the transmitter of the circuitry to the VCA computer. In this regard, the VCA computer of system 20-10 is configured to determine that the voice input corresponds to at least one valid control command for the medical device from among a plurality of valid control commands. If the voice input corresponds to a valid control command of the plurality of valid control commands, the VCA computer is configured to transmit a device control message to the medical device. In response to receipt of the device control message by the circuitry 34 of the medical device, the medical device carries out a function corresponding to the device control message.

Optionally, after voice control of the medical device of system 20-10 becomes enabled, the circuitry 34 is enabled for receiving voice commands to control functions of the medical device for a threshold period of time, such as five seconds to one minute just to give a range of arbitrary threshold periods of time. After the threshold period of time elapses without the medical device of system 20-10 receiving at least one voice command, the medical device becomes disabled from voice control. It is contemplated by the present disclosure that, in response to receiving a valid voice command during the threshold period of time, the threshold period of time resets so that additional voice commands can be provided to the respective medical device if desired. In other embodiments of system 20-10, the circuitry 34 is enabled for receiving voice commands to control functions of the medical device for as long as the identifier article remains within communication range of WAM 26 of the medical device.

Figure 11:
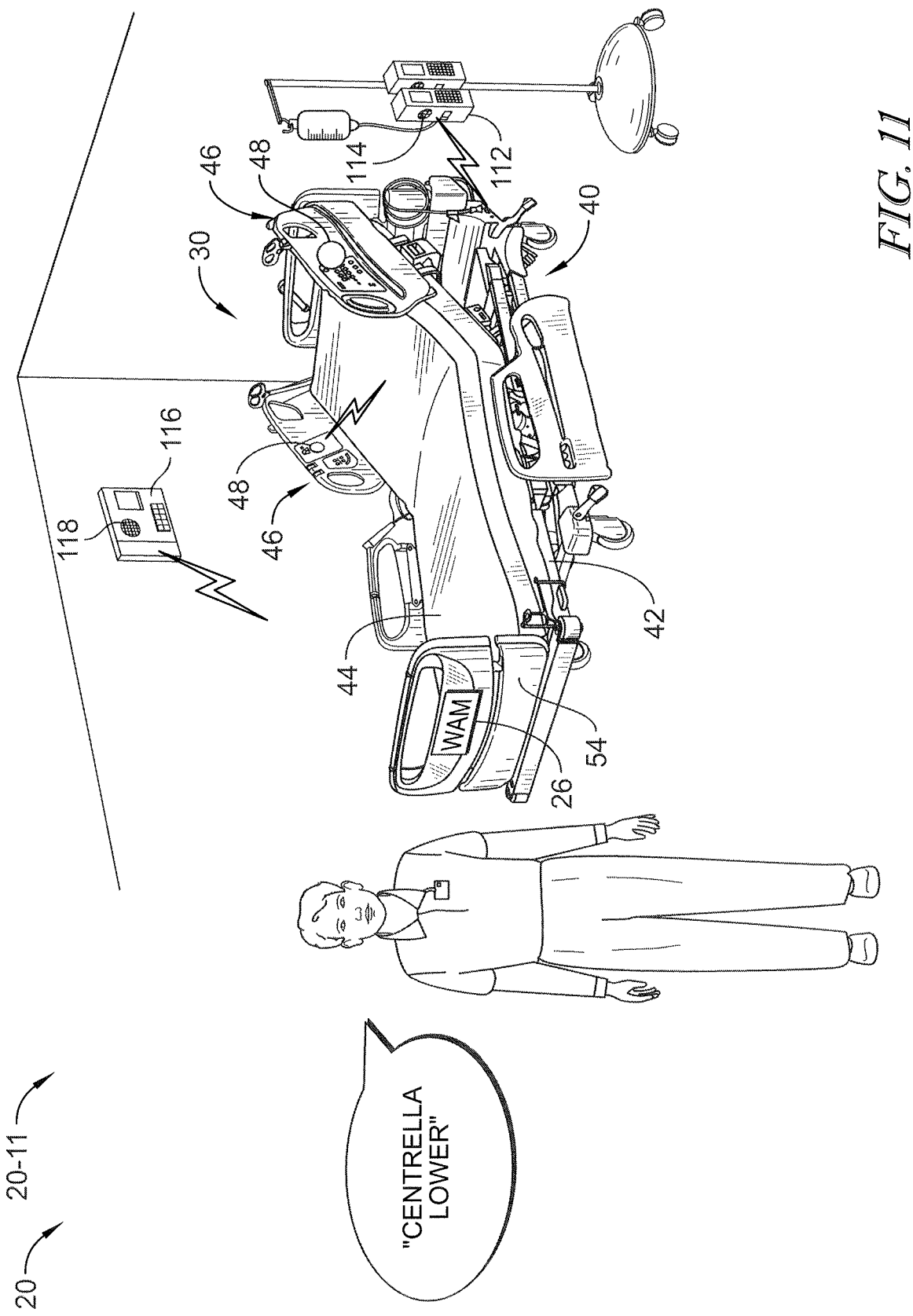
FIG. 11 is a diagrammatic view of a third way to determine which medical device from among multiple medical devices in a room is to be controlled by voice, showing a first microphone on a room wall, a second microphone on the patient bed, and a third microphone on a medical monitor, a remote server determining which medical device is to be voice controlled based on which of the first, second, and third microphones detects the loudest voice input from the caregiver.

Referring now to FIG. 11, a system 20-11 is shown in which a loudness of a voice input as received at each microphone of a plurality of microphones is used to determine which medical device from among multiple medical devices in the patient room is the one to be controlled by voice. Thus, FIG. 11 shows a diagrammatic view of a third way to determine which medical device from among multiple medical devices in a room is to be controlled by voice. In illustrative system 20-11 of FIG. 11, patient bed 30 has microphone 48, a second medical device 112 has a microphone 114, and a third medical device 116 has a microphone 118. Second medical device 112 is shown in FIG. 11 as an IV pump but just as well may be a vital signs monitor, therapy equipment, and the like. Third medical device 116 of the illustrative system 20-11 is an audio station of a nurse call system. Audio station 116 is mounted to a room wall at a fixed position whereas, bed 30 and IV pump 112 are mobile pieces of medical equipment that can be transported from location to location within the healthcare facility. In other embodiments of system 20-11 one or more speaker units 56 may be provided in the patient room in addition to microphones 48, 114, 118 or in lieu of microphones 48, 114, 118.

Based on the foregoing, system 20-11 for enabling voice control of a medical device 30, 112, 116 in a room includes a first medical device (e.g., one of devices 30, 112, 116) having first circuitry 34 including a first processor 36, first memory 38, and a first microphone (e.g., one of microphones 48, 114, 118), and a second medical device (e.g., another one of devices 30, 112, 116) having second circuitry 34 including a second processor 36, second memory 38, and a second microphone (e.g., another one of microphones 48, 114, 118). The first and second medical devices of system 20-11 are in sufficiently close proximity to each other that a voice input spoken by a person is received by both of the first and second microphones. The first circuitry of the first medical device is configured to become enabled for voice control in response to the voice input received by the first microphone being louder than the voice input received by the second microphone. The second circuitry of the second medical device is configured to become enabled for voice control in response to the voice input received by the second microphone being louder than the voice input received by the first microphone.

In some embodiments of system 20-11, the first circuitry is configured to transmit a first loudness value for receipt by the second circuitry and the second circuitry is configured to transmit a second loudness value for receipt by the first circuitry. The first medical device of system 20-11 is configured to become enabled for voice control in response to the first circuitry determining that the first loudness value is greater than the second loudness value. Similarly, the second medical device of system 20-11 configured to become enabled for voice control in response to the second circuitry determining that the second loudness value is greater than the first loudness value.

In some embodiments, system 20-11 further includes at least one voice control authorization (VCA) computer (e.g., VCA computer of network 60) that is remote from the first and second medical devices and that is communicatively coupled to the first and second medical devices. In such embodiments of system 20-11, the first circuitry is configured to transmit a first loudness value for receipt by the at least one VCA computer and the second circuitry is configured to transmit a second loudness value for receipt by the at least one VCA computer. The VCA computer is configured to transmit a first message to the first medical device which enables the first medical device for voice control in response to the VCA computer determining that the first loudness value is greater than the second loudness value. Similarly, the VCA computer is configured to transmit a second message to the second medical device which enables the second medical device for voice control in response to the VCA computer determining that the second loudness value is greater than the first loudness value.

Optionally, after each of the first and second medical devices of system 20-11 becomes enabled for voice control, the respective first and second circuitry 34 is enabled for receiving voice commands to control functions of the respective first and second medical device for a threshold period of time, such as five seconds to one minute just to give a range of arbitrary threshold periods of time. After the threshold period of time elapses without the respective first and second medical device of system 20-11 receiving at least one voice command, the respective first and second medical device becomes disabled from voice control. It is contemplated by the present disclosure that, in response to receiving a valid voice command during the threshold period of time, the threshold period of time resets so that additional voice commands can be provided to the respective medical device if desired.

In the illustrative example of system 20-11 described above, each medical device 30, 112, 116 had its own microphone 48, 114, 118, respectively. However, this need not be the case in other embodiments. Thus, according to a variant embodiment of systems 20-11, an array of microphones is located in the patient room but each microphone of the array is spaced apart from the medical devices that are capable of being controlled by voice. Thus, the present disclosure contemplates that the variant embodiment of system 20-11 includes a first medical device having first circuitry 34 that includes a first processor 36 and first memory 38 and a second medical device having second circuitry 34 that includes a second processor 36 and second memory 38. The variant embodiment of system 20-11 also has an array of microphones that is located in the room and that is spaced apart from the first and second medical devices.

In the variant embodiment of system 20-11, the array of microphones includes a first microphone that is closer to the first medical device than to the second medical device and a second microphone that is closer to the second medical device than to the first medical device. The first and second medical devices and first and second microphones of the variant embodiment of system 20-11, however, are in sufficiently close proximity to each other that a voice input spoken by a person is received by both of the first and second microphones. The first circuitry 34 of the first medical device of the variant embodiment of system 20-11 is configured to become enabled for voice control in response to the voice input received by the first microphone being louder than the voice input received by the second microphone. The second circuitry of the second medical device of the variant embodiment of system 20-11 is configured to become enabled for voice control in response to the voice input received by the second microphone being louder than the voice input received by the first microphone.

In some embodiments of system 20-11, the first microphone is included in first microphone circuitry that is configured to transmit a first loudness value for receipt by the first circuitry 34 of the first medical device and by the second circuitry 34 of the second medical device. The second microphone of such embodiments of system 20-11 is included in second microphone circuitry that is configured to transmit a second loudness value for receipt by the first circuitry 34 of the first medical device and by the second circuitry 34 of the second medical device. The first medical device of the variant embodiment of system 20-11 is configured to become enabled for voice control in response to the first circuitry 34 determining that the first loudness value is greater than the second loudness value. Similarly, the second medical device of the variant embodiment of system 20-11 tenth aspect is configured to become enabled for voice control in response to the second circuitry 34 determining that the second loudness value is greater than the first loudness value.

If desired, the array of microphones of the variant embodiment of system 20-11 includes communication circuitry that is coupled to the first and second microphones. The communication circuitry is configured to determine a first loudness value based on a first loudness of the voice input received by the first microphone and a second loudness value based on a second loudness of the voice input received by the second microphone. The communication circuitry is configured to transmit the first and second loudness values for receipt by the first circuitry 34 of the first medical device and by the second circuitry 34 of the second medical device. The first medical device of the variant embodiment of system 20-11 is configured to become enabled for voice control in response to the first circuitry 34 determining that the first loudness value is greater than the second loudness value. Similarly, the second medical device of the variant embodiment of system 20-11 is configured to become enabled for voice control in response to the second circuitry 34 determining that the second loudness value is greater than the first loudness value.

Optionally, the variant embodiment of system 20-11 further includes at least one voice control authorization (VCA) computer that is remote from the first and second medical devices and that is communicatively coupled to the first and second microphones of the array of microphones. The VCA computer receives a first loudness value that is based on a first loudness of the voice input received by the first microphone and a second loudness value that is based on a second loudness of the voice input received by the second microphone. The VCA computer is configured to transmit a first message to the first medical device which enables the first medical device for voice control in response to the VCA computer determining that the first loudness value is greater than the second loudness value. Similarly, the VCA computer is configured to transmit a second message to the second medical device which enables the second medical device for voice control in response to the VCA computer determining that the second loudness value is greater than the first loudness value.

Further optionally, after each of the first and second medical devices of the variant embodiment of system 20-11 becomes enabled for voice control, the respective first and second circuitry 34 is enabled for receiving voice commands to control functions of the respective first and second medical device for a threshold period of time, such as five seconds to one minute just to give a range of arbitrary threshold periods of time. After the threshold period of time elapses without the respective first and second medical device receiving at least one voice command, the respective first and second medical device of the variant embodiment of system 20-11 becomes disabled from voice control. It is contemplated by the present disclosure that, in response to receiving a valid voice command during the threshold period of time, the threshold period of time may reset so that additional voice commands can be provided to the respective medical device if desired.

Figure 12:
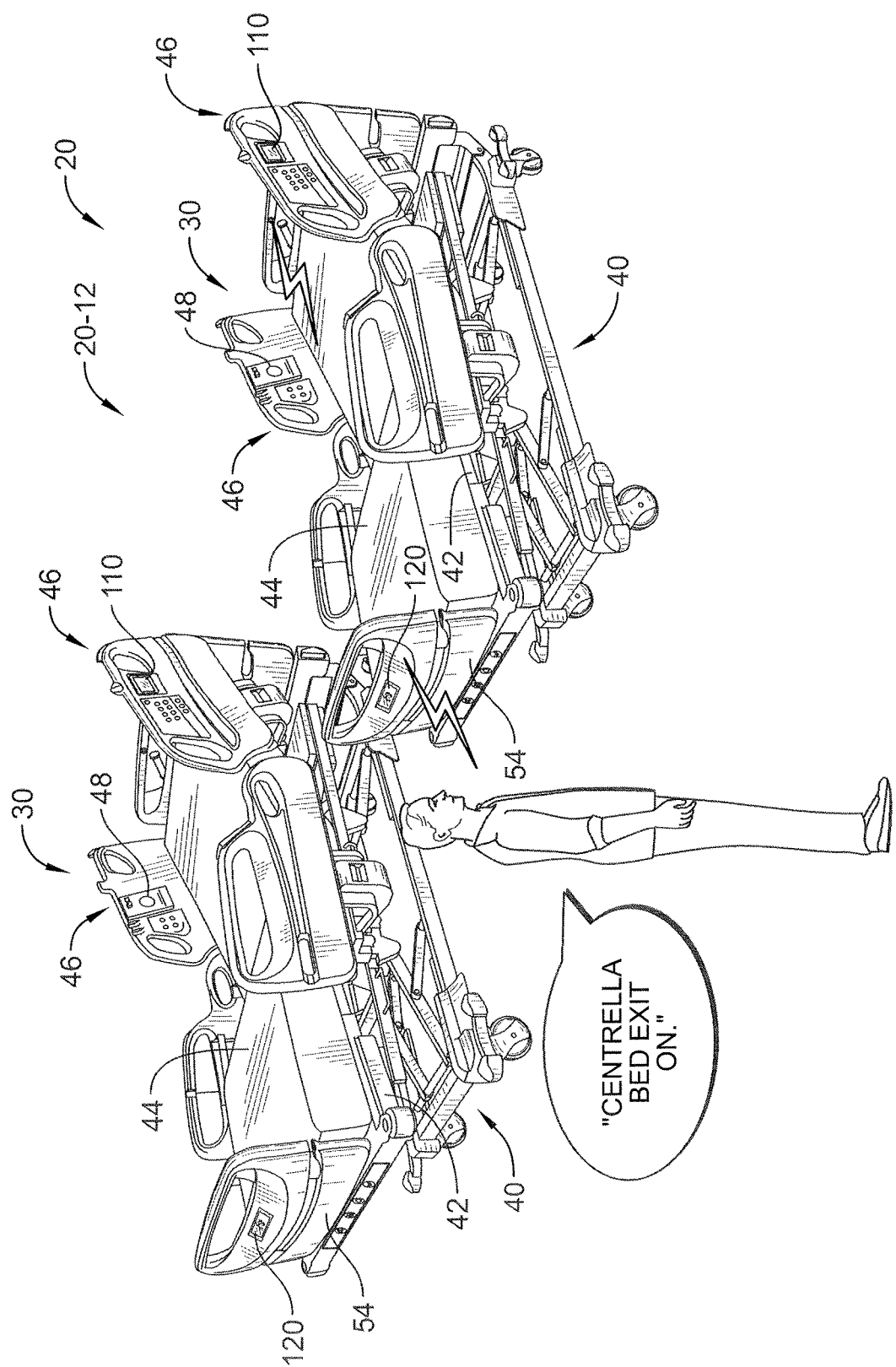
FIG. 12 is a diagrammatic view of a fourth way to determine which medical device from among multiple medical devices in a room is to be controlled by voice, showing a first medical device (e.g., first patient bed) having a first camera, a second medical device (e.g., second patient bed) having a second camera, and the medical device to be controlled by voice is the one at which the caregiver's face is captured by the respective camera.

Referring now to FIG. 12, a system 20-12 is shown in which cameras 120 are provided on medical devices in a patient room are used to determine which medical device from among multiple medical devices in the patient room is the one to be controlled by voice. Thus, FIG. 12 shows a diagrammatic view of a fourth way to determine which medical device from among multiple medical devices in a room is to be controlled by voice. In the FIG. 12 example of system 20-12 two patient beds 30 are each equipped with a respective camera 120. Cameras 120 are attached to footboards 54 of beds 30 in the illustrative example. Alternatively or additionally, cameras 120 are provided elsewhere on bed 30 such as being positioned on one or more of siderails 46 or on a headboard of bed 30. When a person provides a voice input to control a function of one of beds 30, the circuitry or controller 34 of each bed 30 processes an image captured by the respective camera 120 at the time the voice input is spoken to see if the person is looking at the camera 120.

In the illustrative example of system 20-12, the speech bubble in FIG. 12 indicates that the person has provided the voice input, "CENTRELLA BED EXIT ON" so as to turn on or enable the bed exit system of the bed in the foreground of FIG. 12. The person is looking at camera 120 of the bed 30 in the foreground of FIG. 12 and not the camera 120 of the bed 30 in the background of FIG. 12. Thus, when the voice input is spoken, the camera 120 of the bed 30 in the foreground captures an image of the person's face while the camera 120 of the bed 30 in the background captures an image that is devoid of any person's face. The controller 34 of each bed 30, or a remote computer such as the VCA computer of network 60, processes the captured image of the respective camera 120 to determine whether or not the voice input pertains to that particular bed. In the illustrative example, the bed 30 of system 20-12 in the foreground carries out the voice input (e.g., enables the respective bed exit system) after controller 34 determines, or has been notified, that the captured image contains a person's face.

Based on the foregoing, therefore, the present disclosure contemplates that system 20-12 includes a first medical device (e.g., one of beds 30 in FIG. 12) having first circuitry 34 that includes a first processor 36, first memory 38, a first microphone 48, and a first camera 120, and a second medical device (e.g., the other of beds 30 in FIG. 12) having second circuitry 34 that includes a second processor 36, second memory 38, a second microphone 48, and a second camera 120. The first circuitry 34 of the first medical device of system 20-12 is configured to become enabled for voice control in response to the first processor 36 recognizing a first image of a face of a person as captured by the first camera 120. Similarly, the second circuitry 34 of the second medical device of system 20-12 is configured to become enabled for voice control in response to the second processor 36 recognizing a second image of the face of the person as captured by the second camera 120.

In some embodiments of system 20-12, the first camera 120 captures the first image of the person for processing by the processor 36 in response to the first microphone 48 receiving a voice command from the person and the second camera 120 captures the second image of the person for processing by the processor 36 in response to the second microphone 48 receiving the voice command from the person. The voice command may include any valid device control command from among a plurality of valid device control commands, for example.

Optionally with regard to system 20-12, the first circuitry 34 further includes a first display screen 110 and the second circuitry 34 further includes a second display screen 110. If the first and second cameras 120 both capture the respective first and second images of the face of the person in response to the voice commands, the first and second medical devices 30 both remain disabled from voice control and the first and second display screens 110 each displays a notification message advising the person to face only the first or second camera 120 of the respective first or second medical device 30 that the person wishes to control by voice. To determine that cameras 120 of both beds 30 have captured an image of the person's face, beds 30 communicate appropriate messages to each other, such as through an in-room network, or directly via the WAM's 26 of the beds 30, or via network 60. Alternatively or additionally, a remote computer of network 60 sends notification messages to beds 30 indicating that both cameras 120 have captured an image of the person's face and therefore, it is not known which of beds 30 is the one that is to be voice controlled by the person. To accomplish this, each image captured by the cameras 120 is time stamped so that images captured at the same time or within a very short time threshold apart (e.g., less than one second) can be detected.

In some embodiments of system 20-12, the first medical device comprises a first patient bed 30 that has a first patient egress barrier (e.g., siderail 46 or footboard 54) to which the first camera 120 is coupled and the second medical device comprises a second patient bed 30 that has a second patient egress barrier (e.g., siderail 46 or footboard 54) to which the second camera 120 is coupled. For example, the first and second patient egress barriers each include a respective first and second headboard or a respective first and second footboard 54. Alternatively or additionally, the first and second patient egress barriers each comprise a respective first and second siderail 46. Optionally, the first circuitry 34 further includes a first display screen 110 coupled to the first siderail 46, the second circuitry further includes a second display screen 110 coupled to the second siderail 46, the first camera 120 is situated adjacent the first display screen 110, and the second camera 120 is situated adjacent the second display screen 110.

If desired, system 20-12 further includes at least one voice control authorization (VCA) computer that is remote from the first and second medical devices and that is communicatively coupled to the first and second medical devices. In such embodiments, the first circuitry 34 is configured to transmit the first image for receipt by the at least one VCA computer, such as by a transmission via WAM 26 of the first medical device, and the second circuitry 34 is configured to transmit the second image for receipt by the at least one VCA computer, such as by a transmission via WAM 26 of the second medical device. The VCA computer of system 20-12 is configured to transmit a first message to the first medical device which enables the first medical device for voice control in response to the VCA computer determining that the person is authorized to operate the first medical device by voice control based on analyzing the first image. Similarly, the VCA computer is configured to transmit a second message to the second medical device which enables the second medical device for voice control in response to the VCA computer determining that the person is authorized to operate the second medical device by voice control based on analyzing the second image.

Optionally, after each of the first and second medical devices of system 20-12 becomes enabled for voice control, the respective first and second circuitry 34 is enabled for receiving voice commands to control functions of the respective first and second medical device for a threshold period of time, such as five seconds to one minute just to give a range of arbitrary threshold periods of time. After the threshold period of time elapses without the respective first and second medical device of system 20-12 receiving at least one voice command, the respective first and second medical device become disabled from voice control. It is contemplated by the present disclosure that, in response to receiving a valid voice command during the threshold period of time, the threshold period of time may reset so that additional voice commands can be provided to the respective medical device if desired.

Figure 13:
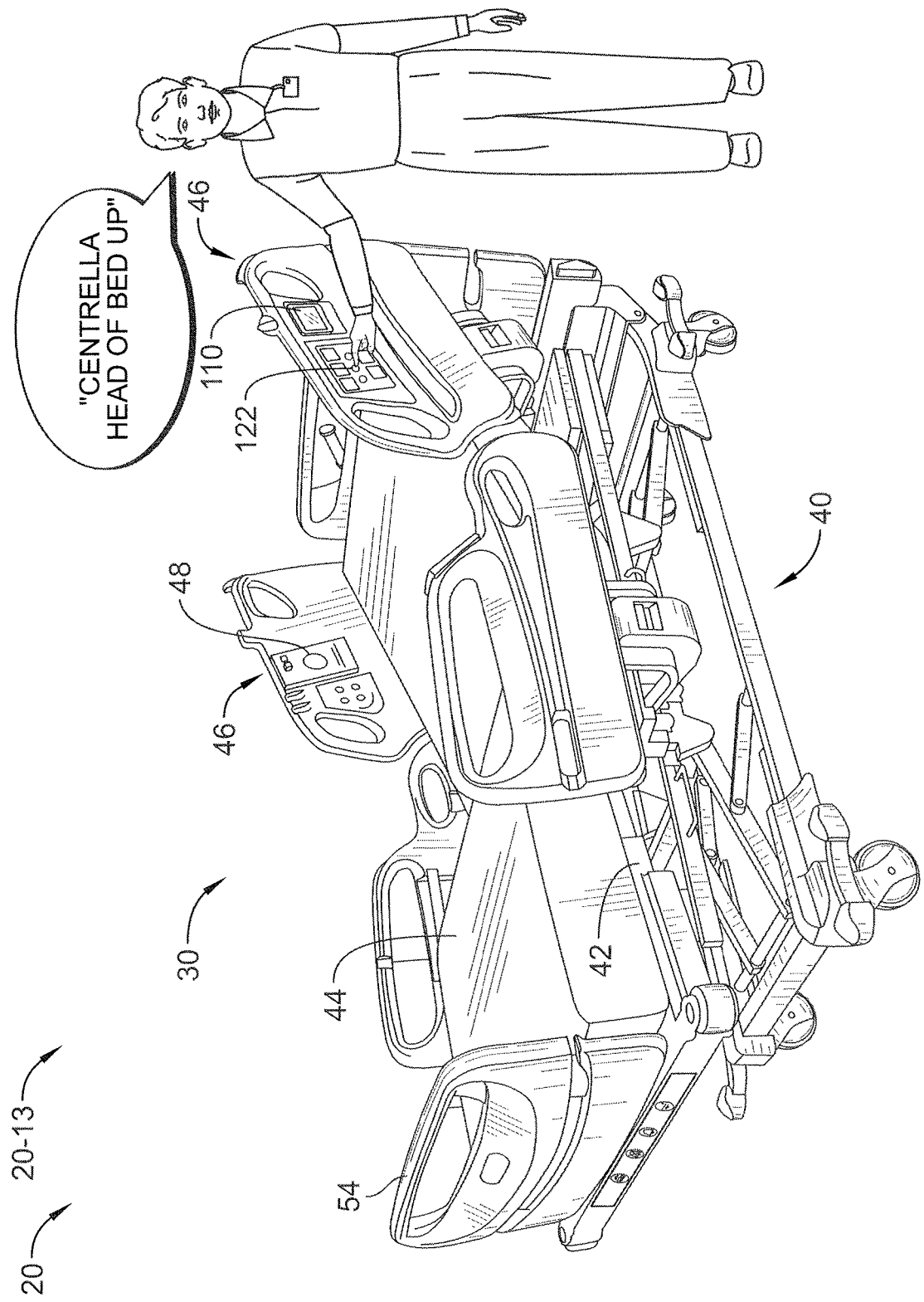
FIG. 13 is a diagrammatic view of a fifth way to determine which medical device from among multiple medical devices in a room is to be controlled by voice showing, the caregiver pressing a button on the medical device (e.g., a button one of the siderails of the patient bed) to enable the medical device for voice control while the button is pressed or for a threshold period of time after the button is pressed.

Referring now to FIG. 13, a system 20-13 is shown in which a caregiver presses a button 122 on the medical device (e.g., a button on one of the siderails of the patient bed 30) to enable the medical device for voice control while the button 122 is pressed or for a threshold period of time such as five seconds to one minute after the button 122 is pressed. Thus, FIG. 13 shows a diagrammatic view of a fifth way to determine which medical device from among multiple medical devices in a room is to be controlled by voice. While only one medical device, illustratively patient bed 30, is shown in FIG. 13, it should be understood that system 20-13 includes other medical devices in the patient room that also include buttons 122 thereon for selection in regard to entry of voice inputs to the respective medical device. While requiring button 122 be pressed on a medical device to enable voice control has the drawback of not allowing for entirely hands-free control of the medical device, it does still have the advantage of not requiring the user to navigate through a complex screen menu hierarchy using GUI 110 to reach particular controls for device functions.

Based on the foregoing, the present disclosure contemplates that system 20-13 includes a medical device having first circuitry 34 that includes a processor 36, memory 38, a button 122, and a microphone 48. The circuitry 34 of the medical device of system 20-13 is configured to become enabled for voice control in response to the button 122 being selected by a person and then, thereafter, receiving a valid voice input via the microphone 48 within a threshold period of time such as within five seconds to one minute just to give an arbitrary time threshold range.

In some embodiments of system 20-13, the valid voice input includes a code word. For example, the code word may include a first unique name that corresponds to the medical device and that is received by the microphone 48 within the threshold period of time. Optionally, the unique name may comprise a model name of the medical device. If desired, after the medical device of system 20-13 becomes enabled for voice control due to receipt of the code word during the threshold period of time (e.g., the first threshold period of time), the respective circuitry 34 is enabled for receiving voice commands to control functions of the medical device for a second threshold period of time such as within five seconds to one minute just to give an arbitrary time threshold range. After the second threshold period of time elapses without the medical device receiving at least one voice command, the medical device becomes disabled from voice control. It is contemplated by the present disclosure that, in response to receiving a valid voice command during the second threshold period of time, the second threshold period of time is reset so that additional voice commands can be provided to the respective medical device if desired.

In some embodiments of system 20-13, the valid voice input includes any device control command from among a plurality of device control commands. The present disclosure contemplates that the medical device of system 20-13 remains disabled from being voice controlled if the valid voice input is not received within the threshold period of time.

Figure 14:
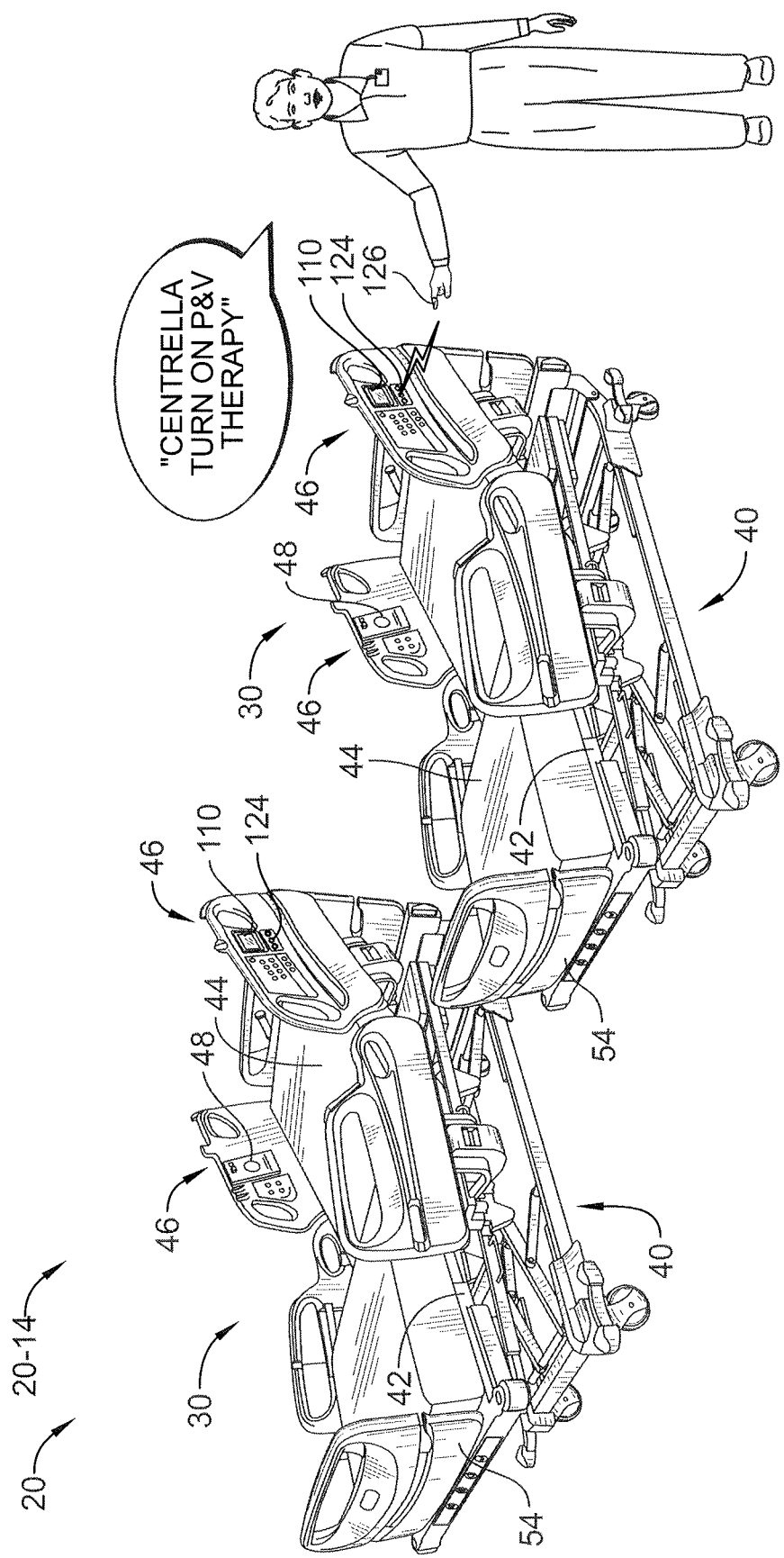
FIG. 14 is a diagrammatic view of sixth way to determine which medical device from among multiple medical devices in a room is to be controlled by voice showing, the caregiver having an IR pointer which transmits an IR signal toward an IR receiver of the medical device (e.g., the patient bed) to be voice controlled, the medical device becoming enabled for voice control for a threshold period of time in response to detection of the IR signal by the respective IR receiver.
Figure 15:
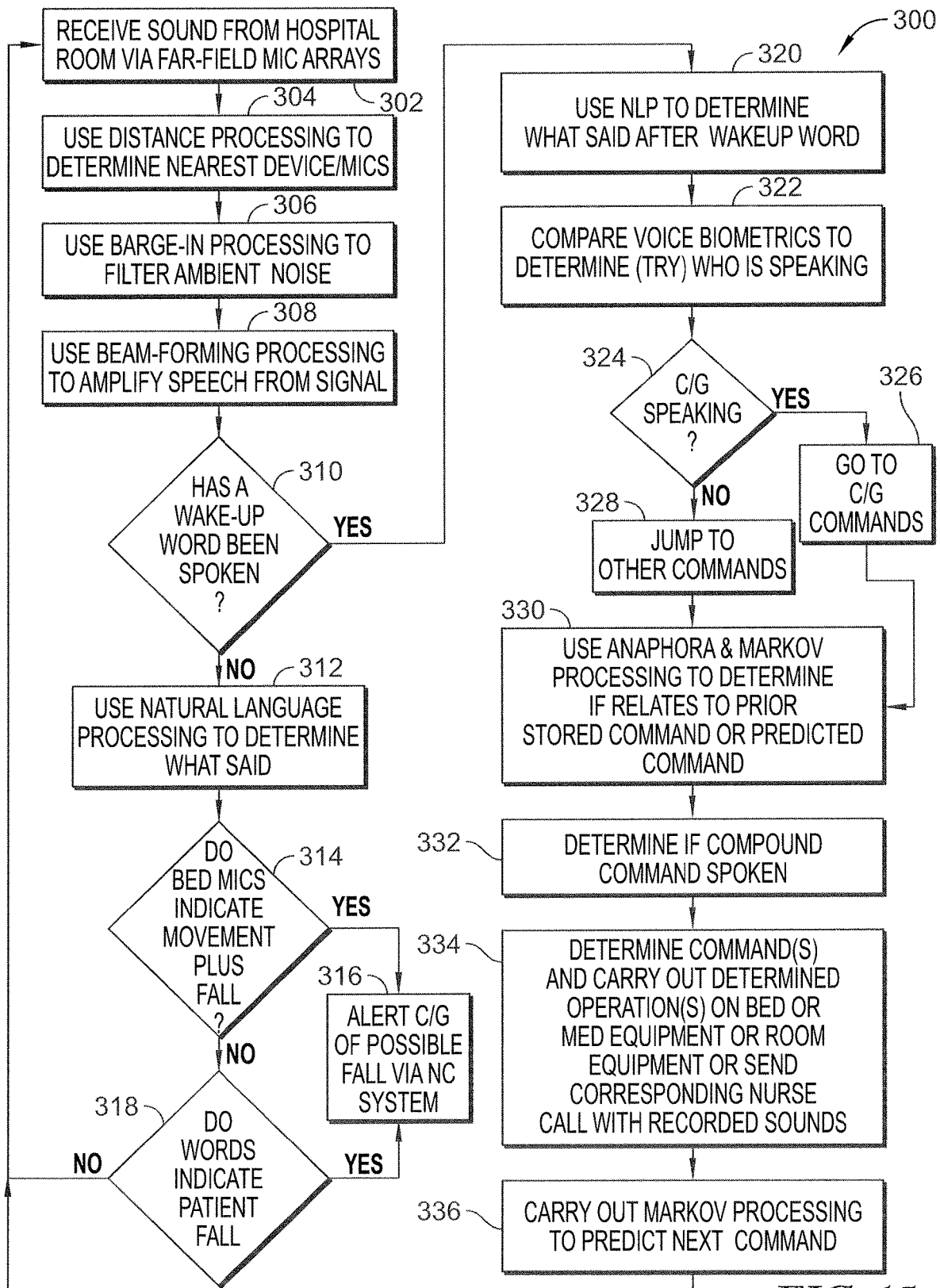
FIG. 15 is a flow chart of an algorithm for control of a medical device by voice inputs, showing the algorithm including instruction to: (i) combine voice inputs received from a person by an array of far-field microphones in a room, (ii) amplify and discern voice inputs using beam-forming software, (iii) filter out ambient noise using barge-in software, (iv) execute speech recognition software to determine which medical device of a plurality of medical devices is a designated medical device to be controlled by the voice inputs, and (v) transmit a control message to the designated medical device to control a first function of the designated medical device based on the voice inputs.

Referring now to FIG. 14, a system 20-14 is shown in which a caregiver has an IR pointer 126 which transmits an IR signal toward an IR receiver 124 of the particular medical device (e.g., the patient bed 30) to be voice controlled. Thus, FIG. 14 shows a diagrammatic view of sixth way to determine which medical device from among multiple medical devices in a room is to be controlled by voice. In response to the receiver 124 receiving the IR signal from the IR pointer 126, the medical device becomes enabled for voice control for a threshold period of time. In the illustrative example, IR pointer 126 is sized and shaped to fit onto a person's finger. In other embodiments, the IR pointer 126 is configured to be mounted to mobile phone 22, or is shaped like a writing pen or stylus, or is shaped like a key fob. Optionally, the IR pointer 126 is mounted to or included in the caregiver badge 25. A button is provided on the IR pointer 126 and is pressed to send the IR signal from the IR pointer 126.

Based on the foregoing, system 20-14 includes a first medical device that has first circuitry 34 including a first processor 36, first memory 38, a first microphone 48, and a first infrared (IR) receiver 124, and a second medical device having second circuitry 34 that has a second processor 36, second memory 38, a second microphone 48, and a second IR receiver 124. The system 20-14 further includes an IR pointer 126 having an IR transmitter. The first circuitry 34 of the first medical device is configured to become enabled for voice control in response to the first IR receiver 124 receiving an IR signal from the IR transmitter of the IR pointer 126. The second circuitry 34 of the second medical device is configured to become enabled for voice control in response to the second IR receiver 124 receiving the IR signal from the IR transmitter of the IR pointer 126.

In some embodiments of system 20-14, the IR pointer 126 is configured to be worn on a finger of a person. Alternatively or additionally, the IR pointer 126 is mountable to mobile phone 22. Further alternatively or additionally, the IR pointer 126 has a shape of a handwriting pen. Still further alternatively or additionally, the IR pointer 126 has a shape of a key fob.

It is contemplated by the present disclosure that the first medical device of system 20-14 comprises a first patient bed 30 has a first patient egress barrier (e.g., siderail 46 or footboard 54 or the headboard) to which the first IR receiver 124 is coupled and the second medical device 30 of the system 20-14 comprises a second patient bed 30 that has a second patient egress barrier to which the second IR receiver 124 is coupled. For example, the first and second patient egress barriers each include a respective first and second headboard or a respective first and second footboard. Alternatively or additionally, the first and second patient egress barriers each include a respective first and second siderail 46. In such embodiments, the first circuitry 34 further includes a first display screen 110 coupled to the first siderail 46, the second circuitry 34 further includes a second display screen 110 coupled to the second siderail 46, the first IR receiver 124 is situated adjacent the first display screen 110, and the second IR receiver 124 is situated adjacent the second display screen 110.

If desired, after each of the first and second medical devices of the system 20-14 becomes enabled for voice control, the respective first and second circuitry 34 is enabled for receiving voice commands to control functions of the respective first and second medical device for a threshold period of time, and after the threshold period of time elapses without the respective first and second medical device receiving at least one voice command, the respective first and second medical device becomes disabled from voice control. It is contemplated by the present disclosure that, in response to receiving a valid voice command during the threshold period of time, the threshold period of time may reset.

According to the present disclosure, far field microphones are embedded in vital signs monitors, hospital beds, headwall interfaces, caregiver badges, locating tags, disposable patient ID bracelets and/or gowns, and chairs, to form a hospital room microphone array. At least one remote computer combines voice signals received from these devices. Beamforming software is used to amplify and/or discern the voice signals. Barge-in software is used to filter out constant ambient audio which may correspond to background noise. Automatic speech recognition software is used to determine a code word or a wake word (e.g., "Hey Hillrom," "Hey Centrella," "Hey Voalte," "Hey Navicare," just to name a few). Additional processing such as via Anaphora Resolution, Markov Models, Speaker Recognition/Voice Biometrics, Compound Command Parsing, Natural Language Processing algorithms are also used in some embodiments of system 20 according to the present disclosure.

Combinations of the features set forth above, and/or some subcombinations are included in embodiments of system 20. In this regard, far-field microphones are dispersed throughout patient rooms. In some embodiments, the far-field microphones are an array of mics that use their location in space to amplify and reduce signals. In connection with suppressing surrounding noises, the array of far-filed microphones use algorithms to help deliver a clear signal. The mics can be embedded in bed electronics, vital signs monitor electronics, locating/tracking tags, headwall interfaces, graphical audio stations on walls, ceiling equipment, and/or hospital patient lifts at the discretion of the system designer. In some embodiments, each microphone actually includes a microphone array such as comprising a single piece of hardware with multiple individual microphones operating in tandem.

The present disclosure contemplates that electronics/computer/circuitry, in the room and/or located remotely, has software which processes and enhances the signals and determines what clinical action to take or patient request action to take. The present disclosure further contemplates that this software includes speech recognition/ASR conversion of spoken language into written text, code word/wake word recognition (e.g., Hey Centrella, Hey Navicare, Hey Voalte, Hey Nurse, Hey . . . etc.) such that the words following the code word or wake word are picked up. The software of system 20 also is configured for comparison of the voice command to a database of acceptable hospital commands and words to see if something is being commanded; and if commanded, to carry out the command in the table; and if not commanded, try to determine if it is a sign of patient or caregiver distress.

In some embodiments, distance processing is employed in system 20. For example, if the distance between the microphones is known (e.g., the software knows the distance between a headwall microphone and a graphical audio station microphone on the wall), then the software factor such distances into determining what was spoken/heard by the microphones. With regard to the barge-in technology used in system 20, the software determines what constant/ ambient noises are in the room (e.g., due to the time that the signal is being heard, its volume, its signature, its frequency, etc.). The barge-in software filters out the constant sound to best capture the spoken commands. The beam-forming software enables the microphones to amplify speech and reduce noise, as well.

According to the present disclosure, speaker recognition software of system 20 is used to determine who is speaking. This can be achieved from the characteristics of voices and a variety of technologies including Markov models, pattern recognition algorithms, neural networks, and voice biometrics. This software includes algorithms to perform the functions of (i) verification which aims to verify if the speaker is who they claim to be, and (ii) identification including the task of determining an unknown speaker's identity. Markov Models software relates to randomly changing systems to forecast future states. Such software tries to determine what the speaker said via context, what was said prior, the environment, the initial words and what typically follows those words, etc. Thus, the software in some embodiments of the present disclosure relates to pattern recognition, artificial neural networks, and natural language processing (NLP) and/or natural language understanding. In this regard, the NLP software analyzes, understands and derives meaning from what is spoken. Thus, the NLP software can pick up and understand a wide array of similar commands intended to mean the same thing and can convert them into a structured form to carry out the single command being conveyed.

Systems 20 contemplated herein also use anaphora resolution software n some embodiments. Such software allows system 20 to recalls what was said earlier and uses that to infer what is currently intended. For example, if the patient says, "turn on the TV" and then later says, "turn it up," the software can use this technique to know that the TV is what is intended to be turned up. Some embodiments of system 20 are configured with the ability to recognize compound commands. For example, if the patient says, "turn off the TV and call the nurse," the text is parsed to understand that two commands are actually intended—turning off the TV command causes TV to turn off, call the nurse command causes the nurse call signal to be placed over the nurse call line. Accordingly the present disclosure contemplates that system 20 may serve as a virtual assistant or chatbot that is able to perform tasks for the patient. Therefore, the medical devices described above may include a Voice User Interface (VUI) for carrying out these functions.

Based on the foregoing, a flow chart of an algorithm 300 for control of a medical device by voice inputs is shown in FIG. 15. Broadly speaking, algorithm includes instructions to: (i) combine voice inputs received from a person by an array of far-field microphones in a room, (ii) amplify and discern voice inputs using beam-forming software, (iii) filter out ambient noise using barge-in software, (iv) execute speech recognition software to determine which medical device of a plurality of medical devices is a designated medical device to be controlled by the voice inputs, and (v) transmit a control message to the designated medical device to control a first function of the designated medical device based on the voice inputs. The instructions of algorithm 300 are executed by one or more of the bed controller 34, speaker unit 56, or the VCA computer of network 60. Thus, not all portions of algorithm 300 need to be performed on a single computer device but that is not rule out such a possibility in some embodiments of system 20.

Still referring to FIG. 15, algorithm 300 starts at block 302 where an array of far-field microphones (e.g., microphones 48, 56, 114, 118) receive sound in a hospital room. Algorithm 300 then uses distance processing to determine the nearest medical device or mics that are picking up the sound as indicated at block 304. Thereafter, algorithm 300 uses barge-in software to filter ambient noise out of the incoming voice signal as indicated at block 306. Next, algorithm 300 uses beam-forming processing to amplify speech from the signal corresponding to the detected sound as indicated at block 308. At block 310, algorithm 300 determines whether a wake-up word has been spoken.

If at block 310 it is determined that a wake-up word has not been spoken, algorithm 300 proceeds to block 312 and uses natural language processing (NLP) to determine what was said. At block 314, algorithm 300 determines whether the sound detected by the array of microphones 48 of bed 30 indicate movement of the patient plus a fall by the patient. If patient movement and fall are detected at block 314, the algorithm proceeds to block 316 to alert one or more caregivers of the fall via a nurse call system. The nurse call system sends an alert message in this regard to mobile phone 22 of the one or more caregivers being alerted, for example. A dome light near the door of the patient room is also illuminated to indicate the alert condition in the room in some embodiments of the nurse call system. An electronic whiteboard at a master station of the nurse call also displays the alert condition regarding possible patient fall in some embodiments.

If the bed mics 48 do not indicate movement plus a fall at block 314, algorithm 300 proceeds to block 318 and determines whether words detected by the array of microphones indicate a patient fall. If the words do indicate a fall at block 318, then algorithm proceeds to block 316 to alert one or more caregivers of the possible fall via the nurse call system as described above. If words do not indicate a fall at block 318, then algorithm 300 returns back to block 302 and proceeds from there as described herein.

If at block 310 algorithm 300 determines that a wake-up word has been spoken, the algorithm 300 proceeds to block 320 at which NLP is used to determine what was said after the wake-up word was spoken. Thereafter, algorithm 300 proceeds to block 322 and determines (or tries to determine) who is speaking based on a comparison of the voice information to voice biometrics of authorized users stored in a database, such as in a database of the VCA computer or in memory 38 of bed controller 34. Next, algorithm 300 proceeds to block 324 and determines whether a caregiver is speaking.

If algorithm 300 determines that a caregiver is speaking at block 324, then algorithm 300 proceeds to block 326 and goes to a library of caregiver commands. If algorithm 300 determines that a caregiver is not speaking at block 324, then algorithm 300 proceeds to block 328 and jumps to a library of other commands. Thus, the present disclosure contemplates that caregivers are permitted to voice control more features of the medical devices in the room than the patient or other non-caregivers (e.g., visitors) are permitted to voice control.

After each of blocks 326, 328, algorithm 300 proceeds to block 330 and uses anaphora processing and Markov processing to determine if the detected speech relates to a prior stored command or to a predicted command. Thereafter, algorithm 300 proceeds to block 332 to determine if a compound command was spoken. Algorithm 300 then proceeds to block 334 and determines what the particular command(s) are and carries out the bed operation(s), other medical device operation(s), or room equipment (e.g., environment equipment or entertainment equipment) operations based on the identified command or commands. A nurse call with recorded sounds also may be sent in connection with block 334 of algorithm 300 in appropriate situations in some embodiments of system 20. After the command or commands are carried out at block 334, algorithm 300 proceeds to block 336 to carry out Markov processing to predict the next command that may be spoken by a user. After block 336, algorithm 300 returns to block 302 and proceeds from there as described herein.

It should be appreciated that any of systems 20-9, 20-10, 20-11, 20-12, 20-13, 20-14 can be implemented in any of systems 20-1, 20-2, 20-3, 20-4, 20-5, 20-6. Moreover, all combinations and permutations of systems 20-1, 20-2, 20-3, 20-4, 20-5, 20-6, 20-9, 20-10, 20-11, 20-12, 20-13, 20-14 are contemplated as being within the scope of the present disclosure. In this regard, use of the reference number 20 by itself without any hyphenated suffix covers all embodiments of systems 20-1, 20-2, 20-3, 20-4, 20-5, 20-6, 20-9, 20-10, 20-11, 20-12, 20-13, 20-14 disclosed herein. Furthermore, the present disclosure contemplates that when medical devices, such as illustrative bed 30, are enabled for voice control, a visual or audible indicator is provided in this regard. Thus, an indicator light on the medical device is illuminated in some embodiments to notify the user (e.g., caregiver or patient) that the medical device is ready to receive voice inputs for controlling functions of the device. Alternatively or additionally, a message or icon is shown on the display screen 110 of the medical device and/or on the user's mobile phone 22, 22' to notify the user that the medical device is ready to receive voice inputs for controlling functions of the device. Further alternatively or additionally, an audible message, such as "ready for voice control," is played through a speaker 48 or other sound-producing element of the medical device or speaker unit 46 or through a speaker of the user's mobile phone 22, 22'.

The present disclosure contemplates that one or more of the following voice commands, given only as a non-exhaustive list of examples, are used to control patient bed 30 in some embodiments of each system 20 described above:

TABLE 1

| Type of command | Example voice command | Resulting action software causes on bed |
| --- | --- | --- |
| Bed hi lo | "Bed Name, low and flat" | Causes bed articulation actuators to put bed deck flat and the bed hilo actuators to lower the deck/upper frame all the way to its lowest height relative to the lower frame |
| Bed hi lo | "Bed Name, high" | Causes bed hilo actuators to raise the deck/upper frame all the way to its highest height relative to the lower frame |
| Bed hi lo | "Bed Name, low" | Causes bed hilo actuators to lower the deck/upper frame all the way to its lowest height relative to the lower frame |
| Bed deck articulation | "Bed Name, flat" | Causes bed articulation actuators to put bed deck flat |

TABLE 1-continued

| Type of command | Example voice command | Resulting action software causes on bed |
| --- | --- | --- |
| Bed deck articulation | "Bed Name, head 30 degrees" | Causes head of bed (HOB) bed articulation actuator to put HOB head deck section to 30 degrees, as controlled by fb from potentiometer on actuator or accelerometer on HOB deck section |
| Bed deck articulation | "Bed Name, head flat" | Causes head of bed (HOB) bed articulation actuator to put HOB head deck section horizontal/flat, as controlled by fb from potentiometer on actuator or accelerometer on HOB deck section |
| Bed deck articulation | "Bed Name, chair egress" | Causes head of bed (HOB) bed articulation actuator to raise to max angled (up) position, bed to lift, bed foot section to drop to most angled (downward) position, bed foot section to retract, bed to tilt forward (as controlled by reverse Trend algorithm/actuators), all, as controlled by fb from potentiometer on actuators or accelerometers on deck sections; And causes seat bladder to be maximum inflated as controlled by the surface pump system |
| Bed deck articulation | "Bed Name, foot down" | Causes bed foot section to drop to most angled (downward) position as controlled by fb from potentiometer on foot actuator or accelerometers on foot deck section |
| Bed deck articulation | "Bed Name, foot flat" | Causes bed foot section to raise to horizontal position, as controlled by fb from potentiometer on foot actuator or accelerometer on foot deck section |
| Bed deck articulation | "Bed Name, knee up" | Causes bed thigh section to raise to max up position, as controlled by fb from potentiometer on thigh actuator or accelerometer on thigh deck section |
| Bed deck articulation | "Bed Name, knee down" | Causes bed thing section to drop to max down/horizontal position, as controlled by fb from potentiometer on thigh actuator or accelerometer on thigh deck section |
| Bed deck articulation | "Bed Name, vascular" | Causes foot section to raise to max up position, thigh section to raise to up position, and bed to tilt into Trendelenburg position, as controlled by fb from potentiometer on corresponding actuators and/or accelerometers on deck sections |
| Bed deck articulation | "Bed Name, full chair" | Causes head of bed (HOB) bed articulation actuator to raise to max angled (up) position, bed foot section to drop to most angled (downward) position, all as controlled by fb from potentiometer on actuators or accelerometers on deck sections |
| Bed deck articulation | "Bed Name, dining chair" | Causes head of bed (HOB) bed articulation actuator to raise to max angled (up) position, bed foot section to drop to middle of the angled (downward) position, all as controlled by fb from potentiometer on actuators or accelerometers on deck sections |
| Bed deck articulation | "Bed Name, lock (or unlock) head" | Locks (or unlocks) the head deck actuator so the patient can't control it |
| Bed deck articulation | "Bed Name, lock (or unlock) knee" | Locks (or unlocks) the knee deck actuator so the patient can't control it |
| Bed deck articulation | "Bed Name, lock (or unlock) foot" | Locks (or unlocks) the foot deck actuators so the patient can't control them |
| Bed extension | "Bed Name, extend" | Causes foot extension actuator to extend to its maximum position, as controlled by fb from potential on actuator, and foot section extension bladders to inflate |
| Bed extension | "Bed Name, retract" | Causes foot extension actuator to retract to its minimum length position, as controlled by fb from potential on actuator, and foot section extension bladders to deflate |
| Bed tilt | "Bed Name, Trend" | Causes foot end lift actuator to raise to max high (and head end actuator to lower to max low) tilting the foot end of the bed higher than the head end, as controlled by fb from potentiometers on actuators |
| Bed tilt | "Bed Name, ReverseTrend" | Causes head end lift actuator to raise to max high position (and foot end actuator to lower to max low position), tilting the head end of |

TABLE 1-continued

| Type of command | Example voice command | Resulting action software causes on bed |
| --- | --- | --- |
| | | the bed higher than the foot end, as controlled by fb from potentiometers on actuators |
| Bed mattress control | "Bed Name, max inflate" | Causes all air bladders on bed to inflate to their maximum inflation pressure, as controlled by pressure sensors in mattress and pump controller |
| Bed mattress control | "Bed Name, P&V on" | Causes default pulsing bladders in mattress to pulse at a set default frequency and amplitude, as controlled by pump controller |
| Bed mattress control | "Bed Name, P&V off" | Stops pulsing of all bladders, as controlled by pump controller |
| Bed mattress and tilt control | "Bed Name, Boost" | Causes all air bladders to max inflate, bed articulation actuators to go to horizontal position and then to Trend position, as controlled by fb from potentiometers on the actuators and/or accelerometers on the deck sections |
| Bed mattress control | "Bed Name, side exit" | Inflates the seat section to max inflate, for 30 minutes, as controlled by the bladder pressure sensors and pump controller; allows patient to exit side of bed easier |
| Bed mattress control | "Bed Name, turn left" | Causes patient left side turn bladder to fully inflate and patient right side turn bladder to fully deflate, as controlled by pressure sensors for bladders and pump controller |
| Bed mattress control | "Bed Name, turn right" | Causes patient right side turn bladder to fully inflate and patient left side turn bladder to fully deflate, as controlled by pressure sensors for bladders and pump controller |
| Bed mattress control | "Bed Name, CLRT, X minute hold, Y minute length" | Causes patient right side turn bladder to fully inflate and patient left side turn bladder to fully deflate, as controlled by pressure sensors for bladders and pump controller, holds for X minutes, the reverses; continues this continuous lateral rotation therapy for Y minutes; announces error message of X and Y exceed max thresholds |
| Bed mattress control | "Bed Name, MCM on" | Turns on the blower for the topper of the bed, blowing air through the spacer layer of the topper, as controlled by the blower controller |
| Bed mattress control | "Bed Name, MCM off" | Turns off the MCM blower |
| Bed mattress control | "Bed Name, Sleep" | Changes the allowable set points of the pressures to allow for more tolerance in the allowable pressures ranges and fewer pressure changes; pump controls continue to monitor pressure and adjust, but less frequently, as the upper pressure threshold is raised by a default amount and the lower is lowered by a default amount |
| Bed electronics | "Bed Name, Bed Exit On" | Enables the bed exit alert system to the default level of sensitivity; load cells of the bed are monitored by bed control system and if signature bed exit movement is detected, sounds alarm; alarm can be sent through nurse call |
| Bed electronics | "Bed Name, Bed Exit Off" | Turns off the bed exit alert system |
| Bed electronics | "Bed Name, Bed Exit Sensitivity (Hi, Med, Low) | Causes the bed control system to change the level of sensitivity that triggers a bed exit alarm in Bed Exit mode |
| Bed electronics | "Bed Name, 30 degree alarm on" | Enables bed control system to monitor the angle of the head of bed section, as detected by the bed head articulation actuator potentiometer or accelerometer on the head section, and causes the bed to alert if it goes below 30 degrees; nurse call can be sent as well |
| Bed electronics | "Bed Name, 30 degree alarm off" | Causes bed control system to turn off 30 degree alarm |
| Bed electronics | "Bed Name, Silence" | Causes bed control system to silence all audible alarms from bed, for a default number of minutes |
| Bed electronics | "Bed Name, speak alarms" | Causes bed electronics to speak audibly, in a human voice the cause of the bed alarms "Bed not low" "Brake not set" "HR too high" "HR too low" "Siderail not up" "Incontinence event detected" "Patient |

TABLE 1-continued

| Type of command | Example voice command | Resulting action software causes on bed |
|---|---|---|
| | | detected as exiting" "RR too high" "RR too low" |
| Bed electronics | "Bed Name, Speak Heart Rate" | Causes bed electronics (control system) to speak in a human voice the current heart rate detected by under mattress contactless heart rate sensor |
| Bed electronics | "Bed Name, Speak Respiration Rate" | Causes bed electronics (control system) to speak in a human voice the current respiration rate detected by under mattress contactless heart rate sensor |
| Bed electronics | "Bed Name, weigh" | Causes bed electronics (control system) to weigh the patient via the load cells on the bed |
| Bed electronics | "Bed Name, tare" | Causes bed electronics (control system) to set the bed's tare weight to zero based on what is currently on the bed |
| Bed electronics | "Bed Name, open chart" | Causes bed electronics (control system) to open a charting app software on the bed and allow the caregiver to enter information about the patient, such as EMR information |
| Bed electronics | "Bed Name, open association" | Causes bed electronics (control system) to indicate what patient the bed is currently associated with, and their room; interfaces with EMR and ADT and bed locating system to determine |
| Bed brake | "Bed Name, brake" | Causes bed electronics (control system) to set the brakes on the bed (electric signal sent to brake actuator to move to brake position |
| Bed brake | "Bed Name, unbrake" | Causes bed electronics (control system) to release the brakes on the bed (electric signal sent to brake actuator to move to unbrake position |
| Bed siderail | "Bed Name, siderail up" | Causes bed electronics (control system) to move the siderail up (electric signal sent to siderail actuator to move siderail up) |
| Bed siderail | "Bed Name, siderail down" | Causes bed electronics (control system) to move the siderail down (electric signal sent to siderail actuator to move siderail down) |
| Bed propulsion | "Bed Name, come" | Causes bed electronics (control system) to lower the bed propulsion system and move the propulsion system in a direction toward the location of the sound detected |
| Bed propulsion | "Bed Name, stay" | Causes bed electronics (control system) to stop the propulsion system |
| Voice capabilities | "Bed Name, mike off" | Causes bed electronics (control system) to disconnect mike and stop analyzing audio |
| Voice capabilities | "Bed Name, record audio" | Causes bed electronics (control system) to record all sound in room via bed mike |
| Voice capabilities | "Bed Name, stop" | Stops all movement of all bed hi-lo actuators and articulation actuators being run, turns off any percussion and vibration bladder pulsing and any turn bladder filling and deflating, turns off any recording |
| Emergency | "Bed Name, CPR" | Causes bed electronics (control system) to put bed in flat position via bed articulation actuators and fb, and to put the mattress in max inflate. |
| Patient Controls | "Bed Name, Nurse Call" | Activation of the nurse call function |
| Patient Controls | "Bed Name, Lights On (or Off)" | Control the room lights |
| Patient Controls | "Bed Name, Reading Light On (or Off)" | Control the reading light |
| Patient Controls | "Bed Name, Close (or Open) Blinds" | Control the window blinds |
| Patient Controls | "Bed Name, Channel Up (or Down)" | Change the TV channel up or down |
| Patient Controls | "Bed Name, Channel XX (XX = a TV channel number)" | Tune the specified channel on the TV |
| Patient Controls | "Bed Name, Volume Up (or Down)" | Adjust the TV volume |
| Patient Controls | "Bed Name, Mute (or Unmute) Sound" | Turns the TV sound off or on |
| Patient Controls | "Bed Name, CC On (or Off)" | Turns the TV closed captioning on or off |
| Patient Controls | "Bed Name, TV On (or Off)" | Turn the TV on or off |
| Patient Controls | "Bed Name, Current Time" | Bed speaks the current day of the week, calendar day and time of day |

TABLE 1-continued

| Type of command | Example voice command | Resulting action software causes on bed |
|---|---|---|
| Patient Controls | "Bed Name, Bed Firm (or Soft)" | Adjusts the firmness of the mattress one step in the desired direction, within the limits allowable. |
| Patient Controls | "Bed Name, Head Up" | Causes the head of bed actuator to move the head deck up 5 degrees but not further than allowable per the care protocol. The knee deck will adjust per autocontour. If it can't go higher, the bed states "Head of bed is as high as allowable" |
| Patient Controls | "Bed Name, Head Down" | Causes the head of bed actuator to move the head deck down 5 degrees but not further than allowable per the care protocol. The knee deck will adjust per autocontour. If it can't go lower, the bed states "Head of bed is as low as allowable" |
| Patient Controls | "Bed Name, Call XX" | Bed initiates a VOIP phone call to "XX". XX would be previously preset |
| Patient Controls | "Bed Name, Answer Call" | Bed answers an incoming VOIP call |
| Patient Controls | "Bed Name, Hang Up" | Bed ends the current VOIP call |

According to the present disclosure, the controllers of medical devices, such as controller 34 of bed 30, implement rules for determining which command from among two potentially conflicting commands is the one to be implemented. For example, bed 30 includes buttons on siderails 46, some of which are accessible to the patient on the surface of the respective siderail 46 that faces the patient and some of which are accessible to the caregiver on the surface of the respective siderail that faces away from the patient. These can be pressed by the caregiver or the patient to control the respective bed functions. Soft buttons (e.g., buttons or icons rendered on GUI 110) can also be selected by the caregiver to control the respective bed functions.

If a patient button on siderail 46 is pressed to implement a function that is contrary to a voice command issued by a caregiver (e.g., caregiver issues a "head up" voice command to raise a head section of deck 42 and the patient presses the head down button), the present disclosure contemplates that bed 30 will carry out the caregiver voice command and ignore the contrary patient button press in some embodiments. On the other hand, if a caregiver button on siderail 46 is pressed to implement a function that is contrary to a voice command issued by a patient, the present disclosure contemplates that bed 30 will carry out the function corresponding to the caregiver button press and ignore the patient voice request. Thus, in some embodiments, a caregiver command be it via hard or soft button press or via voice input always takes precedence over a contrary patient command be it a hard button press or voice input. In other embodiments, bed 30 will not carry out either function if contrary manual and voice inputs are received.

Embodiments in which some functions of bed 30 are not carried out in light of conflicting inputs while other functions of bed 30 are carried out based on caregiver precedence over the patient are also within the scope of the present disclosure. For example, movement of deck sections of deck 42 of bed 30 may not be carried in light of conflicting inputs because bed movement is considered a higher risk function, whereas adjustment in bladder pressures of the mattress may be carried out according to the caregiver input and not the conflicting patient input since adjustment of bladder pressure is considered a lower risk function.

Some voice commands inherently relate to functions that allow visual feedback to the user due to movement of a portion of a medical device. However, the present disclosure contemplates that, in some embodiments, the amount of movement is limited for the sake of safety. For example, if the caregiver issues a voice command to "lower bed head," the controller 34 of bed 30 will only lower the bed a small number of degrees at a time (e.g., one degree to five degrees just to give an arbitrary movement range) so as to reduce the likelihood of injuring a person who has a body part underneath the moving component. An additional voice input is then needed to move the movable component by an additional increment. For example, the caregiver may provide this additional voice input by saying "more," each time the movement stops. System 20 recognizes that the word "more" is referring back to the initial voice command concerning movement of a portion of the bed 30.

The degrees or amount (e.g., centimeters or inches if lowering the upper frame of the bed 30 relative to the base frame) of change can be configured for all beds 30 system-wide but should be limited to a safe range according to the present disclosure. This feedback based control may be implemented differently depending upon whether the caregiver is physically present in the room as determined by a RTLS, for example, or viewing the patient through video camera using their computer or cell phone while not in the patient room. Thus, a smaller movement threshold may be used if the caregiver is not in the room and a larger movement threshold may be used if the caregiver is in the room. In other embodiments of system 20, the movement thresholds are the same without regard to whether the caregiver issuing the voice command is in the room or not in the room.

In some embodiments, system 20 provides voice command confirmation after a voice commanded function of a medical device, such as bed 30, has finished or otherwise completed its task. For example, such confirmation may be provided as feedback to the caregiver as a text message on the caregiver's mobile phone 22 or shown on GUI 110 of bed 30 or shown on a display screen of audio station 116 or shown on some other computer. As another example, such confirmation may be played as an audible message through the caregiver's mobile phone 22 or through speaker units 48 of bed 30 or through a speaker of an audio station 116 or through the speaker of some other computer. Sometimes the voice command confirmation feedback is intrinsic such that no text message or audible message is needed. For example, if the voice command is to turn on or off a bed light or room light, the user will see that the respective light becomes turned on or turned off, as the case may be. In such inherent visual feedback situations, no further feedback is needed. However, if a user is controlling the bed 30 remotely without such inherent feedback, it would be helpful to get a textual or audible confirmation of the completion of the task. Thus, depending upon the location of the user as determined by a RTLS, the textual and/or audible feedback is provided if the caregiver is not in the room of the medical device being voice controlled.

As alluded to above, the present disclosure contemplates that some voice commands are combo commands. That is a single command is intended to control multiple devices and/or multiple features of one or more medical devices substantially concurrently or one after another in appropriate circumstances. For example, in response to the combo command "sleep mode," system 20 acts to turn off the TV in the room, turn on a walking light or a night light on the base frame of bed 30 that illuminates the floor adjacent the bed 30, returns the bed head and foot angles (i.e., angles of inclination of the head deck section and foot deck section of deck 42) back to what is specified for the patient, sets the room temperature to a default value for sleep using thermostat 92, informs the caregiver via mobile phone 22 or via the nurse call system that the patient has switched to sleep mode, etc. In some embodiment in which devices in the patient room are self-propelling, the sleep mode input results in repositioning of bed 30, one or more chairs, a walker, and the like to appropriate positions in the room if necessary.

The present disclosure further contemplates that group commands can be provided as voice inputs to system 20. The spoken group commands enable controlling all or a subset of beds 30, medical devices, entertainment devices, and/or environment devices all at once. Thus, the "sleep mode" voice command, if fashioned within system 20 as a group command, results in multiple patient rooms having the equipment therein configured according to the sleep mode as described above, for example. Changing rounding parameters for caregivers (e.g., how often the caregivers are required to check on their assigned patients) is another example of a group command according to the present disclosure. In some embodiments, such group commands can be input into system 20 by voice or via a user interface (UI) of a computer. For example, in some embodiments, group commands may only be able to be input into system 20 at a master nurse station computer.

Although certain illustrative embodiments have been described in detail above, variations and modifications exist within the scope and spirit of this disclosure as described and as defined in the following claims.

The invention claimed is:

1. A system to mitigate risk to a patient in a healthcare setting, the system comprising
   a medical product having at least one function that, when operated, has a possibility of causing harm to the patient, circuitry carried by the medical product and having a processor and memory storing software, and
   an array of microphones configured to receive voice inputs from a person in the vicinity of the medical product, wherein the array of microphones is in communication with the circuitry and the software is configured to cooperate with the array of microphones to use beam-forming techniques to infer a direction that the person's eyes are pointed based on the voice inputs, wherein the circuitry is configured to stop the at least one function that has the possibility of causing harm to the patient in response to a vocal stop command being spoken by the person while the person's eyes are inferred to be pointed toward the medical product.

2. The system of claim 1, wherein the medical product comprises a patient bed and the array of microphones are mounted to the patient bed.

3. The system of claim 2, wherein the patient bed comprises at least one siderail that is moveable between a raised position blocking the patient from egressing from the patient bed and a lowered position unblocking the patient from egressing from the patient bed and wherein at least one microphone of the array of microphones is mounted to the at least one siderail.

4. The system of claim 1, wherein the medical product comprises a patient bed and the array of microphones are mounted to either or both of a room wall or a ceiling of a patient room in which the patient bed is situated.

5. The system of claim 1, wherein the array of microphones includes a first microphone mounted to the medical product and a second microphone mounted either a room wall or a ceiling of a patient room in which the medical product is situated.

6. The system of claim 1, wherein the medical product comprises a patient lift and the array of microphones are mounted to either or both of a room wall and a ceiling of a patient room in which the patient lift is situated.

7. The system of claim 6, wherein the patient lift comprises a mobile patient lift or a ceiling-mounted patient lift.

8. The system of claim 1, wherein the medical product comprises a patient bed supporting a mattress and the at least one function comprises one or more of the following: movement of a mattress support section of a mattress-support deck of the patient bed, movement of an upper frame of the patient bed relative to a base frame of the patient bed, operation of a percussion and vibration (P&V) therapy function of the mattress of the patient bed, operation of a turn assist function of the mattress of the patient bed, or operation of a continuous lateral rotation therapy (CLRT) function of the mattress of the patient bed.

9. The system of claim 1, wherein the medical product comprises a surgical table and the at least one function comprises movement of a first surgical table portion relative to a second surgical table portion.

10. The system of claim 1, wherein the array of microphones is in wireless communication with the circuitry of the medical product.

11. The system of claim 1, wherein the array of microphones is in wired communication with the circuitry of the medical product.

12. The system of claim 1, further comprising a mobile phone carried by the person, the mobile phone being configured to receive voice commands from the person and transmit command messages corresponding to the voice commands to the medical product to commence operation of the at least one function.

13. The system of claim 1, further comprising at least one computer that is remote from the medical product, the at least one computer having clinical voice recognition software, and the array of microphones communicating voice commands received from the person to the at least one computer, and wherein the at least one computer is configured to transmit command messages corresponding to the voice commands to the medical product to commence operation of the at least one function.

14. The system of claim 1, wherein the circuitry is configured not to stop the at least one function that has the possibility of causing harm to the patient in response to a vocal stop command being spoken by the person while the person's eyes are not inferred to be pointed toward the medical product.

15. The system of claim 1, wherein the circuitry is configured to be trained to recognize the patient's voice and wherein the circuitry is configured to stop the at least one function that has the possibility of causing harm to the patient in response to a patient-originated vocal stop command being spoken by the patient without regard to directionality of the patient's eyes.

16. The system of claim 15, wherein the medical product comprises a patient bed on which the patient is supported.

17. The system of claim 1,
wherein the array of microphones comprises an array of far-field microphones dispersed throughout the room, and further comprising
at least one computer communicatively coupled to the medical product and to the array of far-field microphones, the at least one computer being configured to (i) combine voice inputs received from the person by the array of far-field microphones, (ii) amplify and discern the voice inputs using beam-forming software, (iii) filter out ambient noise using barge-in software, (iv) execute speech recognition software to determine whether the medical product is to be controlled by the voice inputs, and (v) transmit a control message to the medical product to control a first function of the at least one function of the medical product based on the voice inputs.

18. The system of claim 17, wherein the medical product carries at least one far-field microphone of the array of far-field microphones.

19. The system of claim 18, further comprising a plurality of medical devices that are also in communication the array of far-field microphones and that comprise at least one of the following: a vital signs monitor, a patient bed, a headwall interface, a caregiver badge, a locating tag, a patient identification (ID) bracelet, a patient gown, an audio station of a nurse call system, a patient lift, and a chair.

20. The system of claim 17, wherein the speech recognition software includes one or more of the following: speech-to-text conversion software, code word recognition software, wake word recognition software, and natural language processing (NLP) software.

21. The system of claim 17, wherein the at least one computer is further configured with distance processing software that is executed to determine which far-field microphone of the array of far-field microphones is a closest far-field microphone to the person and to determine whether the medical product is nearest to the closest far-field microphone from among a plurality of medical products.

22. The system of claim 17, wherein the barge-in software determines the ambient noise to filter out based on a signature or frequency of noise that persists for a threshold period of time.

23. The system of claim 17, wherein the at least one computer is further configured with speaker recognition software to determine an identification (ID) of the person providing the voice inputs.

24. The system of claim 23, wherein the speaker recognition software includes one or more of the following: Markov models software, pattern recognition software, voice biometrics software, neural network software, natural language processing (NLP) software, natural language understanding software, and Anaphora resolution software.

25. The system of claim 17, wherein the at least one computer is further configured to determine that the voice inputs include a compound voice command pertaining to the medical product and to a second designated medical device and wherein the at least one computer is further configured to transmit a second control message to the second designated medical device to control a second function of the second designated medical device based on a portion of the voice inputs pertaining to the second medical device.

26. The system of claim 17, wherein the at least one computer is further configured to determine that the voice inputs include a compound voice command pertaining to the first function and to a second function of the medical product and wherein the control message transmitted by the at least one computer to the medical product includes a first portion to control the first function and a second portion to control the second function.

\* \* \* \* \*